(12) United States Patent
Andersen

(10) Patent No.: US 11,298,413 B2
(45) Date of Patent: Apr. 12, 2022

(54) VACCINE COMPOSITIONS COMPRISING C—C MOTIF CHEMOKINE 22 (CCL22) OR FRAGMENTS THEREOF

(71) Applicant: IO Biotech ApS, Copenhagen N (DK)

(72) Inventor: Mads Hald Andersen, Nærum (DK)

(73) Assignee: IO BIOTECH APS, Copenhagen (DK)

( * ) Notice: Subject to any disclaimer, the term of this patent is extended or adjusted under 35 U.S.C. 154(b) by 0 days.

(21) Appl. No.: 15/758,187

(22) PCT Filed: Sep. 16, 2016

(86) PCT No.: PCT/DK2016/050301
§ 371 (c)(1),
(2) Date: Mar. 7, 2018

(87) PCT Pub. No.: WO2017/045691
PCT Pub. Date: Mar. 23, 2017

(65) Prior Publication Data
US 2019/0008939 A1    Jan. 10, 2019

(30) Foreign Application Priority Data
Sep. 16, 2015   (DK) .......................... PA 2015 70591

(51) Int. Cl.
*A61K 39/00* (2006.01)
*C07K 14/52* (2006.01)
*A61P 35/00* (2006.01)
*A61K 45/06* (2006.01)

(52) U.S. Cl.
CPC ...... *A61K 39/001142* (2018.08); *A61K 45/06* (2013.01); *A61P 35/00* (2018.01); *C07K 14/521* (2013.01); *A61K 2039/5158* (2013.01)

(58) Field of Classification Search
None
See application file for complete search history.

(56) References Cited

U.S. PATENT DOCUMENTS 7,018,627 B1    3/2006   Gray et al.

FOREIGN PATENT DOCUMENTS

| WO | 96/40923 A1 | 12/1996 |
|---|---|---|
| WO | 200078334 A1 | 12/2000 |
| WO | 2009143843 A1 | 12/2009 |
| WO | 2011139738 A1 | 11/2011 |
| WO | 2013056716 A1 | 4/2013 |
| WO | 2014028644 A1 | 2/2014 |
| WO | WO 2014/037811 * | 3/2014 |
| WO | 2014170389 A1 | 10/2014 |

OTHER PUBLICATIONS

Kovjazin et al., Human Vaccines & Immunotherapeutics 10:9, 2733-2740; Sep. 2014.*
Greenspan et al. Nature Biotechnology 7: 936-937, 1999.*
Andersen MH et al, "Phosphorylated Peptides can be Transported by TAP Molecules, Preseented by Class I MHC Molecules, and Recognized by Phosphopeptide-Specific CTL," J Immunol, 163: 3812-8, 1999.
Guo et al, "Macrophage-Derived Chemokine Gene Transfer Results in Tumor Regression in Murine Lung Carcinoma Model through Efficient Induction of Antitumor Immunity," Gene Therapy, vol. 9, No. 12, 2002, 793-803.
Qin et al, "CCL22 Recruits CD4-positive CD25-positive Regulatory T Cells into Malignant Pleural Effusion," Clin Cancer Res. 15(7), 2231-2237, 2009.

* cited by examiner

*Primary Examiner* — Marianne P Allen
(74) *Attorney, Agent, or Firm* — Cooley LLP

(57) ABSTRACT

The present disclosure relates to CCL22 as a novel T cell target in cancer immunosuppression.

5 Claims, 32 Drawing Sheets

Specification includes a Sequence Listing.

B

C

E

F

A  No peptide    CCL22-3

C

D

SEQUENCE LISTING

```
<160> NUMBER OF SEQ ID NOS: 16

<210> SEQ ID NO 1
<211> LENGTH: 22
<212> TYPE: PRT
<213> ORGANISM: Homo sapiens

<400> SEQUENCE: 1

Met Asp Arg Leu Gln Thr Ala Leu Leu Val Val Leu Val Leu Leu Ala
1               5                   10                  15

Val Ala Leu Gln Ala Thr
            20

<210> SEQ ID NO 2
<211> LENGTH: 9
<212> TYPE: PRT
<213> ORGANISM: Homo sapiens

<400> SEQUENCE: 2

Ala Leu Leu Val Val Leu Val Leu Leu
1               5

<210> SEQ ID NO 3
<211> LENGTH: 9
<212> TYPE: PRT
<213> ORGANISM: Homo sapiens

<400> SEQUENCE: 3

Arg Leu Gln Thr Ala Leu Leu Val Val
1               5

<210> SEQ ID NO 4
<211> LENGTH: 10
<212> TYPE: PRT
<213> ORGANISM: Homo sapiens

<400> SEQUENCE: 4

Arg Leu Gln Thr Ala Leu Leu Val Val Leu
1               5                   10

<210> SEQ ID NO 5
<211> LENGTH: 9
<212> TYPE: PRT
<213> ORGANISM: Homo sapiens

<400> SEQUENCE: 5

Val Leu Val Leu Leu Ala Val Ala Leu
1               5

<210> SEQ ID NO 6
<211> LENGTH: 9
<212> TYPE: PRT
<213> ORGANISM: Homo sapiens

<400> SEQUENCE: 6

Gln Thr Ala Leu Leu Val Val Leu Val
1               5

<210> SEQ ID NO 7
<211> LENGTH: 9
<212> TYPE: PRT
<213> ORGANISM: Homo sapiens
```

```
<400> SEQUENCE: 7

Leu Leu Ala Val Ala Leu Gln Ala Thr
1               5

<210> SEQ ID NO 8
<211> LENGTH: 10
<212> TYPE: PRT
<213> ORGANISM: Homo sapiens

<400> SEQUENCE: 8

Leu Leu Val Val Leu Val Leu Leu Ala Val
1               5                   10

<210> SEQ ID NO 9
<211> LENGTH: 9
<212> TYPE: PRT
<213> ORGANISM: Homo sapiens

<400> SEQUENCE: 9

Leu Val Val Leu Val Leu Leu Ala Val
1               5

<210> SEQ ID NO 10
<211> LENGTH: 9
<212> TYPE: PRT
<213> ORGANISM: Homo sapiens

<400> SEQUENCE: 10

Thr Ala Leu Leu Val Val Leu Val Leu
1               5

<210> SEQ ID NO 11
<211> LENGTH: 24
<212> TYPE: PRT
<213> ORGANISM: Homo sapiens

<400> SEQUENCE: 11

Met Asp Arg Leu Gln Thr Ala Leu Leu Val Val Leu Val Leu Leu Ala
1               5                   10                  15

Val Ala Leu Gln Ala Thr Glu Ala
            20

<210> SEQ ID NO 12
<211> LENGTH: 93
<212> TYPE: PRT
<213> ORGANISM: Homo sapiens

<400> SEQUENCE: 12

Met Asp Arg Leu Gln Thr Ala Leu Leu Val Val Leu Val Leu Leu Ala
1               5                   10                  15

Val Ala Leu Gln Ala Thr Glu Ala Gly Pro Tyr Gly Ala Asn Met Glu
            20                  25                  30

Asp Ser Val Cys Cys Arg Asp Tyr Val Arg Tyr Arg Leu Pro Leu Arg
                35                  40                  45

Val Val Lys His Phe Tyr Trp Thr Ser Asp Ser Cys Pro Arg Pro Gly
        50                  55                  60

Val Val Leu Leu Thr Phe Arg Asp Lys Glu Ile Cys Ala Asp Pro Arg
65                  70                  75                  80

Val Pro Trp Val Lys Met Ile Leu Asn Lys Leu Ser Gln
                85                  90
```

<210> SEQ ID NO 13
<211> LENGTH: 22
<212> TYPE: PRT
<213> ORGANISM: Mus musculus

<400> SEQUENCE: 13

Met Ala Thr Leu Arg Val Pro Leu Leu Val Ala Leu Val Leu Leu Ala
1               5                   10                  15

Val Ala Ile Gln Thr Ser
            20

<210> SEQ ID NO 14
<211> LENGTH: 10
<212> TYPE: PRT
<213> ORGANISM: Mus musculus

<400> SEQUENCE: 14

Val Ala Leu Val Leu Leu Ala Val Ala Ile
1               5                   10

<210> SEQ ID NO 15
<211> LENGTH: 92
<212> TYPE: PRT
<213> ORGANISM: Mus musculus

<400> SEQUENCE: 15

Met Ala Thr Leu Arg Val Pro Leu Leu Val Ala Leu Val Leu Leu Ala
1               5                   10                  15

Val Ala Ile Gln Thr Ser Asp Ala Gly Pro Tyr Gly Ala Asn Val Glu
            20                  25                  30

Asp Ser Ile Cys Cys Gln Asp Tyr Ile Arg His Pro Leu Pro Ser Arg
        35                  40                  45

Leu Val Lys Glu Phe Phe Trp Thr Ser Lys Ser Cys Arg Lys Pro Gly
    50                  55                  60

Val Val Leu Ile Thr Val Lys Asn Arg Asp Ile Cys Ala Asp Pro Arg
65                  70                  75                  80

Gln Val Trp Val Lys Lys Leu Leu His Lys Leu Ser
                85                  90

<210> SEQ ID NO 16
<211> LENGTH: 10
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa is Val or Ala
<220> FEATURE:
<221> NAME/KEY: MISC_FEATURE
<222> LOCATION: (10)..(10)
<223> OTHER INFORMATION: Xaa is Ile or Leu

<400> SEQUENCE: 16

Val Xaa Leu Val Leu Leu Ala Val Ala Xaa
1               5                   10

VACCINE COMPOSITIONS COMPRISING C—C MOTIF CHEMOKINE 22 (CCL22) OR FRAGMENTS THEREOF

The instant application contains a Sequence Listing which has been submitted electronically in ASCII format and is hereby incorporated by reference in its entirety. Said ASCII copy, created Sep. 20, 2018, is named "Corrected Sequence Listing N414655US ST25.txt" and is 4707 bytes in size.

FIELD OF INVENTION

The present invention relates to the field of prophylaxis and therapy of cancer. In particular there is provided a protein C-C motif chemokine 22 (CCL22) or peptide fragments here of that are capable of eliciting anti-cancer immune responses. Specifically, the invention relates to the use of CCL22 or peptides derived thereof or CCL22 specific T-cells for treatment of cancer. The invention thus relates to an anti-cancer vaccine which optionally may be used in combination with other immunotherapies and to CCL22 specific T-cells adoptively transferred or induced in vivo by vaccination as a treatment of cancer. It is an aspect of the invention that the medicaments herein provided may be used in combination with cancer chemotherapy treatment. A further aspect relates to the prophylaxis and therapy of infections by the same means as described above.

The use of CCL22 and immunogenic peptide fragments hereof in cancer and infection treatment, diagnosis and prognosis is also provided.

BACKGROUND OF INVENTION

The immune system is a complex arrangement of cells and molecules that preserve the integrity of the organism by the elimination of all elements that are judged to be dangerous. Several regulatory mechanisms function to terminate immune responses to antigens, returning the immune system to a basal state after the antigen has been cleared, and to maintain the unresponsiveness, or tolerance, to self-antigens. Unfortunately, some of the mechanisms preventing autoimmunity are hijacked by cancers to attain immune escape. Indeed, in 'The Hallmarks of cancer' by Hanahan and Weinberg, evasion of immune destruction is now listed as an emerging hallmark (Nomi et al., 2007). This evasion of immune destruction is based on several mechanisms. Solid tumors are composed of the cancerous cells themselves as well as the stroma that not only provides a supportive framework but also allows immune evasion. For this purpose, tumors attract and/or convert immune competent cells that procreate and sustain an immune permissive microenvironment. These immune competent cells, which are normally involved in the elaborate network of central and peripheral tolerance mechanisms maintaining immune homeostasis, include factor forkhead box P3 (Foxp3)-positive regulatory T cells (Tregs), NKT cells, dendritic cell subtypes, myeloid derived suppressor cells (MDSC), M2 (aka tumor-associated) macrophages, and granulocytes. The mechanism by which CCL22 is thought to act in cancer is illustrated in FIG. 1.

This immune evasion is harmful in the context of cancer immunotherapy. Thus, the targeting of one or more immunosuppressive pathways may be highly useful in combination with anti-cancer immunotherapy in which immune-suppressive mechanisms antagonize the required effects. Several different potential therapeutic strategies with which to target immune suppression in cancer are under investigation, especially the blocking of inhibitory pathways using monoclonal antibodies.

SUMMARY OF INVENTION

The invention is as defined in the claims.

The expression of CCL22 and the potential CCL22-induced cancer immunosuppression poses a problem in the treatment of cancer.

The problem of cancer immunosuppression is solved by the present invention, which provides CCL22 as a novel T cell target.

Thus, the present invention provides materials and methods for treatment of cancer diseases by targeting CCL22 expressing cancer cells directly and by killing CCL22 expressing cancer cells. This is done by enabling T cells to recognize the CCL22 expressing cells. Interestingly, the present invention discloses that cytotoxic immune responses against CCL22 expressing cells can be raised even though CCL22 expressing cells may antagonize the desired effects of other immunotherapeutic approaches. Thus, despite the fact that CCL22 enables tumor evasion by attracting immune suppressive cells such as Tregs, the present invention shows that the immune system can react against a chemokine and that it is possible to raise a specific immune response against CCL22. This provides a novel mechanism for treating e.g. cancer by inhibiting the recruitment of immune suppressive cells to the tumour and CCL22-expressing cancer cells.

Likewise, the invention provides materials and methods for treatment of other diseases, which normally may invoke an immune response, e.g. infections. In the methods of the invention T cells are enabled to kill CCL22 expressing antigen-presenting cells (APCs) and/or dendritic cells (DCs).

Thus, the invention exploits expression of the immune suppressing chemokine CCL22 in cancer cells and targets these CCL22 expressing cells.

It is an aspect of the invention to provide vaccine compositions which surprisingly can generate an immune response against the self-protein CCL22.

Herein is provided a vaccine composition comprising:
a) one or more of the following:
   (i) CCL22 of SEQ ID NO: 12 or SEQ ID NO: 15 or an immunogenically active peptide fragment of CCL22 comprising a consecutive sequence of amino acids of CCL22 of SEQ ID NO:12 or SEQ ID NO: 15;
   (ii) an immunogenically active peptide fragment of CCL22, which is an MHC Class I-restricted peptide fragment or MHC Class II-restricted peptide fragment;
   (iii) a functional homologue of the polypeptides under (i) and (ii), wherein said functional homologue shares at least 70% sequence identity with SEQ ID NO:12 or SEQ ID NO: 15, and/or said functional homologue is an immunogenically active polypeptide consisting of a sequence identical to a consecutive sequence of amino acids of SEQ ID NO:1, SEQ ID NO: 4, SEQ ID NO: 11 or SEQ ID NO: 14, except that at the most three amino acids have been substituted, such as at the most two amino acids, such as at the most one amino acid;
   (iv) a polypeptide comprising any of the polypeptides under (i), (ii) or (iii));
   (v) a nucleic acid encoding any of the polypeptides under (i), (ii) or (iii); and b) an adjuvant for use as a medicament.

The vaccine compositions may be used as a medicament, and may for example be for treatment of a cancer disease where CCL22 is expressed or for treatment of an infection causing CCL22 expression in antigen-presenting cells (APCs).

The invention also provides kit-of-parts comprising the vaccine composition and a second active ingredient.

The invention also describes complexes of a peptide fragment of CCL22 and a Class I HLA or a Class II HLA molecule or a fragment of such molecule. Said peptide fragment may e.g. be any of the peptide fragments of CCL22 described herein below in the sections "Immunogenically active peptide fragment of CCL22", "Polypeptide comprising CCL22 or a fragment thereof" and "MHC".

The invention further discloses methods of detecting in an individual suffering from a clinical condition the presence of CCL22 reactive T-cells, the method comprising contacting a tumor tissue or a blood sample with the complex comprising peptide fragments of CCL22 described above and detecting binding of the complex to the tissue or the blood cells.

The invention also discloses molecules that are capable of binding specifically to a peptide fragment of CCL22 e.g. be any of the peptide fragments of CCL22 described herein below in the sections "Immunogenically active peptide fragment of CCL22", "Polypeptide comprising CCL22 or a fragment thereof" and "MHC".

The invention also provides methods of treating a clinical condition characterized by the expression of CCL22, the method comprising administering to an individual suffering from said clinical condition an effective amount of the vaccine compositions of the invention, of a kit-of-parts of the invention, of a composition of the invention and/or of an immunogenically active peptide fragment of CCL22, e.g. be any of the peptide fragments of CCL22 described herein below in the sections "Immunogenically active peptide fragment of CCL22", "Polypeptide comprising CCL22 or a fragment thereof" and "MHC".

The invention also provides use of the vaccine compositions of the invention in the manufacture of a medicament for the treatment or prevention of a clinical condition, e.g. cancer and/or inflammations.

The invention also provides methods of monitoring immunization, said method comprising the steps of
a) providing a blood sample from an individual
b) providing an immunogenically active peptide fragment comprising a consecutive sequence of SEQ ID NO: 12 or a functional homologue thereof having at least 70% identity to SEQ ID NO: 12 or a nucleic acid encoding said peptide fragment or functional homologue;
c) determining whether said blood sample comprises antibodies or T-cells comprising T-cell receptors specifically binding the protein or peptide
thereby determining whether an immune response to said protein or peptide has been raised in said individual.

Further, the invention provides immunogenically active CCL22 peptide fragments comprising a consecutive sequence of the CCL22 fragment of SEQ ID NO: 1, SEQ ID NO: 4 or SEQ ID NO: 11 or a functional homologue thereof, said functional homologue being a polypeptide of identical sequence except that at the most three amino acids have been substituted, or a nucleic acid encoding said CCL22 peptide fragment for use in the treatment or prevention of clinical conditions associated with expression of CCL22, such as cancer and/or infections.

DEFINITIONS

Figure 1:
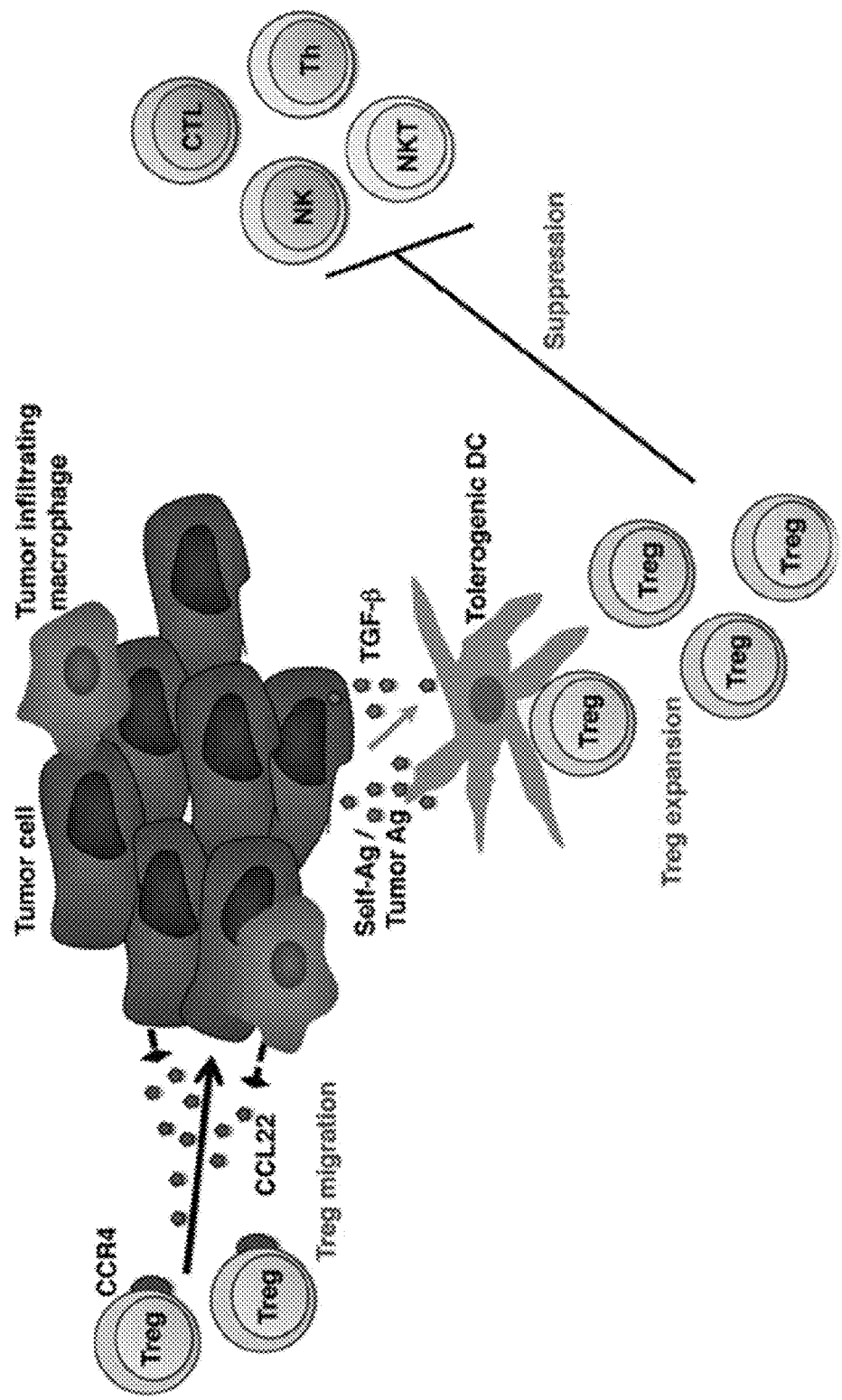
FIG. 1: Action of CCL22 in cancer.

Adjuvant: Any substance whose admixture with an administered immunogenic determinant/antigen/nucleic acid construct increases or otherwise modifies the immune response to said determinant.

Antigen: Any substance that can bind to a clonally distributed immune receptor (T-cell or B-cell receptor). Usually a peptide, polypeptide or a multimeric polypeptide. Antigens are preferably capable of eliciting an immune response.

APC: Antigen-presenting cell. An APC is a cell that displays antigen complexed with MHC on its surface. T-cells may recognize this complex using their T-cell receptor (TCR). APCs fall into two categories: professional, (of which there are three types: Dendritic cells, macrophages and B-cells) or non-professional (does not constitutively express the Major histocompatibility complex proteins required for interaction with naive T cells; these are expressed only upon stimulation of the non-professional APC by certain cytokines such as IFN-γ).

Boost: To boost by a booster shot or dose is to administer an additional dose of an immunizing agent, such as a vaccine, administered at a time after the initial dose to sustain the immune response elicited by the previous dose of the same agent.

Carrier: Entity or compound to which antigens are coupled to aid in the induction of an immune response.

CCL: C-C motif chemokine 22. Wild-type, human sequence of CCL22 is presented in SEQ ID NO: 12.

$CCL22_{xx-yy}$: As used herein this nomenclature refers to a polypeptide fragment of CCL22 consisting of amino acids xx-yy of SEQ ID NO: 12. mCCL22 refers to murine CCL22, and $mCCL22_{xx-yy}$ refers to a polypeptide fragment of mCCL22 consisting of amino acids xx-yy of SEQ ID NO: 15.

Chimeric protein: A genetically engineered protein that is encoded by a nucleotide sequence made by a splicing together of two or more complete or partial genes or a series of (non)random nucleic acids.

Clinical condition: A condition that requires medical attention, herein especially conditions associated with the expression of CCL22. Examples of such conditions include: proliferative disorders, such as cancers and infections.

Complement: A complex series of blood proteins whose action "complements" the work of antibodies. Complement destroys bacteria, produces inflammation, and regulates immune reactions.

CTL: Cytotoxic T lymphocyte. A sub group of T-cells expressing CD8 along with the T-cell receptor and therefore able to respond to antigens presented by class I molecules.

Delivery vehicle: An entity whereby a nucleotide sequence or polypeptide or both can be transported from at least one media to another.

DC: Dendritic cell. (DCs) are immune cells and form part of the mammalian immune system. Their main function is to process antigen material and present it on the surface to other cells of the immune system, thus functioning as antigen-presenting cells (APCs).

Fragment: is used to indicate a non-full length part of a nucleic acid or polypeptide. Thus, a fragment is itself also a nucleic acid or polypeptide, respectively.

Functional homologue: A functional homologue may be any polypeptide that exhibits at least some sequence identity with a wild type version of a polypeptide and has retained at least one aspect of the original functionality. Herein a functional homologue of CCL22 or an immunogenic peptide fragment thereof is a polypeptide sharing at least some sequence identity with CCL22 or a fragment thereof and which has the capability to induce an immune response to cells expressing CCL22.

Immunogenically active peptide: Peptide capable of eliciting an immune response in at least one individual after administration to said individual.

Individual: Generally any species or subspecies of bird, mammal, fish, amphibian, or reptile, preferably a mammal, most preferably a human being.

Infection: Herein the term "infection" relates to any kind of clinical condition involving an invasion of the host organism by disease-causing agents. In particular, infection refers to a clinical condition involving invasion of an individual by a pathogen.

Isolated: used in connection with nucleic acids, polypeptides, and antibodies disclosed herein 'isolated' refers to these having been identified and separated and/or recovered from a component of their natural, typically cellular, environment. Nucleic acids, polypeptides, and antibodies of the invention are preferably isolated, and vaccines and other compositions of the invention preferably comprise isolated nucleic acids, polypeptides or isolated antibodies.

MHC: Major histocompatibility complex, two main subclasses of MHC, Class I and Class II exist.

Nucleic acid: A chain or sequence of nucleotides that convey genetic information. In regards to the present invention the nucleic acid is generally a deoxyribonucleic acid (DNA).

Nucleic acid construct: A genetically engineered nucleic acid. Typically comprising several elements such as genes or fragments of same, cDNAs, promoters, enhancers, terminators, polyA tails, linkers, polylinkers, operative linkers, multiple cloning sites (MCS), markers, STOP codons, other regulatory elements, internal ribosomal entry sites (IRES) or others.

Operative linker: A sequence of nucleotides or amino acid residues that bind together two parts of a nucleic acid construct or (chimeric) polypeptide in a manner securing the biological processing of the nucleic acid or polypeptide.

Pathogen: a specific causative agent of disease, especially a biological agent such as a virus, bacteria, prion or parasite that can cause disease to its host, also referred to as an infectious agent.

PBL: Peripheral blood cells are the cellular components of blood, consisting of red blood cells, white blood cells, and platelets, which are found within the circulating pool of blood and not sequestered within the lymphatic system, spleen, liver, or bone marrow.

PBMC: A Peripheral Blood Mononuclear Cell (PBMC) is a blood cell having a round nucleus, such as a lymphocyte or a monocyte. These blood cells are a critical component in the immune system to fight infection and adapt to intruders. The lymphocyte population consists of T cells (CD4 and CD8 positive ~75%), B cells and NK cells (~25% combined).

Polypeptide: Plurality of covalently linked amino acid residues defining a sequence and linked by amide bonds. The term is used analogously with oligopeptide and peptide. The term polypeptide also embraces post-translational modifications introduced by chemical or enzyme-catalyzed reactions, as are known in the art. The term can refer to a variant or fragment of a polypeptide.

Pharmaceutical carriers: also termed excipients, or stabilizers are non-toxic to the cell or individual being exposed thereto at the dosages and concentrations employed. Often the pharmaceutical carrier is an aqueous pH buffered solution. Examples of pharmaceutical carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Plurality: At least two.

Proliferative disorder: Herein any preneoplastic or neoplastic disease, benign or malignant, where "neoplastic" refers to an abnormal proliferation of cells. A non-limiting example of a proliferative disorder is cancer.

Promoter: A binding site in a DNA chain at which RNA polymerase binds to initiate transcription of messenger RNA by one or more nearby structural genes.

Signal peptide: A short sequence of amino acids that determine the eventual location of a protein in the cell, also referred to as sorting peptide.

Surfactant: A surface active agent capable of reducing the surface tension of a liquid in which it is dissolved. A surfactant is a compound containing a polar group which is hydrophilic and a non-polar group which is hydrophobic and often composed of a fatty chain.

Treg: Regulatory T cells/T lymphocytes

Treatment: The term "treatment" as used herein may refer to curative treatment and/or to ameliorating treatment and/or to treatment reducing symptoms of disease and/or treatment delaying disease progression.

Vaccine: A substance or composition capable of inducing an immune response in an individual, and particularly in a mammal, preferably in a human being. Also referred to as an immunogenic composition in the present text. A vaccine according to the present invention may frequently be a composition comprising at least an adjuvant and an immunogenic peptide. An immune response against an agent is a humoral, antibody and/or cellular response inducing memory in an organism, resulting in that said agent is being met by a secondary rather than a primary response, thus reducing its impact on the host organism. Said agent may be pathogen. In the context of the present invention the agent is preferably a cancer cell. A vaccine of the present invention may be given as a prophylaxis, in order to reduce the risk of encountering a clinical condition and/or as a therapeutic medicament for treatment of a clinical condition. The composition may comprise one or more of the following: antigen(s), nucleic acid constructs encoding one or more antigens, carriers, adjuvants and pharmaceutical carriers.

Variant: a 'variant' of a given reference nucleic acid or polypeptide refers to a nucleic acid or polypeptide that displays a certain degree of sequence homology/identity to said reference nucleic acid or polypeptide but is not identical to said reference nucleic acid or polypeptide.

DETAILED DESCRIPTION OF THE INVENTION

The present disclosure relates to a vaccine composition comprising:

a) one or more of the following:
  (i) CCL22 of SEQ ID NO: 12 or SEQ ID NO: 15 or an immunogenically active peptide fragment of CCL22 comprising a consecutive sequence of amino acids of CCL22 of SEQ ID NO: 12 or SEQ ID NO: 15;
  (ii) an immunogenically active peptide fragment of CCL22, which is an MHC Class I-restricted peptide fragment or MHC Class II-restricted peptide fragment;
  (iii) a functional homologue of the polypeptides under (i) and (ii), wherein said functional homologue shares at least 70% sequence identity with SEQ ID NO: 12 or SEQ ID NO: 15, and/or said functional homologue is an immunogenically active polypeptide consisting of a sequence identical to a consecutive sequence of amino acids of SEQ ID NO: 12 or SEQ ID NO: 15, except that at the most three amino acids have been substituted, such as at the most two amino acids, such as at the most one amino acid;
  (iv) a polypeptide comprising any of the polypeptides under (i), (ii) or (iii));
  (v) a nucleic acid encoding any of the polypeptides under (i), (ii) or (iii); and
b) an adjuvant for use as a medicament.

The disclosure also relates to a kit-of-parts comprising the vaccine compositions described herein, and a second active ingredient.

In yet another aspect, the disclosure relates to a complex of a peptide fragment as defined herein and a Class I HLA or a Class II HLA molecule or a fragment of such molecule.

In yet another aspect, the disclosure relates to a method of detecting in an individual suffering from a clinical condition the presence of CCL22 reactive T-cells, the method comprising contacting a tumor tissue or a blood sample with a complex of the disclosure and detecting binding of the complex to the tissue or the blood cells.

In yet another aspect, a molecule that is capable of binding specifically to a peptide fragment as defined herein is disclosed.

In yet another aspect, a molecule that is capable of blocking the binding of the molecule capable of binding specifically to a peptide fragment as defined herein is disclosed.

In yet another aspect, a method of treating or preventing a clinical condition characterized by the expression of CCL22, the method comprising administering to an individual suffering from said clinical condition an effective amount of the composition, the molecule or the kit-of-parts described herein is disclosed.

In yet another aspect, the disclosure relates to the use of the vaccine composition, the kit-of-parts or the molecule described herein in the manufacture of a medicament for the treatment or prevention of a clinical condition.

In yet another aspect, the disclosure relates to a method of monitoring immunization, said method comprising the steps of
  a) providing a blood sample from an individual
  b) providing CCL22 of SEQ ID NO: 12 or SEQ ID NO: 15 or an immunogenically active peptide fragment comprising a consecutive sequence of SEQ ID NO: 12 or SEQ ID NO: 15 or a functional homologue thereof having at least 70% identity to SEQ ID NO: 12 or SEQ ID NO: 15 or a nucleic acid encoding said peptide fragment or functional homologue;
  c) determining whether said blood sample comprises antibodies or T-cells comprising T-cell receptors specifically binding the protein or peptide
  thereby determining whether an immune response to said protein or peptide has been raised in said individual.

In yet another aspect, the disclosure relates to an immunogenically active CCL22 peptide fragment comprising a consecutive sequence of SEQ ID NO: 12 or SEQ ID NO: 15 or a functional homologue thereof, said functional homologue being a polypeptide of identical sequence except that at the most three amino acids have been substituted, or a nucleic acid encoding said CCL22 peptide fragment for use in the treatment or prevention of clinical conditions associated with expression of CCL22, such as cancer and/or inflammation.

Vaccine Composition

It is one of aspect of the present invention to provide a vaccine composition comprising one or more of the following:
  (i) CCL22 of SEQ ID NO: 12 or SEQ ID NO: 15 or an immunogenically active peptide fragment of CCL22 comprising a consecutive sequence of amino acids of CCL22 of SEQ ID NO:12 or SEQ ID NO: 15;
  (ii) an immunogenically active peptide fragment of CCL22, which is an MHC Class I-restricted peptide fragment or MHC Class II-restricted peptide fragment;
  (iii) a functional homologue of the polypeptides under (i) and (ii), wherein said functional homologue shares at least 70% sequence identity with SEQ ID NO:12 or SEQ ID NO: 15, and/or said functional homologue is an immunogenically active polypeptide consisting of a sequence identical to a consecutive sequence of amino acids of SEQ ID NO:12 or SEQ ID NO: 15, except that at the most three amino acids have been substituted, such as at the most two amino acids, such as at the most one amino acid;
  (iv) a polypeptide comprising any of the polypeptides under (i), (ii) or (iii));
  (v) a nucleic acid encoding any of the polypeptides under (i), (ii) or (iii).

In addition to the above-mentioned said vaccine composition preferably also comprises an adjuvant, which for example may be any of the adjuvants described herein below in the section "Adjuvant".

Functional homologues, which may be used in the vaccine compositions of the invention are described herein below in the sections "C-C-motif chemokine 22"; "Immunogenically active peptide fragment of CCL22"; "Functional homologues" and "Polypeptides comprising CCL22 or a fragment thereof".

C-C Motif Chemokine 22 (CCL22)

C-C motif chemokine 22 is a protein that in humans is encoded by the CCL22 gene. The amino acid sequence of human CCL22 is set forth in SEQ ID NO: 12, and the sequence of murine CCL22 in SEQ ID NO: 15. The protein encoded by this gene is secreted by dendritic cells and macrophages, and elicits its effects on its target cells by interacting with cell surface chemokine receptors such as CCR4. The gene for CCL22 is located in human chromosome 16 in a cluster with other chemokines called CX3CL1 and CCL17. CCL22 chemoattracts and recruits CD25+ CD4+ Tregs expressing CCR4. Expression of CCL22 has been previously shown to cause accumulation of Foxp3+ Tregs in ovarian, prostate, esophageal, gastric, and breast carcinomas.

CCL22 according to the present disclosure may be any useful CCL22. Throughout this disclosure, the term "CCL22" refers to full-length CCL22, such as human CCL22 as set forth in SEQ ID NO: 12 or murine CCL22 as set forth in SEQ ID NO: 15. In general it is preferred that CCL22 is of the same species which it is intended to treat with the vaccine compositions of the disclosure. In preferred embodiments of the disclosure, the vaccine composition is intended for administration to a human being, and hence CCL22 may be human CCL22. The amino acid sequence of wild type human CCL22 is presented as SEQ ID NO: 12 herein. In other embodiments, CCL22 may be murine CCL22 as set forth in SEQ ID NO: 15.

Thus, CCL22 may preferably be CCL22 of SEQ ID NO: 12 or a functional homologue thereof sharing at least 70% sequence identity to CCL22 of SEQ ID NO: 12, and accordingly, a functional homologue preferably having at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with human CCL22 of SEQ ID NO: 12.

CCL22 may in other embodiments be CCL22 of SEQ ID NO: 15 or a functional homologue thereof sharing at least 70% sequence identity to CCL22 of SEQ ID NO: 15, and accordingly, a functional homologue preferably having at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with human CCL22 of SEQ ID NO: 15.

Functional homologues of CCL22 and methods for determining sequence identity are described in more detail in the section "Functional homologues" herein below.

Since CCL22 potentially may have unwanted activity, then in one embodiment of the disclosure, the vaccine composition comprises mutant CCL22, which is not capable of chemoattracting and recruiting CD25+CD4+ Tregs expressing CCR4, or which are only capable of doing so with an activity of at the most 10% of the CCL22 of SEQ ID NO: 12. Such mutant CCL22 may in particular be CCL22 of SEQ ID NO: 12 wherein one or more of the amino acids have been mutated to another amino acid or are deleted. The mutant CCL22 may also be a mutant CCL22 fragment, for example a mutant fragment of SEQ ID NO: 1, SEQ ID NO: 3, SEQ ID NO: 4, SEQ ID NO: 11, SEQ ID NO: 13 SEQ ID NO: 14 or SEQ ID NO: 16, wherein one or more of the amino acids have been mutated to another amino acid or are deleted. In the context of the present invention a "functional homologue" of CCL22 may be mutant CCL22, which does not have the catalytic activity of wild type CCL22, but which has the capability to induce an immune response to cells expressing CCL22.

Immunogenically Active Peptide Fragment of CCL22

The wild-type human CCL22, i.e. the naturally occurring non-mutated version of the protein is identified in SEQ ID NO: 12. The wild-type murine CCL22 is identified in SEQ ID NO: 15. The present invention covers vaccine compositions comprising human or murine CCL22; immunologically active peptide fragments of human or murine CCL22; peptide fragments of human or murine CCL22, wherein at the most two amino acids have been substituted; and/or functional homologues of C human or murine CL22 comprising a sequence identity of at least 70% to SEQ ID NO: 12 or SEQ ID NO: 15. The term polypeptide fragment is used herein to define any non-full length (as compared to SEQ ID NO: 12 or SEQ ID NO:15) string of amino acid residues that are directly derived from or synthesized to be identical with at least part of SEQ ID NO: 12 or SEQ ID NO: 15. The peptide fragment may for example be a consecutive sequence of in the range of from 5 to 24 amino acids of SEQ ID: 12 or SEQ ID NO: 15, such as from 5 to 22 amino acids of SEQ ID NO: 12 or SEQ ID NO: 15, for example from 8 to 22 amino acids of SEQ ID NO: 12 or SEQ ID NO: 15, for example the peptide fragment may comprise SEQ ID NO: 1, SEQ ID NO: 3, SEQ ID NO: 4, SEQ ID NO: 11, SEQ ID NO: 13, SEQ ID NO: 14 or SEQ ID NO: 16.

A functional homologue can be defined as a full length or fragment of CCL22 that differs in sequence from the wild-type CCL22, such as wild-type human or murine CCL22, but is still capable of inducing an immune response against CCL22 expressing cells such as cancer cells and DCs. The CCL22 expressed in these cells may be wild type or endogenously mutated (such as a congenital mutant or a mutation induced during cell division or other). A functional homologue may be a mutated version or an alternative splice variant of the wild-type CCL22. In another aspect, functional homologues of CCL22 are defined as described herein below. A functional homologue may be, but is not limited to, a recombinant version of full length or fragmented CCL22 with one or more mutations and/or one or more sequence deletions and/or additions introduced ex vivo.

Accordingly, in a specific embodiment the immunogenically active peptide fragment of the invention consists of at the most 90 consecutive amino acid residues, such as of the most 80 consecutive amino acids residues, for example at the most 70 consecutive amino acid residues, such as at the most 60 consecutive amino acid residues, for example at the most 50 consecutive amino acid residues, for example at the most 45 consecutive amino acid residues, such as at the most 40 consecutive amino acid residues, for example at the most 35 consecutive amino acid residues, such as at the most 30 consecutive amino acid residues, for example at the most 25 consecutive amino acid residues, such as 18 to 25 consecutive amino acids of CCL22 as identified in SEQ ID NO: 12 or SEQ ID NO: 15 or a functional homologue thereof; the functional homologue being a polypeptide of identical sequence except that at the most three amino acids have been substituted, such as at the most two amino acids have been substituted, such as at the most one amino acid has been substituted. Said immunogenically active peptide fragment may also consists of at the most 80 consecutive amino acids residues, for example at the most 70 consecutive amino acid residues, such as at the most 60 consecutive amino acid residues, for example at the most 50 consecutive amino acid residues, for example at the most 45 consecutive amino acid residues, such as at the most 40 consecutive amino acid residues, for example at the most 35 consecutive amino acid residues, such as at the most 30 consecutive amino acid residues, for example at the most 25 consecutive amino acid residues, such as 18 to 25 consecutive amino acids of CCL22 as identified in SEQ ID NO: 12 or SEQ ID NO: 15, wherein one or more amino acids have been mutated to another amino acid or deleted.

In one preferred embodiment of the invention, the immunogenically active peptide fragment consists of in the range of 18 to 25 amino acids, preferably of 22 consecutive amino acids of CCL22 as identified in SEQ ID NO: 12 or SEQ ID NO: 15 or a functional homologue thereof; the functional homologue being a polypeptide of identical sequence except that at the most three amino acids have been substituted, such as at the most two amino acids have been substituted, such as at the most one amino acid has been substituted.

Accordingly in another specific embodiment the immunogenically active peptide fragment of the invention consists of at the most 25 amino acid residues, such as at the most 24 amino acid residues, such as at the most 23 amino acid residues, such as at the most 22 amino acid residues, such as at the most 21 amino acid residues, such as at the most 20 amino acid residues, for example at the most 19 amino acid residues, such as at the most 18 amino acid residues, for example at the most 17 amino acid residues, such as at the most 16 amino acid residues, for example at the most 15 amino acid residues, such as at the most 14 amino acid residues, for example at the most 13 amino acid residues, such as at the most 12 amino acid residues, for example at the most 11 amino acid residues, such as 8 to 10 consecutive amino acids from CCL22 of SEQ ID NO: 12 or SEQ ID NO: 15 or a functional homologue thereof; the functional homologue being a polypeptide of identical sequence except that at the most three amino acids have been substituted, such as at the most two amino acids have been substituted, such as at the most one amino acid has been substituted.

In one preferred embodiment of the invention, the immunogenically active peptide comprises at the most 10 consecutive amino acid residues from CCL22, such as at the most 9 consecutive amino acid residues, such as 8 consecutive amino acid residues, such as 7 consecutive amino acid residues from CCL22 as identified in SEQ ID NO: 12 or SEQ ID NO: 15 or a functional homologue thereof; the functional homologue being a polypeptide of identical sequence except that at the most three amino acids have been substituted, such as at the most two amino acids have been substituted, such as at the most one amino acid has been substituted. In particular, the immunogenically active peptide may consist of 10 consecutive amino acid residues from CCL22 of SEQ ID NO: 12 or SEQ ID NO: 15 or the immunogenically active peptide may consist of 9 consecutive amino acid residues from CCL22 of SEQ ID NO: 12 or SEQ ID NO: 15.

In another preferred embodiment of the invention, the immunogenically active peptide comprises at the most 11 consecutive amino acid residues from the CCL22 peptide fragment of SEQ ID NO: 1, such as at the most 10 consecutive amino acid residues, such as at the most 9 consecutive amino acid residues, such as 8 consecutive amino acid residues, such as 7 consecutive amino acid residues from the CCL22 peptide fragment as identified in SEQ ID NO: 1 or a functional homologue thereof; the functional homologue being a polypeptide of identical sequence except that at the most three amino acids have been substituted, such as at the most two amino acids have been substituted, such as at the most one amino acid has been substituted. In particular, the immunogenically active peptide may consist of 10 consecutive amino acid residues from the CCL22 peptide fragment of SEQ ID NO: 1 or the immunogenically active peptide may consist of 9 consecutive amino acid residues from the CCL22 peptide fragment of SEQ ID NO: 1.

In particular, the immunogenically active peptide may consist of 10 consecutive amino acid residues from the CCL22 peptide fragment of SEQ ID NO: 3 or the immunogenically active peptide may consist of 9 consecutive amino acid residues from the CCL22 peptide fragment of SEQ ID NO: 3.

In another preferred embodiment of the invention, the immunogenically active peptide comprises at the most 11 consecutive amino acid residues from the CCL22 peptide fragment of SEQ ID NO: 4, such as at the most 10 consecutive amino acid residues, such as at the most 9 consecutive amino acid residues, such as 8 consecutive amino acid residues, such as 7 consecutive amino acid residues from the CCL22 peptide fragment as identified in SEQ ID NO: 4 or a functional homologue thereof; the functional homologue being a polypeptide of identical sequence except that at the most three amino acids have been substituted, such as at the most two amino acids have been substituted, such as at the most one amino acid has been substituted. In particular, the immunogenically active peptide may consist of 10 consecutive amino acid residues from the CCL22 peptide fragment of SEQ ID NO: 4 or the immunogenically active peptide may consist of 9 consecutive amino acid residues from the CCL22 peptide fragment of SEQ ID NO: 4.

In another preferred embodiment of the invention, the immunogenically active peptide comprises at the most 11 consecutive amino acid residues from the CCL22 peptide fragment of SEQ ID NO: 11, such as at the most 10 consecutive amino acid residues, such as at the most 9 consecutive amino acid residues, such as 8 consecutive amino acid residues, such as 7 consecutive amino acid residues from the CCL22 peptide fragment as identified in SEQ ID NO: 11 or a functional homologue thereof; the functional homologue being a polypeptide of identical sequence except that at the most three amino acids have been substituted, such as at the most two amino acids have been substituted, such as at the most one amino acid has been substituted. In particular, the immunogenically active peptide may consist of 10 consecutive amino acid residues from the CCL22 peptide fragment of SEQ ID NO: 11 or the immunogenically active peptide may consist of 9 consecutive amino acid residues from the CCL22 peptide fragment of SEQ ID NO: 11.

In some embodiments, the immunogenically active peptide fragment comprises or consists of VXLVLLAVAY (SEQ ID NO: 16), in particular the peptide fragment may comprise or consist of SEQ ID NO: 16, where X is a valine residue or an alanine residue and Y is a leucine residue or an isoleucine residue. Thus in some embodiments, the immunogenically active peptide comprises at the most 11 consecutive amino acid residues which comprise SEQ ID NO: 16, such as at the most 10 consecutive amino acid residues consisting of SEQ ID NO: 16.

In some embodiments of the invention the immunogenically active peptide may be selected from the group consisting of peptides listed in Table 1 or a functional homologue thereof; the functional homologue being a polypeptide of identical sequence except that at the most three amino acids have been substituted, such as at the most two amino acids have been substituted, such as at the most one amino acid has been substituted.

In some embodiments of the invention the immunogenically active peptide may be selected from the group consisting of peptides listed in Table 1 or a functional homologue thereof, the functional homologue being a polypeptide of at least 70% sequence identity therewith, such as at least 75% sequence identity, such as at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity therewith.

Accordingly, in a preferred embodiment, the immunogenically active peptide may be the CCL22 peptide fragment of SEQ ID NO: 1 or a functional homologue thereof, the functional homologue being a polypeptide of at least 70% sequence identity therewith, such as at least 75% sequence identity, such as at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity therewith.

In another preferred embodiment, the immunogenically active peptide may be the CCL22 peptide fragment of SEQ ID NO: 3 or a functional homologue thereof, the functional homologue being a polypeptide of at least 70% sequence identity therewith, such as at least 75% sequence identity, such as at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity therewith.

In another preferred embodiment, the immunogenically active peptide may be the CCL22 peptide fragment of SEQ ID NO: 4 or a functional homologue thereof, the functional homologue being a polypeptide of at least 70% sequence identity therewith, such as at least 75% sequence identity, such as at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity therewith.

In another preferred embodiment, the immunogenically active peptide may be the CCL22 peptide fragment of SEQ ID NO: 11 or a functional homologue thereof, the functional homologue being a polypeptide of at least 70% sequence identity therewith, such as at least 75% sequence identity, such as at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity therewith.

In another preferred embodiment, the immunogenically active peptide may be the CCL22 peptide fragment of SEQ ID NO: 13 or a functional homologue thereof, the functional homologue being a polypeptide of at least 70% sequence identity therewith, such as at least 75% sequence identity, such as at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity therewith.

In another preferred embodiment, the immunogenically active peptide may be the CCL22 peptide fragment of SEQ ID NO: 14 or a functional homologue thereof, the functional homologue being a polypeptide of at least 70% sequence identity therewith, such as at least 75% sequence identity, such as at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity therewith.

In another preferred embodiment, the immunogenically active peptide may be the CCL22 peptide fragment of SEQ ID NO: 16 or a functional homologue thereof, the functional homologue being a polypeptide of at least 70% sequence identity therewith, such as at least 75% sequence identity, such as at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity therewith.

TABLE 1

Useful CCL22 peptides

| SEQ ID NO | Name | Amino acid numbers in SEQ ID NO: 1 | Sequence |
|---|---|---|---|
| SEQ ID NO: 1 | CCL22LONG | $CCL22_{1-22}$ | MDRLQTALLVVLVLLAVALQAT |
| SEQ ID NO: 2 | CCL22-1 | $CCL22_{7-15}$ | ALLVVLVLL |
| SEQ ID NO: 3 | CCL22-2 | $CCL22_{3-11}$ | RLQTALLVV |
| SEQ ID NO: 4 | CCL22-3 | $CCL22_{3-12}$ | RLQTALLVVL |
| SEQ ID NO: 5 | CCL22-4 | $CCL22_{11-19}$ | VLVLLAVAL |
| SEQ ID NO: 6 | CCL22-5 | $CCL22_{5-13}$ | QTALLVVLV |
| SEQ ID NO: 7 | CCL22-6 | $CCL22_{14-22}$ | LLAVALQAT |
| SEQ ID NO: 8 | CCL22-7 | $CCL22_{8-17}$ | LLVVLVLLAV |

TABLE 1-continued

Useful CCL22 peptides

| SEQ ID NO: 9 | CCL22-8 | CCL22$_{9-17}$ | LVVLVLLAV |
|---|---|---|---|
| SEQ ID NO: 10 | CCL22-9 | CCL22$_{6-15}$ | TALLVVLVL |
| SEQ ID NO: 11 | CCL22SIGNAL | CCL22$_{1-24}$ | MDRLQTALLVVLVL LAVALQATEA |

| SEQ ID NO | Name | Amino acid numbers in SEQ ID NO: 15 | Sequence |
|---|---|---|---|
| SEQ ID NO: 13 | mCCL22long | mCCL22$_{1-22}$ | MATLRVPLLVALVLLAVAIQTS |
| SEQ ID NO: 14 | mCCL22short | mCCL22$_{10-19}$ | VALVLLAVAI |
| SEQ ID NO: 16 | Consensus sequence | | VXLVLLAVAY |

In a preferred embodiment of the invention the immunogenically active peptide is selected from the group consisting of:
a) SEQ ID NO: 1 (CCL22$_{1-22}$);
b) SEQ ID NO:3 (CCL22$_{3-11}$);
c) SEQ ID NO: 4 (CCL22$_{3-12}$);
d) SEQ ID NO: 11 (CCL22$_{1-24}$);
e) SEQ ID NO: 14 (mCCL22$_{10-19}$) and
f) a functional homologue of the polypeptide according to any of a) to d); the functional homologue being a polypeptide of identical sequence except that at the most three amino acids have been substituted, such as at the most two amino acids have been substituted, such as at the most one amino acid has been substituted.

Other peptides of the invention comprise (or more preferably consist of) between 4 and 90, preferably between 5 and 80, more preferably between 10 and 70, yet more preferably between 12 and 60, even more preferably between 15 and 40, such as between 18 and 25 contiguous amino acids of CCL22 of SEQ ID NO: 12 or SEQ ID NO: 15 or a functional homologue thereof having at least 70%, preferably at least 80%, more preferably at least 90%, even more preferably at least 95%, yet more preferably at least 98%, for example at least 99% sequence identity to SEQ ID NO: 12 or SEQ ID NO: 15.

Functional Homologues

Functional homologues of CCL22 or immunogenically active fragments thereof, are polypeptides, which also are immunogenically active, and which shares at least some degree of sequence identity with CCL22, and in particular with CCL22 of SEQ ID NO: 12 or SEQ ID NO: 15.

For shorter polypeptides, such as for polypeptide shorter than 50 amino acids, for example shorter than 25 amino acids, then functional homologue may be an immunogenically active polypeptide of identical sequence except that at the most three amino acids have been substituted, such as at the most two amino acids have been substituted, such as at the most one amino acid has been substituted.

Alternatively, a functional homologue may be an immunogenically active polypeptide sharing at least 70% sequence identity to CCL22 of SEQ ID NO: 12 or SEQ ID NO: 15, and accordingly, a functional homologue preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with human CCL22 of SEQ ID NO: 12 or SEQ ID NO: 15.

In a preferred embodiment, a functional homologue is an immunogenically active polypeptide sharing at least 70% sequence identity to the CCL22 peptide fragment of SEQ ID NO: 1, and accordingly, a functional homologue preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the CCL22 peptide fragment of SEQ ID NO: 1.

In a preferred embodiment, a functional homologue is an immunogenically active polypeptide sharing at least 70% sequence identity to the CCL22 peptide fragment of SEQ ID NO: 3, and accordingly, a functional homologue preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the CCL22 peptide fragment of SEQ ID NO: 3.

In another preferred embodiment, a functional homologue is an immunogenically active polypeptide sharing at least 70% sequence identity to the CCL22 peptide fragment of SEQ ID NO: 4, and accordingly, a functional homologue preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the CCL22 peptide fragment of SEQ ID NO: 4.

In another preferred embodiment, a functional homologue is an immunogenically active polypeptide sharing at least 70% sequence identity to the CCL22 peptide fragment of SEQ ID NO: 11, and accordingly, a functional homologue preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the CCL22 peptide fragment of SEQ ID NO: 11.

In another preferred embodiment, a functional homologue is an immunogenically active polypeptide sharing at least 70% sequence identity to the CCL22 peptide fragment of SEQ ID NO: 13, and accordingly, a functional homologue preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the CCL22 peptide fragment of SEQ ID NO: 13.

In another preferred embodiment, a functional homologue is an immunogenically active polypeptide sharing at least 70% sequence identity to the CCL22 peptide fragment of SEQ ID NO: 14, and accordingly, a functional homologue preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the CCL22 peptide fragment of SEQ ID NO: 14.

In another preferred embodiment, a functional homologue is an immunogenically active polypeptide sharing at least 70% sequence identity to the CCL22 peptide fragment of SEQ ID NO: 16, and accordingly, a functional homologue preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the CCL22 peptide fragment of SEQ ID NO: 16.

In some embodiments, a functional homologue is an immunogenically active polypeptide differing from the CCL22 peptide fragment of SEQ ID NO: 1 by at least one amino acid, such as at least two amino acids, such as at least three amino acids.

In some embodiments, a functional homologue is an immunogenically active polypeptide differing from the CCL22 peptide fragment of SEQ ID NO: 3 by at least one amino acid, such as at least two amino acids, such as at least three amino acids.

In another embodiment, a functional homologue is an immunogenically active polypeptide differing from the CCL22 peptide fragment of SEQ ID NO: 4 by at least one amino acid, such as at least two amino acids, such as at least three amino acids.

In another embodiment, a functional homologue is an immunogenically active polypeptide differing from the CCL22 peptide fragment of SEQ ID NO: 11 by at least one amino acid, such as at least two amino acids, such as at least three amino acids.

In some embodiments, a functional homologue is an immunogenically active polypeptide differing from the CCL22 peptide fragment of SEQ ID NO: 14 by at least one amino acid, such as at least two amino acids, such as at least three amino acids.

In some embodiments, a functional homologue is an immunogenically active polypeptide differing from the CCL22 peptide fragment of SEQ ID NO: 14 by at least one amino acid, such as at least two amino acids, such as at least three amino acids.

In some embodiments, a functional homologue is an immunogenically active polypeptide differing from the CCL22 peptide fragment of SEQ ID NO: 16 by at least one amino acid, such as at least two amino acids, such as at least three amino acids.

Sequence identity can be calculated using a number of well-known algorithms and applying a number of different gap penalties. The sequence identity is calculated relative to full-length reference sequence, e.g. to full length SEQ ID NO: 1. Any sequence alignment tool, such as but not limited to FASTA, BLAST, or LALIGN may be used for searching homologues and calculating sequence identity. Moreover, when appropriate any commonly known substitution matrix, such as but not limited to PAM, BLOSSUM or PSSM matrices may be applied with the search algorithm. For example, a PSSM (position specific scoring matrix) may be applied via the PSI-BLAST program. Moreover, sequence alignments may be performed using a range of penalties for gap opening and extension. For example, the BLAST algorithm may be used with a gap opening penalty in the range 5-12, and a gap extension penalty in the range 1-2.

Functional homologues may further comprise chemical modifications such as ubiquitination, labeling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins, however it is preferred that the functional equivalent does not contain chemical modifications.

Any changes made to the sequence of amino acid residues compared to that of CCL22 of SEQ ID NO: 12 or SEQ ID NO: 15, or compared to the CCL22 fragments of SEQ ID NO: 1, SEQ ID NO: 3, SEQ ID NO: 4, SEQ ID NO: 11, SEQ ID NO: 13 or SEQ ID NO: 14 are preferably conservative substitutions. A person skilled in the art will know how to make and assess 'conservative' amino acid substitutions, by which one amino acid is substituted for another with one or more shared chemical and/or physical characteristics. Conservative amino acid substitutions are less likely to affect the functionality of the protein. Amino acids may be grouped according to shared characteristics. A conservative amino acid substitution is a substitution of one amino acid within a predetermined group of amino acids for another amino acid within the same group, wherein the amino acids within a predetermined groups exhibit similar or substantially similar characteristics.

Thus, in an embodiment of the present invention, the vaccine composition comprises a polypeptide consisting of a consecutive sequence of CCL22 of SEQ ID NO: 12 or SEQ ID NO: 15 in the range of 8 to 50 amino acids, preferably in the range of 8 to 10 or 20 to 25 amino acids, wherein at the most three amino acids have been substituted, and where the substitution preferably is conservative.

Polypeptides Comprising CCL22 or a Fragment Thereof

It is also comprised within the invention that the vaccine compositions of the invention may comprise a polypeptide comprising either CCL22 or a fragment thereof. Thus, the immunogenically active peptide fragment of CCL22 may be a polypeptide comprising a CCL22 fragment, for example any of the polypeptides described herein in this section.

In particular, such polypeptides may comprise full length CCL22, such as any of the CCL22s described herein above in the section "C-C motif chemokine 22". For example the polypeptide may comprise CCL22 of SEQ ID NO: 12 or SEQ ID NO: 15 or a functional homologue thereof sharing at least 70%, such as at least 80%, for example at least 90%, such as at least 95% sequence identity therewith. In particular, such polypeptides may comprise at the most 90, such as at the most 50, for example at the most 25, such as at the most 10 amino acids in addition to CCL22 of SEQ ID NO: 12 or SEQ ID NO: 15.

It is also comprised within the invention that the vaccine compositions may comprise a polypeptide comprising a fragment of CCL22, such as any of the fragments described herein above in the section "Immunogenically active peptide fragment of CCL22". Said polypeptide may also comprise any of the immunogenically active peptide fragments of CCL22, which is an MHC Class I-restricted peptide fragment or MHC Class II-restricted peptide fragment, such as any of the an MHC Class I-restricted peptide fragments or MHC Class II-restricted peptide fragments described in the section "MHC".

Thus, said polypeptide may be a polypeptide of at the most 400 amino acids, such as at the most 300 amino acids, for example at the most 200 amino acids, such as at the most 100 amino acids, for example at the most 50 amino acids comprising a consecutive sequence of amino acids of SEQ ID NO: 12 or SEQ ID NO: 15, wherein said consecutive sequence of amino acids of SEQ ID NO:12 or SEQ ID NO: 15 consists of at the most 50 amino acid residues, for example at the most 45 amino acid residues, such as at the most 40 amino acid residues, for example at the most 35 amino acid residues, such as at the most 30 amino acid residues, for example at the most 25 amino acid residues, such as in the range of 18 to 25, such as in the range of 8 to 10 consecutive amino acids from CCL22 of SEQ ID NO: 12 or SEQ ID NO: 15 or a functional homologue thereof.

In particular, said polypeptide may be a polypeptide of at the most 100 consecutive amino acid residues, such as at the most 90 consecutive amino acid residues, such as at the most 80 consecutive amino acid residues, for example at the most 70 consecutive amino acid residues, such as at the most 60 consecutive amino acid residues, for example at the most 50 consecutive amino acid residues, for example at the most 45 consecutive amino acid residues, such as at the most 40 consecutive amino acid residues, for example at the most 35 consecutive amino acid residues, such as at the most 30 consecutive amino acid residues, for example at the most 25 consecutive amino acid residues, such as 18 to 25 consecutive amino acid residues, such as of 20 consecutive amino acids of CCL22 as identified in SEQ ID NO: 12 or SEQ ID NO: 15 or a functional homologue thereof, and comprising an immunogenically active peptide selected from the group consisting of:

a) SEQ ID NO: 1 (CCL22$_{1-22}$);
b) SEQ ID NO:3 (CCL22$_{3-11}$);
c) SEQ ID NO: 4 (CCL22$_{3-12}$);
d) SEQ ID NO: 11 (CCL22$_{1-24}$);
e) SEQ ID NO: 14 (mCCL22$_{10-19}$);
f) any of the sequences mentioned in Table 1; and
g) a functional homologue of the polypeptide according to any of a) to d); the functional homologue being a polypeptide of identical sequence except that at the most three amino acids have been substituted, such as at the most two amino acids have been substituted, such as at the most one amino acid has been substituted.

In some embodiments, the immunogenically active peptide comprises a sequence as set forth in SEQ ID NO: 16, i.e. has the sequence VXLVLLAVAY (SEQ ID NO: 16), where X is selected from the group consisting of valine and alanine, and Y is selected from the group consisting of isoleucine and leucine.

Said polypeptide may also be a polypeptide of at the most 100 amino acids, such as at the most 50 amino acids, for example at the most 30 amino acids, such as at the most 20 amino acids, for example at the most 15 amino acids comprising a consecutive sequence of amino acids of SEQ ID NO: 12 or SEQ ID NO: 15, wherein said consecutive sequence of amino acids of SEQ ID NO: 12 or SEQ ID NO: 15 consists of in the range of 8 to 10, such as of 9 or 10 consecutive amino acids from CCL22 of SEQ ID NO: 12 or SEQ ID NO: 15 or a functional homologue thereof. Thus, said polypeptide may be a polypeptide of at the most 100 amino acids, such as at the most 50 amino acids, for example at the most 30 amino acids, such as at the most 20 amino acids, for example at the most 15 amino acids comprising an immunogenically active peptide selected from the group consisting of:

a) SEQ ID NO: 1 (CCL22$_{1-22}$);
b) SEQ ID NO: 3 (CCL22$_{3-11}$);
c) SEQ ID NO: 4 (CCL22$_{3-12}$);
d) SEQ ID NO: 11 (CCL22$_{1-24}$);
e) SEQ ID NO: 14 (mCCL22$_{10-19}$)
f) any of the sequences mentioned in Table 1; and
g) a functional homologue of the polypeptide according to any of a) to c); the functional homologue being a polypeptide of identical sequence except that at the most three amino acids have been substituted, such as at the most two amino acids have been substituted, such as at the most one amino acid has been substituted.

In some embodiments, the immunogenically active peptide consist of at the most 100 amino acids, such as at the most 50 amino acids, for example at the most 30 amino acids, such as at the most 20 amino acids, for example at the most 15 amino acids comprising the sequence of amino acids of VXLVLLAVAY (SEQ ID NO: 16). In particular, said polypeptide may be a polypeptide of at the most 100 consecutive amino acid residues, such as at the most 90 consecutive amino acid residues, such as at the most 80 consecutive amino acid residues, for example at the most 70 consecutive amino acid residues, such as at the most 60 consecutive amino acid residues, for example at the most 50 consecutive amino acid residues, for example at the most 45 consecutive amino acid residues, such as at the most 40 consecutive amino acid residues, for example at the most 35 consecutive amino acid residues, such as at the most 30 consecutive amino acid residues, for example at the most 25 consecutive amino acid residues, such as 18 to 25 consecutive amino acid residues, such as of 20 consecutive amino acids of CCL22 as identified in SEQ ID NO: 12 or SEQ ID NO: 15 or a functional homologue thereof, wherein said consecutive sequence comprises VXLVLLAVAY (SEQ ID NO: 16). It is preferred that within SEQ ID NO:16, X is selected from the group consisting of valine and alanine, and Y is selected from the group consisting of isoleucine and leucine
MHC It is comprised within the invention that the immunogenically active peptide fragments of CCL22 may be an MHC Class I-restricted peptide fragment or MHC Class II-restricted peptide fragment, such as any of the an MHC Class I-restricted peptide fragments or MHC Class II-restricted peptide fragments described in this section.

There are two types of MHC molecules; MHC class I molecules and MHC class II molecules. MHC class I molecules are recognized by CD8 T-cells, which are the principal effector cells of the adaptive immune response. MHC class II molecules are mainly expressed on the surface of antigen presenting cells (APCs), the most important of which appears to be the dendritic cells. APCs stimulate naïve T-cells, as well as other cells in the immune system. They stimulate both CD8 T-cells and CD4 T-cells.

In one embodiment, the invention provides immunogenically active CCL22 peptides (optionally comprised in larger peptides and/or in vaccine compositions), wherein said immunogenically active CCL2 peptides are MHC Class I-restricted peptide fragments consisting of 8-10 consecutive amino acids from CCL22 of SEQ ID NO: 12 or SEQ ID NO: 15, such as the peptide fragment of SEQ ID NO: 1, SEQ ID NO: 3, SEQ ID NO: 4, SEQ ID NO: 11, SEQ ID NO: 13 or SEQ ID NO: 14 or a functional homologue thereof, wherein at the most two amino acids of SEQ ID NO: 12 or SEQ ID NO: 1, SEQ ID NO: 3, SEQ ID NO: 4 or SEQ ID NO: 11 or SEQ ID NO: 13 or SEQ ID NO: 14 or SEQ ID NO: 16 have been substituted, which are characterized by having at least one of several features, one of which is the ability to bind to the Class I HLA molecule to which it is restricted at an affinity as measured by the amount of the peptide that is capable of half maximal recovery of the Class I HLA molecule ($C_{50}$ value) which is at the most 50 µM as determined by the assembly binding assay as described herein. This assembly assay is based on stabilization of the HLA molecule after loading of peptide to the peptide transporter deficient cell line T2. Subsequently, correctly folded stable HLA heavy chains are immunoprecipitated using conformation dependent antibodies and the peptide binding is quantitated. The peptides of this embodiment comprises (or more preferably consists of) at the most 100, preferably at the most 50, more preferably at the most 25, yet more preferably at the most 20, yet even more preferably at the most 15, such as at the most 10, for example in the range of 8 to 10 consecutive amino acids of CCL22 of SEQ ID NO: 1, SEQ ID NO: 3, SEQ ID NO: 4, SEQ ID NO: 11, SEQ ID NO: 13 or SEQ ID NO: 14 or a functional homologue thereof wherein at the most two amino acids of SEQ ID NO: 12 or SEQ ID NO: 15 have been substituted.

This assay provides a simple means of screening candidate peptides for their ability to bind to a given HLA allele molecule at the above affinity. In preferred embodiments, the peptide fragment of the invention in one having a $C_{50}$ value, which is at the most 30 µM, such as a $C_{50}$ value, which is at the most 20 µM including $C_{50}$ values of at the most 10 µM, at the most 5 µM and at the most 2 µM.

In another preferred embodiment, there are provided novel MHC Class II-restricted peptide fragments of CCL22 of SEQ ID NO: 12 or SEQ ID NO: 15, such as the peptides of SEQ ID NO: 1, SEQ ID NO: 3, SEQ ID NO: 4, SEQ ID NO: 11, SEQ ID NO: 13 or SEQ ID NO: 14 or functional homologues thereof, wherein at the most two amino acids of SEQ ID NO: 12 or SEQ ID NO: 15 have been substituted (also referred to herein as "peptides"), which are characterized by having at least one of several features described herein below. The peptides of this embodiment comprise (or more preferably consist of) between 4 and 93, preferably between 8 and 90, more preferably between 10 and 75, yet more preferably between 12 and 60, even more preferably between 15 and 40, such as between 18 and 25 consecutive amino acids of CCL22 of SEQ ID NO: 12 or SEQ ID NO: 15 or a functional homologue thereof, wherein at the most two, preferably at the most one amino acids of SEQ ID NO: 12 or SEQ ID NO: 15 have been substituted. In a preferred embodiment, the peptides comprise (or more preferably consist of) between 4 and 15, preferably between 5 and 14, more preferably between 6 and 13, yet more preferably between 7 and 12, even more preferably between 8 and 11, such as between 8 and 10, such as 9 consecutive amino acids of the CCL22 peptide fragment of SEQ ID NO: 1. In another preferred embodiment, the peptides comprise (or more preferably consist of) between 4 and 9, preferably between 5 and 9, more preferably between 6 and 9, yet more preferably between 7 and 8, such as 8 or 9 consecutive amino acids of the CCL22 peptide fragment of SEQ ID NO: 3. In another preferred embodiment, the peptides comprise (or more preferably consist of) between 4 and 10, preferably between 5 and 10, more preferably between 6 and 10, yet more preferably between 7 and 9, such as 9 or 10 consecutive amino acids of the CCL22 peptide fragment of SEQ ID NO: 4. In yet another preferred embodiment, the peptides comprise (or more preferably consist of) between 4 and 15, preferably between 5 and 14, more preferably between 6 and 13, yet more preferably between 7 and 12, even more preferably between 8 and 11, such as between 8 and 10, such as 9 consecutive amino acids of the CCL22 peptide fragment of SEQ ID NO: 11. In a preferred embodiment, the peptides comprise (or more preferably consist of) between 4 and 15, preferably between 5 and 14, more preferably between 6 and 13, yet more preferably between 7 and 12, even more preferably between 8 and 11, such as between 8 and 10, such as 9 consecutive amino acids of the CCL22 peptide fragment of SEQ ID NO: 13. In yet another preferred embodiment, the peptides comprise (or more preferably consist of) between 4 and 10, preferably between 5 and 10, more preferably between 6 and 10, yet more preferably between 7 and 10, such as 8 or 9 consecutive amino acids of the CCL22 peptide fragment of SEQ ID NO: 14. In yet another preferred embodiment, the peptides comprise (or more preferably consist of) between 4 and 10, preferably between 5 and 10, more preferably between 6 and 10, yet more preferably between 7 and 10, such as 8 or 9 consecutive amino acids of the CCL22 peptide fragment of SEQ ID NO: 16.

Thus there are provided novel MHC Class I-restricted peptide fragments of 8-10 amino acids or novel MHC Class II-restricted peptide fragments of 18-25 amino acids of CCL22 of SEQ ID NO: 12 or SEQ ID NO: 15 or a functional homologue thereof, wherein at the most two amino acids of SEQ ID NO: 12 or SEQ ID NO: 15 have been substituted, which are characterized by having at least one of several features described herein below, one of which is the ability to bind to the Class I or Class II HLA molecule to which it is restricted.

In particular embodiments there is provided a peptide fragment, which is an MHC Class I-restricted peptide or an MHC class II-restricted peptide having at least one of the following characteristics:
(i) capable of eliciting INF-γ-producing cells in a PBL population of at least one cancer patient at a frequency of at least 1 per $10^4$ PBLs as determined by an ELISPOT assay, and/or
(ii) capable of in situ detection in a tumor tissue of CTLs that are reactive with the epitope peptide.
(iii) capable of inducing the growth of CCL22 specific T-cells in vitro.

More preferred peptides according to the present invention are peptides capable of raising a specific T-cell response as determined by an ELISPOT assay, for example the ELISPOT assay described in Example 1 herein below. Some peptides although they do not bind MHC class I or class II with high affinity, may still give rise to a T-cell response as determined by ELISPOT. Other peptides capable of binding MHC class I or class II with high affinity also give rise to a T-cell response as determined by ELISPOT. Both kinds of peptides are preferred peptides according to the invention.

Hence, preferred peptides according to the present invention are peptides capable of raising a specific T-cell response as measured by an ELISPOT assay, wherein more than 50 peptide specific spots per $10^8$ cells, more preferably per $10^7$, even more preferably per $10^6$, yet more preferably per $10^5$ cells, such as per $10^4$ cells are measured.

Most preferred peptides according to the present invention are peptides that are capable of eliciting a cellular immune response in an individual suffering from a clinical condition characterized by the expression of CCL22, the clinical condition preferably being a cancer or infection, and most preferably a cancer.

As described above, the HLA system represents the human major histocompatibility (MHC) system. Generally, MHC systems control a range of characteristics: transplantation antigens, thymus dependent immune responses, certain complement factors and predisposition for certain diseases. More specifically, the MHC codes for three different types of molecules, i.e. Class I, II and III molecules, which determine the more general characteristics of the MHC. Of these molecules, the Class I molecules are so-called HLA-A, HLA-B and HLA-C molecules that are presented on the surface of most nucleated cells and thrombocytes.

The peptides of the present invention are characterized by their ability to bind to (being restricted by) a particular MHC Class I HLA molecule. Thus, in one embodiment the peptide is one which is restricted by a MHC Class I HLA-A molecule including HLA-A1, HLA-A2, HLA-A3, HLA-A9, HLA-A10, HLA-A11, HLA-Aw19, HLA-A23(9), HLA-A24(9), HLA-A25(10), HLA-A26(10), HLA-A28, HLA-A29(w19), HLA-A30(w19), HLA-A31(w19), HLA-A32 (w19), HLA-Aw33(w19), HLA-Aw34(10), HLA-Aw36, HLA-Aw43, HLA-Aw66(10), HLA-Aw68(28), HLA-A69 (28). More simple designations are also used throughout the literature, where only the primary numeric designation is used, e.g. HLA-A19 or HLA-A24 instead of HLA-Aw19 and HLA-A24(49), respectively. In specific embodiments, the peptide of the invention is restricted a MHC Class I HLA species selected from the group consisting of HLA-A1, HLA-A2, HLA-A3, HLA-A11 and HLA-A24. In specific embodiment, the peptide of the invention is restricted a MHC Class I HLA species HLA-A2 or HLA-A3.

In further useful embodiments, the peptide of the invention is a peptide, which is restricted by a MHC Class I HLA-B molecule including any of the following: HLA-B5, HLA-B7, HLA-B8, HLA-B12, HLA-B13, HLA-B14, HLA-B15, HLA-B16, HLA-B17, HLA-B18, HLA-B21, HLA-Bw22, HLA-B27, HLA-B35, HLA-B37, HLA-B38, HLA-B39, HLA-B40, HLA-Bw41, HLA-Bw42, HLA-B44, HLA-B45, HLA-Bw46 and HLA-Bw47. In specific embodiments of the invention, the MHC Class I HLA-B species to which the peptide of the invention is capable of binding is selected from HLA-B7, HLA-B35, HLA-B44, HLA-B8, HLA-B15, HLA-B27 and HLA-B51.

In further useful embodiments, the peptide of the invention is a peptide, which is restricted by a MHC Class I HLA-C molecule including but not limited to any of the following: HLA-Cw1, HLA-Cw2, HLA-Cw3, HLA-Cw4, HLA-Cw5, HLA-Cw6, HLA-Cw7 and HLA-Cw1.

In further useful embodiments, the peptide of the invention is a peptide, which is restricted by a MHC Class II HLA molecule including but not limited to any of the following: HLA-DPA-1, HLA-DPB-1, HLA-DQA1, HLA-DQB1, HLA-DRA, HLA-DRB and all alleles in these groups and HLA-DM, HLA-DO.

The selection of peptides potentially having the ability to bind to a particular HLA molecule can be made by the alignment of known sequences that bind to a given particular HLA molecule to thereby reveal the predominance of a few related amino acids at particular positions in the peptides. Such predominant amino acid residues are also referred to herein as "anchor residues" or "anchor residue motifs". By following such a relatively simple procedure based on known sequence data that can be found in accessible databases, peptides can be derived from CCL22, which are likely to bind to a specific HLA molecule. Representative examples of such analyses for a range of HLA molecules are given in the below table:

TABLE 2

| HLA allele | Position 1 | Position 2 | Position 3 | Position 5 | Position 6 | Position 7 | C-terminal |
|---|---|---|---|---|---|---|---|
| HLA-A1 |  | T, S | D, E |  |  | L | Y |
| HLA-A2 |  | L, M |  |  | V |  | L, V |
| HLA-A3 |  | L, V, M | F, Y |  |  |  | K, Y, F |
| HLA-A11 |  | V, I, F, Y | M, L, F, Y, I |  |  |  | K, R |
| HLA-A23 |  | I, Y |  |  |  |  | W, I |
| HLA-A24 |  | Y |  | I, V | F |  | I, L, F |
| HLA-A25 |  | M, A, T | I |  |  |  | W |
| HLA-A26 | E, D | V, T, I, L, F |  |  | I, L, V |  | Y, F |
| HLA-A28 | E, D | V, A, L |  |  |  |  | A, R |
| HLA-A29 |  | E |  |  |  |  | Y, L |
| HLA-A30 |  | Y, L, F, V |  |  |  |  | Y |
| HLA-A31 |  |  | L, M, F, Y |  |  |  | R |
| HLA-A32 |  | I, L |  |  |  |  | W |

TABLE 2-continued

| HLA allele | Position 1 | Position 2 | Position 3 | Position 5 | Position 6 | Position 7 | C-terminal |
|---|---|---|---|---|---|---|---|
| HLA-A33 | | Y, I, L, V | | | | | R |
| HLA-A34 | | V, L | | | | | R |
| HLA-A66 | E, D | T, V | | | | | R, K |
| HLA-A68 | E, D | T, V | | | | | R, K |
| HLA-A69 | | V, T, A | | | | | V, L |
| HLA-A74 | | T | | | | | V, L |
| HLA-B5 | | A, P | F, Y | | | | I, L |
| HLA-B7 | | P | | | | | L, F |
| HLA-B8 | | | K | K, R | | | L |
| HLA-B14 | | R, K | | | | | L, V |
| HLA-B15 (B62) | | Q, L, K, P, H, V, I, M, S, T | | | | | F, Y, W |
| HLA-B17 | | | | | | | L, V |
| HLA-B27 | | R | | | | | Y, K, F, L |
| HLA-B35 | | P | | | | | I, L, M, Y |
| HLA-B37 | | D, E | | | | | I, L, M |
| HLA-B38 | | H | D, E | | | | F, L |
| HLA-B39 | | R, H | | | | | L, F |
| HLA-B40 (B60, 61) | | E | F, I, V | | | | L, V, A, W, M, T, R |
| HLA-B42 | | L, P | | | | | Y, L |
| HLA-B44 | | E | | | | | F, Y, W |
| HLA-B46 | | M, I, L, V | | | | | Y, F |
| HLA-B48 | | Q, K | | | | | L |
| HLA-B51 | | A, P, G | | | | | F, Y, I, V |
| HLA-B52 | | Q | F, Y | | | | I, V |
| HLA-B53 | | P | | | | | W, F, L |
| HLA-B54 | | P | | | | | |
| HLA-B55 | | P | | | | | A, V |
| HLA-B56 | | P | | | | | A, V |
| HLA-B57 | | A, T, S | | | | | F, W, Y |
| HLA-B58 | | A, T, S | | | | | F, W, Y |
| HLA-B67 | | P | | | | | L |
| HLA-B73 | | R | | | | | P |
| HLA-Cw1 | | A, L | | | | | L |
| HLA-Cw2 | | A, L | | | | | F, Y |
| HLA-Cw3 | | A, L | | | | | L, M |
| HLA-Cw4 | | Y, P, F | | | | | L, M, F, Y |
| HLA-Cw6 | | | | | | | L, I, V, Y |
| HLA-Cw6 | | Y | | | | | L, Y, F |
| HLA-Cw8 | | Y | | | | | L, I, |
| HLA-Cw16 | | A, L | | | | | L, V |

* In one embodiment there is no specific anchor residue for this position, however in a preferred embodiment the anchor residue is R or A.

Thus, as an example, nonapeptides potentially having the ability to bind to HLA-A3 would have one of the following sequences: Xaa-L-Y-Xaa-Xaa-Xaa-Xaa-Xaa-K, Xaa-L-Y-Xaa-Xaa-Xaa-Xaa-Xaa-Y; Xaa-L-Y-Xaa-Xaa-Xaa-Xaa-F or Xaa-V-Y-Xaa-Xaa-Xaa-Xaa-Xaa-K (Xaa indicating any amino acid residue). In a similar manner, sequences potentially having the ability to bind to any other HLA molecule can be designed. It will be appreciated that the person of ordinary skill in the art will be able to identify further "anchor residue motifs" for a given HLA molecule.

The peptide of the invention may have a sequence which is a native sequence of the CCL22 from which is derived. However, peptides having a higher affinity to any given HLA molecule may be derived from such a native sequence by modifying the sequence by substituting, deleting or adding at least one amino acid residue, e.g. on the basis of the procedure described above, whereby anchor residue motifs in respect of the given HLA molecule are identified.

Thus, in useful embodiments, the polypeptides of the invention include peptides, the sequences of which comprise, for each of the specific HLA alleles listed in the table, any of the amino acid residues as indicated in the table.

Thus, the peptides of the invention may be any of the above-mentioned peptides comprising consecutive sequences from CCL22, wherein in the range of 1 to 10, preferably in the range of 1 to 5, more preferably in the range of 1 to 3, even more preferably in the range of 1 to 2, yet more preferably 1 amino acid has been exchanged for another amino acid, preferably in a manner so that the peptide comprises one or more, preferably all anchor residues of a given HLA-A specific peptide as indicated in the table above.

Examples of preferable HLA species, to which preferred peptides of the present invention are restricted include: a MHC Class I HLA species selected from the group consisting of HLA-A1, HLA-A2, HLA-A3, HLA-A11 and HLA-A24, more preferably the peptide is restricted by HLA-A3 or HLA-A2. Alternatively a preferred HLA species includes MHC Class I HLA-B species selected from the group consisting of HLA-B7, HLA-B35, HLA-B44, HLA-B8, HLA-B15, HLA-B27 and HLA-B51.

An approach to identifying polypeptides of the invention includes the following steps: selecting a particular HLA molecule, e.g. one occurring at a high rate in a given population, carrying out an alignment analysis as described above to identify "anchor residue motifs" in the CCL22 protein, isolating or constructing peptides of a suitable size that comprise one or more of the identified anchor residues and testing the resulting peptides for the capability of the peptides to elicit INF-γ-producing cells in a PBL population of a cancer patient at a frequency of at least 1 per $10^4$ PBLs as determined by an ELISPOT assay as described in Example 1. For example, the capability of the peptides to elicit INF-γ-producing cells in a PBMC population of a cancer patient has frequency of at least 1 per $10^4$ PBMCs.

In one aspect of the present invention, CCL22-derived peptides longer than 8 to 10 amino acid residues are provided. Polypeptides longer than 8 to 10 amino acids are processed by the proteasome to a shorter length for binding to HLA molecules. Thus, when administering a polypeptide longer than 8 to 10 amino acid residues long, the "long" polypeptide/protein/protein fragment/variant of CCL22 may be processed in vivo into a series of smaller peptides in the cytosol by the proteasome. An advantage of using a longer polypeptide that may be processed by the proteasome into a variety of different shorter peptides is that more HLA classes may be targeted with one peptide than one 8 to 10 amino acid peptide that is restricted to a particular HLA class.

Surprisingly, some of the peptides of the present invention bind to MHC molecules with an affinity sufficiently high to render substitutions unnecessary and are ready for use as antigens as they are presented here. Preferably, the vaccine composition of the present invention comprises one or more of the following: CCL22 protein (SEQ ID NO: 12 or SEQ ID NO: 15), polypeptide fragments here from, likewise variants, functional homologues of full length and partial length CCL22, contiguous peptides of CCL22 and functional homologues of these. More preferably, the vaccine composition comprises any of the sequences listed in Table 1. Very preferably, the vaccine composition comprises the peptides SEQ ID NO: 1 (CCL22$_{1-22}$), SEQ ID NO: 3 (CCL22$_{3-11}$) SEQ ID NO: 4 (CCL22$_{3-12}$), SEQ ID NO: 11 (CCL22$_{1-24}$), SEQ ID NO: 13 (mCCL22$_{1-22}$) or SEQ ID NO: 14 (mCCL22$_{1-24}$).

A significant feature of the peptide of the invention is its capability to recognize or elicit INF-γ-producing responder T cells, i.e. cytotoxic T cells (CTLs) that specifically recognize the particular peptide in a PBL population, on an APC or tumor/neoplastic cells of an individual suffering from a cancer and/or an infection (target cells). This activity is readily determined by subjecting PBLs, PBMCs, APCs or tumor cells from an individual to an ELISPOT assay. Prior to the assay, it may be advantageous to stimulate the cells to be assayed by contacting the cells with the peptide to be tested. Preferably, the peptide is capable of eliciting or recognizing INF-γ-producing T cells at a frequency of at least 1 per $10^4$ PBLs such as at a frequency of at least 1 per $10^4$ PBMCs as determined by an ELISPOT assay as used herein. More preferably the frequency is at least 5 per $10^4$ PBLs, most preferably at least 10 per $10^4$ PBLs, such as at least 50 or 100 per $10^4$ PBLs. For example, the frequency is at least 5 per $10^4$ PBMCs, most preferably at least 10 per $10^4$ PBMCs, such as at least 50 or 100 per $10^4$ PBMCs.

The ELISPOT assay represents a strong tool to monitor CCL22 peptide specific T-cell responses. A major implication of the findings herein is that the peptides of the invention are expressed and complexed with HLA molecules on cancer cells and/or CCL22 expressing APCs. This renders these cancer cells susceptible to destruction by CTLs and emphasizes the usefulness of CCL22 immunization to fight cancer and infections. The presence of spontaneous CTL-responses in PBLs from melanoma patients to HLA-restricted CCL22 derived peptide epitopes shows the immunotherapeutic potential of CCL22 immunogenic peptides.

In an embodiment of the present invention the peptide of the invention is capable of eliciting INF-γ-producing cells in a PBL population of an individual suffering from an clinical condition where CCL22 of SEQ ID NO: 12 or a functional homologue thereof having at least 70% identity to SEQ ID NO: 12 is expressed. The clinical condition is preferably a cancer and/or an infection and most preferably a cancer.

Individual

The individual to be treated with the vaccine composition of the present invention is an individual suffering from a clinical condition. The individual is preferably of a mammalian species and most preferably a human being. The individual may be of any age, young or old, and may be either male or female. The clinical condition from which the individual suffers may be a neoplastic disease such as a cancer, or an infection such as a microbial or viral infection e.g. HIV.

An embodiment of the present invention provides a vaccine for the treatment, reduction of risk of, stabilization of or prevention of a cancer. In another embodiment the present invention provides a vaccine for the treatment, reduction of risk of, stabilization of or prevention of a disease stemming from an infection, such as a microbial or viral infection.

Cancer

The vaccine composition of the present invention may be used to prevent, reduce the risk of or treat a clinical condition. Preferably, the clinical condition is associated with or characterized by the expression of CCL22. CCL22 may be CCL22 as identified in SEQ ID NO: 12 or may be a homolog sharing at least 70% identity therewith in their wild type forms, but need not be functional. It is understood hereby that the expression level of CCL22 (the expression being expression of e.g. hnRNA, mRNA, precursor protein, fully processed protein) is the same or higher than in an individual not suffering from a clinical condition.

In one embodiment of the invention the clinical condition is a proliferative disorder, such as a preneoplastic or neoplastic disorder. In a preferred embodiment of the invention, the clinical condition is cancer. Cancer (malignant neoplasm) is a class of diseases in which a group of cells display the traits of uncontrolled growth (growth and division beyond the normal limits), invasion (intrusion on and destruction of adjacent tissues), and sometimes metastasis (spread to other locations in the body via lymph or blood). These three malignant properties of cancers differentiate them from benign tumors, which are self-limited, do not invade or metastasize. Most cancers form a tumor but some, like leukemia, do not.

A non-limiting group of cancers given as examples of cancers that may be treated, managed and/or prevented by administration of the vaccine of the present invention include: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In a preferred embodiment the vaccine composition according to the invention is capable of eliciting a clinical response in subject, wherein the clinical response may be characterized by a stable disease, in a preferred embodiment the clinical response may be characterized by a partial response or preferably the clinical response may be characterized by complete remission of a cancer. Preferably, the cancer is selected from the group of; melanoma, breast cancer, ovarian cancer, lung cancer, pancreatic cancer, hematologic cancers (such as leukemias), colon and renal cell cancers.

In one aspect of the invention the vaccine composition is capable of eliciting a clinical response in an individual. In one embodiment the clinical response may be characterized by a stable disease (no further worsening or progression), in a preferred embodiment the clinical response may be characterized by a partial response or preferably the clinical response may be characterized by complete remission of a cancer or infections. The clinical response may be determined as described herein below.

In another aspect of the invention the vaccine composition is capable of eliciting a clinical response in subject, wherein the clinical response is characterized by a decrease in the sum of the longest diameter of the largest target lesion. The decrease may be determined as described herein below.

All measurable lesions up to a maximum of five lesions per organ and 10 lesions in total, representative of all involved organs should be identified as target lesions and recorded and measured at baseline.

Target lesions should be selected on the basis of their size (lesions with the longest diameter) and their suitability for accurate repeated measurements (either by imaging techniques or clinically).

A sum of the longest diameter (LD) for all target lesions will be calculated and reported as the baseline sum LD. The baseline sum LD will be used as reference by which to characterize the objective tumor.

All other lesions (or sites of disease) should be identified as non-target lesions and should also be recorded at baseline. Measurements of these lesions are not required, but the presence or absence of each should be noted throughout follow-up.

Evaluation of Target Lesions
  Complete Response (CR): Disappearance of all target lesions
  Partial Response (PR): At least a 30% decrease in the sum of the LD of target lesions, taking as reference the baseline sum LD
  Progressive Disease (PD): At least a 20% increase in the sum of the LD of target lesions, taking as reference the smallest sum LD recorded since the treatment started or the appearance of one or more new lesions
  Stable Disease (SD): Neither sufficient shrinkage to qualify for PR nor sufficient increase to qualify for PD, taking as reference the smallest sum LD since the treatment started Evaluation of Non-Target Lesions
  Complete Response (CR): Disappearance of all non-target lesions and normalization of tumor marker level
  Incomplete Response/Stable Disease (SD): Persistence of one or more non-target lesion(s) or/and maintenance of tumor marker level above the normal limits
  Progressive Disease (PD): Appearance of one or more new lesions and/or unequivocal progression of existing non-target lesions In an embodiment of the present invention the vaccine composition comprising any of the herein mentioned proteins and/or polypeptides is capable of eliciting a clinical response in a subject, wherein the clinical response is characterized by a decrease in the sum of the longest diameter of the largest target lesion It is contemplated that the vaccine composition of the invention is capable of eliciting an immune response against a cancer expressing CCL22 of SEQ ID NO: 12 or a functional homologue thereof having at least 70% identity to SEQ ID NO: 12, when administered to an individual suffering from a cancer expressing CCL22. The vaccine composition of the invention is capable of eliciting the production in a vaccinated individual of effector T-cells having a cytotoxic effect against the cancer cells, CCL22 expressing APCs and/or inducing infiltration of antigen specific T-cells in tumor stroma in a subject.

In addition to their capacity to elicit immune responses in PBL populations it is also contemplated that the peptides of the invention are capable of eliciting cytolytic immune responses in situ, i.e. in solid tumor tissues. This may for example be demonstrated by providing HLA-peptide complexes, e.g. being multimerized and being provided with a detectable label, and using such complexes for immunohistochemistry stainings to detect in a tumor tissue CTLs that are reactive with the epitope peptide of the invention. Accordingly, a further significant feature of the peptide of the invention is that it is capable of in situ detection in a tumor tissue of CTLs that are reactive with the epitope peptide.

It is also contemplated that the peptides of the invention, in addition to their capacity to bind to HLA molecules resulting in the presentation of complexes of HLA and peptides on cell surfaces, which complexes in turn act as epitopes or targets for cytolytic T cells, may elicit other types of immune responses, such as B-cell responses resulting in the production of antibodies against the complexes and/or a Delayed Type Hypersensitivity (DTH) reaction. The latter type of immune response is defined as a redness and palpable induration at the site of injection of the peptide of the invention.

It is an object of the presenting invention to provide a vaccine composition comprising C-C motif chemokine 22 of SEQ ID NO: 12 or SEQ ID NO: 15 or a functional homologue thereof having at least 70% identity to SEQ ID NO: 12 or SEQ ID NO: 15 or an immunogenically active peptide fragment comprising a consecutive sequence of said CCL22 or said functional homologue thereof or a nucleic acid encoding said CCL22 or said peptide fragment; and an adjuvant, for the prevention of, reduction of risk from or treatment of cancer.

Cancer Combination Treatment

In some cases it will be appropriate to combine the treatment method of the invention with a further cancer treatment such as chemotherapy, radiotherapy, treatment with immunostimulating substances, gene therapy, treatment with antibodies and treatment using dendritic cells.

Since elevated expression of CCL22 in tumor cells leads to inhibition of the immune system, the combination of a CCL22-based immunotherapy as disclosed by the present invention with cytotoxic chemotherapy and or another anti-cancer immunotherapeutic treatment is an effective approach to treat cancer. These remedies are also referred to herein as "second active ingredients".

Examples of chemotherapeutic agents that are of relevance in regards to co-administration (sequentially or simultaneously) with the vaccine composition of the present invention include, but are not limited to: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

Another second active ingredient may be a kinase inhibitor, for separate, simultaneous or combined use in the treatment of tumors. Suitable kinase inhibitors include those which have been shown to possess anti-tumor activity (such as gefitinib (Iressa) and erlotinib (Tarceva) and these could be used in combination with the peptides. The receptor tyrosine kinase inhibitors, such as Sunitinib malate and Sorafenib which have been shown to be effective in the treatment of renal cell carcinoma are also suitable to be used as second active ingredients.

Further examples of second active ingredients are immunostimulating substances e.g. cytokines and antibodies. Such as cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction.

Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In an embodiment, the vaccine composition of the present invention, comprising a CCL22 derived polypeptide, is administered in combination with a second active ingredient, such as an immunostimulatory substance. The immunostimulatory substance is preferably an interleukin such as IL-21 or IL-2 or a chemotherapeutic agent.

The vaccine compositions of the invention may also comprise one or more additional antigens in addition to CCL22. Said antigens, may for example be immunogenically active peptides derived from cancer associated proteins.

Thus, the vaccine compositions of the invention may in addition to CCL22 and/or immunogenically active peptide fragments thereof also comprise one or more of the following:
1) Indoleamine-2,3-dioxygenase (IDO)
2) An immunogenically active peptide fragment of IDO
3) A functional homologue of 1) or 2)
4) A polypeptide comprising 1), 2) or 3)
5) A nucleic acid encoding any of 1), 2), 3) or 4).

Said IDO may in particular be IDO of SEQ ID NO: 1 of WO 2009/143843, IDO of SEQ ID NO: 13 of WO 2009/143843, IDO of SEQ ID NO: 14 of WO 2009/143843, IDO of SEQ ID NO: 15 of WO 2009/143843 or IDO of SEQ ID NO: 16 of WO 2009/143843. Useful immunogenically active peptide fragments of IDO, which can be contained in the vaccine compositions of the present invention are described in WO 2009/143843.

The vaccine compositions of the invention may in addition to CCL22 and/or immunogenically active peptide fragments thereof also comprise one or more of the following:
1) PD-L1
2) An immunogenically active peptide fragment of PD-L1
3) A functional homologue of 1) or 2)
4) A polypeptide comprising 1), 2) or 3)
5) A nucleic acid encoding any of 1), 2), 3) or 4).

Said PD-L1 may in particular be PD-L1 of SEQ ID NO: 1 of WO2013/056716. Useful immunogenically active peptide fragments of PD-L1, which can be contained in the vaccine compositions of the present invention, are described in WO2013/056716.

The vaccine compositions of the invention may in addition to CCL22 and/or immunogenically active peptide fragments thereof also comprise one or more of the following:
1) tryptophan 2,3-dioxygenase (TDO)
2) An immunogenically active peptide fragment of TDO
3) A functional homologue of 1) or 2)
4) A polypeptide comprising 1), 2) or 3)
5) A nucleic acid encoding any of 1), 2), 3) or 4).

Said TDO may in particular be TDO of SEQ ID NO: 1 of pending application "Vaccine compositions comprising Tryptophan 2,3-dioxygenase or fragments thereof" filed by the present inventors. Useful immunogenically active peptide fragments of TDO, which can be contained in the vaccine compositions of the present invention, are described in said pending application.

Infections

In another embodiment of the invention, the vaccine compositions disclosed herein are for treatment or prevention of an inflammatory condition.

The term "inflammatory condition" as used herein relates to any kind of clinical condition giving rise to an immune response, such as an inflammation, and therefore includes infectious diseases, chronic infections, autoimmune conditions and allergic inflammations. Thus, inflammatory conditions, such as infectious diseases, chronic infections, autoimmune conditions and allergic inflammations are all clinical conditions of relevance for the present invention, and are dealt with in turn hereunder.

Inflammation is the complex biological response of vascular tissues to harmful stimuli, such as pathogens, damaged cells, or irritants. It is a protective attempt by the organism to remove the injurious stimuli as well as initiate the healing process for the tissue. Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process. In either case, CCL22 is expressed by cells of the immune system such as the APCs and therefore infections and inflammations are clinical conditions that may be treated, prevented, or from which the risk may be reduced by the administration of the vaccine composition of the present invention. The vaccine composition preferably comprises CCL22 protein, protein fragments, polypeptide or peptides derived there from or functional homologues of any of these.

Examples of disorders associated with inflammation which are of relevance to the presenting invention include, but are not limited to: Allergic inflammations, Asthma, Autoimmune diseases, Chronic inflammations, Chronic prostatitis, Glomerulonephritis, Hypersensitivities, Infectious diseases, Inflammatory bowel diseases, Pelvic inflammatory disease, Reperfusion injury, Rheumatoid arthritis, Transplant rejection, and Vasculitis.

Chronic Inflammations

Chronic inflammation is especially of relevance in regard to the present invention. A chronic inflammation is a pathological condition characterized by concurrent active inflammation, tissue destruction, and attempts at repair. Chronically inflamed tissue is characterized by the infiltration of mononuclear immune cells (monocytes, macrophages, lymphocytes, and plasma cells), tissue destruction, and attempts at healing, which include angiogenesis and fibrosis.

In acute inflammation, removal of the stimulus halts the recruitment of monocytes (which become macrophages under appropriate activation) into the inflamed tissue, and existing macrophages exit the tissue via lymphatics. However in chronically inflamed tissue the stimulus is persistent, and therefore recruitment of monocytes is maintained, existing macrophages are tethered in place, and proliferation of macrophages is stimulated (especially in atheromatous plaques).

It is an object of the presenting invention to provide a vaccine composition comprising CCL22 of SEQ ID NO: 12 or SEQ ID NO: 15 or a functional homologue thereof having at least 70% identity to SEQ ID NO: 12 or SEQ ID NO: 15 or an immunogenically active peptide fragment comprising a consecutive sequence of said CCL22 or said functional homologue thereof or a nucleic acid encoding said CCL22 or said peptide fragment; and an adjuvant, for the prevention of, reduction of risk from or treatment of chronic inflammations.

Infectious Diseases

The vaccine composition of the present invention may be used to prevent, reduce the risk from or treat a clinical condition. In a preferred embodiment of the invention, the clinical condition is an infectious disease. The infectious disease may be promoted by any infectious agent such as bacteria, virus, parasites and or fungi that are capable of inducing an increased expression of CCL22 in the individual suffering from the infectious disease; preferably, the infectious disease is or is at risk of becoming a chronic disease. As described in the background of invention, the increased expression of CCL22 has an immediate effect on the microbial agents in the vicinity of the CCL22 expressing organism by depriving it of tryptophan. However, this approach backfires, as the increased CCL22 expression induces inhibits the activity of Treg cells, if the CCL22 expressing cell is an APC. Therefore it is an aspect of the present invention to provide a vaccine composition comprising CCL22 protein, protein fragments, peptides and or variant of any of these for the treatment, amelioration of (lessening of severity) stabilization and/or prevention of a disease caused by an infectious agent.

An infectious diseases may be caused by a virus, and viral diseases against which the vaccine composition of the present invention may be administered in the treatment of include, but are not limited to the following viral diseases: HIV, AIDS, AIDS Related Complex, Chickenpox (Varicella), Common cold, Cytomegalovirus Infection, Colorado tick fever, Dengue fever, Ebola hemorrhagic fever, Hand, foot and mouth disease, Hepatitis, Herpes simplex, Herpes zoster, HPV (Human papillomavirus), Influenza (Flu), Lassa fever, Measles, Marburg hemorrhagic fever, Infectious mononucleosis, Mumps, Norovirus, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease, and Yellow fever. Preferably, the vaccine composition is administered to individuals suffering from HIV/AIDS and viral infections that may cause cancer. The main viruses associated with human cancers are human papillomavirus, hepatitis B and hepatitis C virus, Epstein-Barr virus, and human T-lymphotropic virus; thus it is an object of the present invention to be administered as the treatment of or as part of the treatment of these viral infections.

Examples of bacterial infections of relevance for the present invention include, but are not limited to: Anthrax, Bacterial Meningitis, Botulism, Brucellosis, Campylobacteriosis, Cat Scratch Disease, Cholera, Diphtheria, Epidemic Typhus, Gonorrhea, Impetigo, Legionellosis, Leprosy (Hansen's Disease), Leptospirosis, Listeriosis, Lyme disease, Melioidosis, Rheumatic Fever, MRSA infection, Nocardiosis, Pertussis (Whooping Cough), Plague, Pneumococcal pneumonia, Psittacosis, Q fever, Rocky Mountain Spotted Fever (RMSF), *Salmonellosis*, Scarlet Fever, Shigellosis, Syphilis, Tetanus, Trachoma, Tuberculosis, Tularemia, Typhoid Fever, Typhus, and Urinary Tract Infections. It is an object of the present invention to provide a vaccine for the treatment and/or prevention and/or reduction of risk from a bacterial infection.

It is a further aspect of the present invention to provide a vaccine composition for the treatment and/or prevention and/or reduction of risk from: Parasitic infectious diseases such as, but not limited to: African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trichomoniasis, and Trypanosomiasis; Fungal infectious diseases such as but not limited to: Aspergillosis, Blastomycosis, Candidiasis, Coccidioidomycosis, Cryptococcosis, Histoplasmosis, Tinea pedis; Prion infectious diseases such as but not limited to: transmissible spongiform encephalopathy, Bovine spongiform encephalopathy, Creutzfeldt-Jakob disease, Kuru-Fatal Familial Insomnia, and Alpers Syndrome; thus it is an object of the present invention to be administered as the treatment of or as part of the treatment of these parasitic, fungal or prion caused infections.

Infectious Disease Combination Treatment

It is further provided for that a treatment of any infectious disease by the administration of the vaccine composition according to the present invention may be given in conjunction with a further (second) active ingredient or in combination with a further treatment such as antibiotic treatment, chemotherapy, treatment with immunostimulating substances, treatment using dendritic cells, antiviral agents anti parasitic agents and so forth.

Examples of a second active ingredient that may be used in the treatment of an infectious disease in combination with the vaccine of the present invention include, and are not limited to antibiotics. The term antibiotics herein refers to substances with anti-bacterial, anti-fungal, anti-viral and/or anti-parasitical activity; examples of relevance to the present invention include, but are not limited to: Amikacin, Gentamycin, Kanamycin, Neomycin, Netilmicin, Paromomycin, Streptomycin, Tobramycin, Ertapenem, Imipenem, Meropenem, Chloramphenicol, Fluoroquinolones, Ciprofloxacin, Gatifloxacin, Gemifloxacin, Grepafloxacin, Levofloxacin, Lomefloxacin, Moxifloxacin, Norfloxacin, Ofloxacin, Sparfloxacin, Trovafloxacin, Glycopeptides, Vancomycin, Lincosamides, Clindamycin, Macrolides/Ketolides, Azithromycin, Clarithromycin, Dirithromycin, Erythromycin, Cefadroxil, Cefazolin, Cephalexin, Cephalothin, Cephapirin, Cephradine, Cefaclor, Cefamandole, Cefonicid, Cefotetan, Cefoxitin, Cefprozil, Cefuroxime, Loracarbef, Cefdinir, Cefditoren, Cefixime, Cefoperazone, Cefotaxime, Cefpodoxime, Ceftazidime, Ceftibuten, Ceftizoxime, Ceftriaxone, Cefepime, Monobactams, Aztreonam, Nitroimidazoles, Metronidazole, Oxazolidinones, Linezolid, Penicillins, Amoxicillin, Amoxicillin/Clavulanate, Ampicillin, Sulbactam, Bacampicillin, Carbenicillin, Cloxacillin, Dicloxacillin, Methicillin, Mezlocillin, Nafcillin, Oxacillin, Penicillin G, Penicillin V, Piperacillin, Piperacillin/Tazobactam, Ticarcillin, Ticarcillin/Clavulanate, Streptogramins, Quinupristin, Dalfopristin, Sulfonamide/Sulfamethoxazole, Trimethoprim, Tetracyclines, Demeclocycline, Doxycycline, Minocycline, Tetracycline, Azole antifungals Clotrimazole Fluconazole, Itraconazole, Ketoconazole, Miconazole, Voriconazole, Amphotericin B, Nystatin, Echinocandin, Caspofungin, Micafungin, Ciclopirox, Flucytosine, Griseofulvin, and Terbinafine. Of further relevance are antivirals such as Vidarabine, Acyclovir, Gancyclovir and Valcyte (valganciclovir), Nucleoside-analog reverse transcriptase inhibitors (NRTI): AZT (Zidovudine), ddI (Didanosine), ddC (Zalcitabine), d4T (Stavudine), 3TC (Lamivudine), Non-nucleoside reverse transcriptase inhibitors (NNRTI): Nevirapine, Delavirdine, Protease Inhibitors: Saquinavir, Ritonavir, Indinavir, Nelfinavir, Ribavirin, Amantadine/Rimantadine, Relenza and Tamiflu, Pleconaril, Interferons In an embodiment, the present invention regards a vaccine composition comprising CCL22 derived proteins, polypeptides and/or functional homologs of these for the treatment of an infectious disease in combination with at least one antibiotic. Preferably, the vaccine composition of the present invention is used for the treatment of chronic infections e.g. HIV and therefore is used in combination with any of the above listed antibiotics such as anti-viral agents.

Autoimmune Diseases

Autoimmune diseases arise when an organism fails to recognize its own constituent parts (down to the sub-molecular levels) as self, which results in an immune response against its own cells and tissues. Any disease that results from such an aberrant immune response is termed an autoimmune disease and is of relevance to the present invention. Examples hereof include but are not limited to: Coeliac disease, diabetes mellitus type 1 (IDDM), systemic lupus erythematosus (SLE), Sjögren's syndrome, multiple sclerosis (MS), Hashimoto's thyroiditis, Graves' disease, idiopathic thrombocytopenic purpura, and rheumatoid arthritis (RA).

It is an object of the present invention to provide a vaccine composition comprising CCL22 of SEQ ID NO: 12 or SEQ ID NO: 15 or a functional homologue thereof having at least 70% identity to SEQ ID NO: 12 or SEQ ID NO: 15 or an immunogenically active peptide fragment comprising a consecutive sequence of said CCL22 or said functional homologue thereof or a nucleic acid encoding said CCL22 or said peptide fragment; and an adjuvant, for the prevention of, reduction of risk from or treatment of autoimmune diseases.

Autoimmune Disease Combination Treatment

Current treatments for autoimmune disease are usually immunosuppressive, anti-inflammatory, or palliative. Dietary manipulation limits the severity of celiac disease. Steroidal or NSAID treatment limits inflammatory symptoms of many diseases. Intravenous preparations of immune globulin (IVIG) are used for Chronic Inflammatory Demyelinating Polyneuropathy (CIDP) and Guillain-Barré syndrome (GBS). More specific immunomodulatory therapies, such as the TNFα antagonist Etanercept, have been shown to be useful in treating RA. These immunotherapies may be associated with increased risk of adverse effects, such as susceptibility to infection.

Helminthic therapy has developed based on these observations and involves inoculation of the individual with specific parasitic intestinal nematodes (helminths). There are currently two closely-related treatments available, inoculation with either *Necator americanus*, commonly known as hookworms, or *Trichuris Suis* Ova, commonly known as Pig Whipworm Eggs. Research is available that demonstrates this approach is highly effective in treating a variety of autoimmune disorders, including Crohn's, Ulcerative Colitis, Asthma, allergies, Multiple Sclerosis, and chronic inflammatory disorders In an embodiment, the vaccine herein disclosed is used in combination with a second active ingredient such as any of the above mentioned drugs and treatments against autoimmune diseases.

Allergic Inflammation

Allergy is a disorder of the immune system often also referred to as atopy. Allergic reactions occur to environmental substances known as allergens; these reactions are acquired, predictable and rapid. Strictly, allergy is one of four forms of hypersensitivity and is called type I (or immediate) hypersensitivity. It is characterized by excessive activation of certain white blood cells called mast cells and basophils by a type of antibody, known as IgE, resulting in an extreme inflammatory response. Common allergic reactions include eczema, hives, hay fever, asthma, food allergies, and reactions to the venom of stinging insects such as wasps and bees.

Allergic inflammation is an important pathophysiological feature of several disabilities or medical conditions including allergic asthma, atopic dermatitis, allergic rhinitis and several ocular allergic diseases.

It is an object of the present invention to provide a vaccine composition comprising CCL22 of SEQ ID NO: 12 or SEQ ID NO: 15 or a functional homologue thereof having at least 70% identity to SEQ ID NO: 12 or SEQ ID NO: 15 or an immunogenically active peptide fragment comprising a consecutive sequence of said CCL22 or said functional homologue thereof or a nucleic acid encoding said CCL22 or said peptide fragment; and an adjuvant, for the prevention of, reduction of risk from or treatment of allergic inflammation.

Allergic Inflammation Combination Treatment

Two types of treatments are available for the treatment of allergic inflammations, pharmacotherapy and immunotherapy: pharmacotherapy and immunotherapy.

Pharmacotherapy is the use of antagonistic drugs to block the action of allergic mediators, or to prevent activation of cells and degranulation processes. These include antihistamines, cortisone, dexamethasone, hydrocortisone, epinephrine (adrenaline), theophylline, cromolyn sodium and antileukotrienes, such as Montelukast (Singulair) or Zafirlukast (Accolate); anti-cholinergics, decongestants, mast cell stabilizers, and other compounds thought to impair eosinophil chemotaxis, are also commonly used.

Immunotherapy is the desensitization or hyposensitization treatment in which the individual is gradually vaccinated with progressively larger doses of the allergen in question. A second form of immunotherapy involves the intravenous injection of monoclonal anti-IgE antibodies. A third type, Sublingual immunotherapy, is an orally-administered therapy which takes advantage of oral immune tolerance to non-pathogenic antigens such as foods and resident bacteria.

In an embodiment, the vaccine herein disclosed is used in combination with a second active ingredient such as any of the above mentioned drugs and treatments against allergic inflammations.

Pharmaceutical Compositions

The present invention regards pharmaceutical compositions capable of treating, reducing the risk of and/or preventing a clinical disorder associated with CCL22 expression in an individual. Said pharmaceutical composition may in particular be a vaccine composition. The vaccine compositions of the present invention may be "traditional" vaccine compositions comprising antigens such as proteins polypeptides and/or nucleic acid molecules. They may also be in the form of compositions comprising cells, such as modified cells originating from the individual and later processed, or to compositions comprising complex molecules such as antibodies or TCRs.

Generally, a vaccine is a substance or composition capable of inducing an immune response in an individual. The composition may comprise one or more of the following: an "active component" such as an antigen(s) (e.g. protein, polypeptides, peptides, nucleic acids and the like), nucleic acid constructs comprising one or more antigens amongst other elements, cells, (e.g. loaded APC, T cells for adoptive transder aso.), complex molecules (Antibodies, TCRs and MHC complexes and more), carriers, adjuvants and pharmaceutical carriers. In the following, the various components of a vaccine composition according to the present invention are disclosed in more detail.

The vaccine composition of the invention is capable of eliciting an immune response against a cancer, DC or APC expressing CCL22 of SEQ ID NO: 12 or SEQ ID NO: 15 or a functional homologue thereof having at least 70% identity to SEQ ID NO: 12 or SEQ ID NO: 15, when administered to an individual suffering from a cancer and/or infection (leading to the expression of CCL22). In a preferred embodiment the clinical condition is a cancer. The vaccine composition of the invention is capable of eliciting the production in a vaccinated individual of effector T-cells having a cytotoxic effect against cancer cells, APCs and DCs expressing CCL22 and/or inducing infiltration of antigen specific T-cells in tumor stroma in a subject.

Antigens and Other Active Components

Protein/Polypeptide Based Vaccine Compositions

The peptides of the present invention are ready for use as antigens as they are presented here. Preferably, the vaccine composition of the present invention comprises one or more of the following:

1) C-C motif chemokine 22 (CCL22), which may be any of the CCL22s described herein in the section "C-C motif chemokine 22", in particular human or murine CCL22;
2) An immunogenically active peptide fragment of CCL22 comprising a consecutive sequence of amino acids of CCL22, which may be any of the peptides described herein below in the section "Immunogenically active peptide fragment of CCL22".
3) An immunogenically active peptide fragments of CCL22, which is an MHC Class I-restricted peptide fragment or MHC Class II-restricted peptide fragment, such as any of the an MHC Class I-restricted peptide fragments or MHC Class II-restricted peptide fragments described in the section "MHC";
4) A functional homologue of the polypeptides under 1), 2) and 3);
5) A polypeptide comprising any of polypeptides under 1), 2), 3) and 4), which may be any of the polypeptides described herein below in the section "Polypeptides comprising CCL22 or a fragment thereof";
6) A nucleic acid encoding any of the polypeptides under 1), 2), 3) and 4).

The choice of antigen in the vaccine composition of the invention will depend on parameters determinable by the person of skill in the art. As it has been mentioned, each of the different peptides of the invention is presented on the cell surfaces by a particular HLA molecule. As such, if a subject to be treated is typed with respect to HLA phenotype, a peptide/peptides are selected that is/are known to bind to that particular HLA molecule. Alternatively, the antigen of interest is selected based on the prevalence of the various HLA phenotypes in a given population. As an example, HLA-A2 is the most prevalent phenotype in the Caucasian population, and therefore, a composition containing a peptide binding to HLA-A2 will be active in a large proportion of that population. Furthermore, the antigens/peptides of the present invention may be modified according to the anchor residue motifs presented in Table 2, to enhance binding to particular HLA molecules.

The composition of the invention may also contain a combination of two or more immunogenically active peptide fragments of CCL22 e.g. any of the peptides described in the sections "Immunogenically active peptide fragments of CCL22", "Polypeptides comprising CCL22 or a fragment thereof" and "MHC". Said immunogenically active peptide fragments of CCL22 may each interact specifically with a different HLA molecule so as to cover a larger proportion of the target population. Thus, as examples, the pharmaceutical composition may contain a combination of a peptide restricted by a HLA-A molecule and a peptide restricted by a HLA-B molecule, e.g. including those HLA-A and HLA-B molecules that correspond to the prevalence of HLA phenotypes in the target population, such as e.g. HLA-A2 and HLA-B35. Additionally, the composition may comprise a peptide restricted by an HLA-C molecule.

In the case of peptide-based vaccines, epitopes can be administered in an 'MHC-ready' form, which enables presentation through exogenous loading independently of antigen uptake and processing by host antigen-presenting cells. The peptides of the present invention comprise both peptides in a short 'MHC-ready' form and in a longer form requiring processing by the proteasome thus providing a more complex vaccine composition that can target multiple tumor antigens. The more different HLA groups are targeted by a vaccine, the higher likelihood of the vaccine functioning in diverse populations.

Multi Epitope Vaccine Composition

The invention also relates to highly immunogenic multi-epitope vaccines. Preferably, such vaccines should be designed so as to facilitate a simultaneous delivery of the best-suited immunogenically active peptide fragments of CCL22 optionally in combination with other suitable peptides and/or adjuvants as described hereinafter. The present invention encompasses such multi-epitope vaccines comprising immunogenically active peptide fragments of CCL22 optionally in combination with further proteins or peptides fragments not belonging to or derived from CCL22 and/or adjuvants as described hereinafter. An important factor driving the development of vaccines having a more complex composition is the desire to target multiple tumor antigens e.g. by designing vaccines comprising or encoding a collection of carefully selected CTL and $T_h$ cell epitopes. The invention thus in one aspect relates to vaccine compositions comprising both Class I and Class II-restricted CCL22 epitopes.

The peptides of the present invention thus comprise both peptides in a short 'MHC-ready' form (class I restricted), and in a longer form requiring processing by the proteasome (class II restricted). Thus, the composition according to the present invention may be provided as a multi-epitope vaccine comprising class I restricted epitope and/or class II restricted epitopes as defined hereinbefore.

Nucleic Acid Based Vaccine Composition

The vaccine composition according to the present invention may comprise a nucleic acid encoding a CCL22 polypeptide or an immunologically active peptide fragment thereof. Said nucleic acid may thus encode any of the above-mentioned proteins and peptide fragments. The nucleic acid may for example be DNA, RNA, LNA, HNA, PNA, preferably the nucleic acid is DNA or RNA.

The nucleic acids of the invention may be comprised within any suitable vector, such as an expression vector. Numerous vectors are available and the skilled person will be able to select a useful vector for the specific purpose. The vector may, for example, be in the form of a plasmid, cosmid, viral particle or artificial chromosome. The appropriate nucleic acid sequence may be inserted into the vector by a variety of procedures, for example, DNA may be inserted into an appropriate restriction endonuclease site(s) using techniques well known in the art. Apart from the nucleic acid sequence according to the invention, the vector may furthermore comprise one or more of a signal sequence, an origin of replication, one or more marker genes, an enhancer element, a promoter, and a transcription termination sequence. The vector may also comprise additional sequences, such as enhancers, poly-A tails, linkers, polylinkers, operative linkers, multiple cloning sites (MCS), STOP codons, internal ribosomal entry sites (IRES) and host homologous sequences for integration or other defined elements. Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989). The vector is preferably an expression vector, comprising the nucleic acid operably linked to a regulatory nucleic acid sequence directing expression thereof in a suitable cell. Within the scope of the present invention said regulatory nucleic acid sequence should in general be capable of directing expression in a mammalian cell, preferably a human cell, more preferably in an antigen presenting cell.

In one preferred embodiment the vector is a viral vector. The vector may also be a bacterial vector, such as an attenuated bacterial vector. Attenuated bacterial vectors may be used in order to induce lasting mucosal immune responses at the sites of infection and persistence. Different recombinant bacteria may be used as vectors, for example the bacterial vector may be selected from the group consisting of *Salmonella, Lactococcus*], and *Listeria*. In general, induction of immunity to the heterologous antigen HPV16 L1 or E7 could be shown, with strong CTL induction and tumor regression in mice. The vector may furthermore comprise a nucleic acid encoding a T-cell stimulatory polypeptide.

Loaded APCs

In useful embodiments an immunogenic response directed against a cancer disease is elicited by administering the peptide of the invention either by loading MHC class I or class II molecules on antigen presenting cells (APCs) from the individual, by isolating PBLs from the individual and incubating the cells with the peptide prior to injecting the cells back into the individual or by isolating precursor APCs from the individual and differentiating the cells into professional APCs using cytokines and antigen before injecting the cells back into the individual.

It is thus an aspect of the invention to provide vaccine compositions comprising antigen presenting cells comprising CCL22 or an immunologically active peptide fragment thereof or a nucleic acid encoding said protein or said immunologically active peptide fragment. The antigen presenting cell may be any cell capable of presenting an antigen to a T-cell. Preferred antigen presenting cells are dendritic cells. The dendritic cells (DC) may be prepared and used in therapeutic procedure according to any suitable protocol, for example as described herein below. It will be appreciated by the person skilled in the art that the protocol may be adopted to use with individuals with different HLA type and different diseases.

Dendritic cells (DC) may be pulsed with 50 μg/ml HLA-restricted peptide (synthesized at GMP quality) for 1 h at 37° C. peptide and $5 \times 10^6$ cells are administered subcutaneously at day 1 and 14, subsequently every 4 weeks, additional leukapheresis after 5 vaccinations. The generation of DC for clinical use and quality control can be performed essentially as described in Nicolette et al., (2007).

Thus, in one embodiment of the present invention, a method for treating an individual suffering from a clinical condition characterized by the expression of CCL22, preferably wherein the clinical condition is cancer or an infection, is one wherein the peptide is administered by presenting the peptide to the individual's antigen presenting cells (APCs) ex vivo followed by injecting the thus treated APCs back into the individual. There are at least two alternative ways of performing this. One alternative is to isolate APCs from the individual and incubate (load) the MHC class I molecules with the peptide. Loading the MHC class I molecules means incubating the APCs with the peptide so that the APCs with MHC class I molecules specific for the peptide will bind the peptide and therefore be able to present it to T cells. Subsequently, the APCs are re-injected into the individual. Another alternative way relies on the recent discoveries made in the field of dendritic cell biology. In this case, monocytes (being dendritic cell precursors) are isolated from the individual and differentiated in vitro into professional APC (or dendritic cells) by use of cytokines and antigen. Subsequently, the in vitro generated DCs are pulsed with the peptide and injected into the individual.

Adoptive Immunotherapy/Adoptive Transfer

An important aspect the invention relates to cultivating CCL22 specific T-cells in vitro and adoptive transfer of these to individuals. Adoptive transfer means that the physician directly transfers the actual components of the immune system that are already capable of producing a specific immune response, into an individual.

It is one objective to the present invention to provide CCL22 specific T-cells, which may be useful for example for adoptive transfer. Isolated T-cells comprising T-cell receptors capable of binding specifically to CCL22 peptide/MHC class I or CCL22 peptide/MHC class II complexes can be adoptively transferred to individuals, said T-cells preferably being T-cells that have been expanded in vitro, wherein the CCL22 peptide may be any of the immunigenically active peptide fragments of CCL22 mentioned herein above. Methods of expanding T-cells in vitro are well known to the skilled person. The invention also relates to methods of treatment comprising administering T-cells comprising T-cell receptors capable of binding specifically to a MHC-restricted CCL22 peptide complex to an individual, such as a human being suffering from a cancer disease, wherein the CCL22 derived peptide may be any of the CCL22 peptides mentioned herein above. The invention furthermore relates to use of T-cells comprising T-cell receptors capable of binding specifically to CCL22 or peptide fragments thereof for the preparation of a medicament for the treatment of a cancer or infection. Autologous T-cell transfer may be performed essentially as described in Walter et al., (1995).

TCR Transfer

In yet another embodiment, such T-cells could be irradiated before adoptive transfer to control proliferation in the individual. It is possible to genetically engineer the specificity of T cells by TCR gene transfer (Engels et al., 2007). This allows the transfer of T cells bearing CCL22 peptide specificity into individuals. In general, the use of T cells for adoptive immunotherapy is attractive because it allows the expansion of T cells in a tumor- or virus-free environment, and the analysis of T cell function prior to infusion.

The application of TCR gene-modified T cells (such as T-cells transformed with an expression construct directing expressing of a heterologous TCR) in adoptive transfer has several advantages in comparison to the transfer of T cell lines: (i) the generation of redirected T cells is generally applicable. (ii) High-affinity or very high-affinity TCRs can be selected or created and used to engineer T cells. (iii) High-avidity T cells can be generated using codon optimized or murinized TCRs allowing better surface expression of the stabilized TCRs. Genetic engineering of T cell specificity by T cell receptor (TCR) gene transfer may be performed essentially as described in Morgan et al. (2006).

TCR Transfection

TCR with known anti-tumor reactivity can be genetically introduced into primary human T lymphocytes. Genes encoding TCR alpha and beta chains from a tumor specific CTL clone can be transfected into primary T cells and in this way reprogram T cells with specificity against the tumor antigen. TCR RNA is transfected into PBL by electroporation (Schaft et al., 2006). Alternatively, T cells can be provided with at new specificity by TCR gene transfer using retroviral vectors (Morgan et al., 2006). However, the provirus from the retroviral vector might integrate at random in the genome of the transfected cells and subsequently disturb cell growth. Electroporation of T cells with TCR-coding RNA overcome this disadvantage, since RNA is only transiently present in the transfected cells and cannot be integrated in the genome (Schaft et al., 2006). Furthermore, transfection of cells is routinely used in the laboratory.

Adjuvants and Carriers

The vaccine composition according to the invention preferably comprises an adjuvant and/or a carrier. Examples of useful adjuvants and carriers are given herein below. Thus the CCL22 polypeptide, the immunogenically active peptide fragments of CCL22 or functional homologues thereof, the polypeptides comprising same or nucleic acid encoding same may in a composition of the present invention be associated with an adjuvant and/or a carrier.

Adjuvants are any substance whose admixture into the vaccine composition increases or otherwise modifies the immune response to the CCL22 or to immunogenically active peptide fragments of CCL22, see further in the below. Carriers are scaffold structures, for example a polypeptide or a polysaccharide, to which the CCL22 or peptide fragment thereof is capable of being associated and which aids in the presentation of especially the peptides of the present invention.

Many of the peptides of the invention are relatively small molecules and it may therefore be required in compositions as described herein to combine the peptides with various materials such as adjuvants and/or carriers, to produce vaccines, immunogenic compositions, etc. Adjuvants, broadly defined, are substances which promote immune responses. A general discussion of adjuvants is provided in Goding, Monoclonal Antibodies: Principles & Practice (2nd edition, 1986) at pages 61-63. Goding notes, that when the antigen of interest is of low molecular weight, or is poorly immunogenic, coupling to an immunogenic carrier is recommended. Examples of such carrier molecules include keyhole limpet haemocyanin, bovine serum albumin, ovalbumin and fowl immunoglobulin. Various saponin extracts have also been suggested to be useful as adjuvants in immunogenic compositions. It has been proposed to use granulocyte-macrophage colony stimulating factor (GM-CSF), a well known cytokine, as an adjuvant (WO 97/28816).

A carrier may be present independently of an adjuvant. The function of a carrier can for example be to increase the molecular weight of in particular peptide fragments in order to increase their activity or immunogenicity, to confer stability, to increase the biological activity, or to increase serum half-life. Furthermore, a carrier may aid in presenting the CCL22 protein, polypeptide, functional homologue or peptide fragments thereof to T-cells. The carrier may be any suitable carrier known to a person skilled in the art, for example a protein or an antigen presenting cell. A carrier protein could be, but is not limited to, keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diphtheria toxoid are suitable carriers in one embodiment of the invention. Alternatively, the carrier may be dextrans for example sepharose.

Thus it is an aspect of the present invention that the CCL22 protein, polypeptide fragment, variant or peptide derived here from present in the composition is associated with a carrier such as e.g. a protein of the above or an antigen-presenting cell such as e.g. a dendritic cell (DC).

Adjuvants could for example be selected from the group consisting of: $AlK(SO_4)_2$, $AlNa(SO_4)_2$, $AlNH_4 (SO_4)$, silica, alum, $Al(OH)_3$, $Ca_3 (PO_4)_2$, kaolin, carbon, aluminum hydroxide, muramyl dipeptides, N-acetyl-muramyl-L-threo-nyl-D-isoglutamine (thr-DMP), N-acetyl-nornuramyl-L-ala-nyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), R1131 (MPL+TDM+CWS) in a 2% squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from *Mycobacterium*, tuberculosis, substances found in *Corynebacterium parvum*, *Bordetella pertussis*, and members of the genus *Brucella*, Titermax, ISCOMS, Quil A, ALUN (see U.S. Pat. Nos. 58,767 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Preferred adjuvants to be used with the invention include oil/surfactant based adjuvants such as Montanide adjuvants (available from Seppic, Belgium), preferably Montanide ISA-51. Other preferred adjuvants are bacterial DNA based adjuvants, such as adjuvants including CpG oligonucleotide sequences. Yet other preferred adjuvants are viral dsRNA based adjuvants, such as poly I:C. Imidazo-chinilines are yet another example of preferred adjuvants. The most preferred adjuvants are adjuvants suitable for human use.

Montanide adjuvants (all available from Seppic, Belgium), may be selected from the group consisting of Montanide ISA-51, Montanide ISA-50, Montanide ISA-70, Montanide ISA-206, Montanide ISA-25, Montanide ISA-720, Montanide ISA-708, Montanide ISA-763A, Montanide ISA-207, Montanide ISA-264, Montanide ISA-27, Montanide ISA-35, Montanide ISA 51F, Montanide ISA 016D and Montanide IMS, preferably from the group consisting of Montanide ISA-51, Montanide IMS and Montanide ISA-720, more preferably from the group consisting of Montanide ISA-51. Montanide ISA-51 (Seppic, Inc.) is oil/surfactant based adjuvants in which different surfactants are combined with a non-metabolizable mineral oil, a metabolizable oil, or a mixture of the two. They are prepared for use as an emulsion with an aqueous solution comprising CCL22 or a peptide fragment thereof. The surfactant is mannide oleate. QS-21 (Antigenics; Aquila Biopharmaceuticals, Framingham, Mass.) is a highly purified, water-soluble saponin that handles as an aqueous solution. QS-21 and Montanide ISA-51 adjuvants can be provided in sterile, single-use vials.

The well-known cytokine GM-CSF is another preferred adjuvant of the present invention. GM-CSF has been used as an adjuvant for a decade and may preferably be GM-CSF as described in WO 97/28816.

Desirable functionalities of adjuvants capable of being used in accordance with the present invention are listed in the below table.

TABLE 3

Modes of adjuvant action

| Action | Adjuvant type | Benefit |
| --- | --- | --- |
| 1. Immuno-modulation | Generally small molecules or proteins which modify the cytokine network | Upregulation of immune response. Selection of Th1 or Th2 |
| 2. Presen-tation | Generally amphipathic molecules or complexes which interact with immunogen in its native conformation | Increased neutralizing antibody response. Greater duration of response |
| 3. CTL induction | Particles which can bind or enclose immunogen and which can fuse with or disrupt cell membranes | Cytosolic processing of protein yielding correct class 1 restricted peptides |
|  | w/o emulsions for direct attachment of peptide to cell surface MHC-1 | Simple process if promiscuous peptide(s) known |
| 4. Targeting | Particulate adjuvants which bind immunogen. Adjuvants which saturate Kupffer cells | Efficient use of adjuvant and immunogen |
|  | Carbohydrate adjuvants which target lectin receptors on macrophages and DCs | As above. May also determine type of response if targeting selective |
| 5. Depot Generation | w/o emulsion for short term | Efficiency Potential for single-dose vaccine |
|  | Microspheres or nanospheres for long term |  |

Source: Cox, J. C., and Coulter, A. R. (1997). Vaccine 15, 248-56.

A vaccine composition according to the present invention may comprise more than one adjuvant. Furthermore, the invention encompasses a therapeutic composition further comprising any adjuvant substance and/or carrier including any of the above or combinations thereof. It is also contemplated that the CCL22 protein, variants or peptide fragments thereof, and the adjuvant can be administered separately in any appropriate sequence. Preferably, the vaccine compositions of the present invention comprise a Montanide adjuvant such as Montanide ISA 51 or Montanide ISA 720 or the GM-CSF adjuvant.

Accordingly, the invention encompasses a therapeutic composition further comprising an adjuvant substance including any of the above or combinations thereof. It is also contemplated that the antigen, i.e. the peptide of the invention and the adjuvant can be administered simultaneously or separately in any appropriate sequence.

Dosis and Administration

The amount of CCL22 or the immunogenically active peptide fragments of CCL22 of the invention in the vaccine composition may vary, depending on the particular application. However, a single dose of the peptide composition is preferably anywhere from about 10 µg to about 5000 µg, more preferably from about 50 µg to about 2500 µg such as about 100 µg to about 1000 µg. In particular, in embodiments of the invention where the individual to be treated is a human being, then a single dose may be in the range of 50 µg to 500 µg, for example in the range of 80 µg to 300 µg, such as in the range of 100 µg to 250 µg of CCL22 or said immunogenically active peptide fragment of CCL22. Frequently, the vaccine compositions are administered repeatedly over time. For example the vaccine composition may be administered at least 2 times, preferably at least 5 times, more preferably at least 10 times, such as in the range of 10 to 20 times. The vaccine composition may also be administered continuously. Administration may be repeated at any useful frequency. Thus, for example the vaccine compositions may be administered once every week, such as once every two weeks, for example once every 3 weeks, such as once per month, for example once per two months, such as once per three months, for example once per half year, such as once per year. In particular, the vaccine compositions may be administered continuously. The frequency of administration may alter during said time. In one embodiment the vaccine compositions are administered continuously once per 1 to 3 months. Modes of administration include intradermal, subcutaneous and intravenous administration, implantation in the form of a time release formulation, etc. Any and all forms of administration known to the art are encompassed herein. Also any and all conventional dosage forms that are known in the art to be appropriate for formulating injectable immunogenic peptide composition are encompassed, such as lyophilized forms and solutions, suspensions or emulsion forms containing, if required, conventional pharmaceutically acceptable carriers, diluents, preservatives, adjuvants, buffer components, etc.

The pharmaceutical compositions may be prepared and administered using any conventional protocol known by a person skilled in the art. In examples 3-5 non-limiting examples of preparation of a vaccine composition according to the invention is given as well as a non-limiting example of administration of such as a vaccine. It will be appreciated by the person skilled in the art that the protocol may be easily adapted to any of the vaccine compositions described herein. In a further embodiment of the invention, the pharmaceutical composition of the invention is useful for treating an individual suffering from a clinical condition characterized by expression of CCL22, such as cancer and infections.

The immunoprotective effect of the composition of the invention can be determined using several approaches known to those skilled in the art. A successful immune response may also be determined by the occurrence of DTH reactions after immunization and/or the detection of antibodies specifically recognizing the peptide(s) of the vaccine composition.

Vaccine compositions according to the invention may be administered to an individual in therapeutically effective amounts. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the methods of prophylaxis and treatment with the vaccine composition.

For example, the vaccine compositions can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the vaccine, comprising any of the herein described compounds can be employed as a prophylactic or therapeutic agent. Also any and all conventional dosage forms that are known in the art to be appropriate for formulating injectable immunogenic peptide composition are encompassed, such as lyophilized forms and solutions, suspensions or emulsion forms containing, if required, conventional pharmaceutically acceptable carriers, diluents, preservatives, adjuvants, buffer components, etc.

Preferred modes of administration of the vaccine composition according to the invention include, but are not limited to systemic administration, such as intravenous or subcutaneous administration, intradermal administration, intramuscular administration, intranasal administration, oral administration, rectal administration, vaginal administration, pulmonary administration and generally any form of mucosal administration. Furthermore, it is within the scope of the present invention that the means for any of the administration forms mentioned in the herein are included in the present invention.

A vaccine according to the present invention can be administered once, or any number of times such as two, three, four or five times. Administering the vaccine more than once has the effect of boosting the resulting immune response. The vaccine can further be boosted by administering the vaccine in a form or body part different from the previous administration. The booster shot is either a homologous or a heterologous booster shot. A homologous booster shot is a where the first and subsequent vaccinations comprise the same constructs and more specifically the same delivery vehicle especially the same viral vector. A heterologous booster shot is where identical constructs are comprised within different viral vectors.

Second Active Ingredient

It is an aspect of the present invention that the vaccine composition herein provided is used in combination with a second active ingredient. The administration of the vaccine composition and the second active ingredient may be sequential or combined. Examples of second active ingredients are given above for both cancers and infections. It is a further aspect that the vaccine composition may be used in combination with other therapy of relevance for the given clinical condition to be treated. Such therapy may include surgery, chemotherapy or gene therapy, immunostimulating substances or antibodies; a person skilled in the art is able to determine the appropriate combination treatment for a given scenario.

In some cases it will be appropriate to combine the treatment method of the invention with a further medical treatment such as chemotherapy, radiotherapy, treatment with immunostimulating substances, gene therapy, treatment with antibodies and/or antibiotics and treatment using dendritic cells.

Monitoring Immunization

In preferred embodiments, the pharmaceutical composition of the invention is a vaccine composition. It is therefore of interest, and an aspect of the present invention to monitor the immunization in an individual to whom the vaccine composition of the present invention is administered. The pharmaceutical composition may thus be an immunogenic composition or vaccine capable of eliciting an immune response to a cancer and/or infection. As used herein, the expression "immunogenic composition or vaccine" refers to a composition eliciting at least one type of immune response directed against CCL22 expressing cells such as cancer cells, APCs or DCs. Thus, such an immune response may be any of the following: A CTL response where CTLs are generated that are capable of recognizing the HLA/peptide complex presented on cell surfaces resulting in cell lysis, i.e. the vaccine elicits the production in the vaccinated subject of effector T-cells having a cytotoxic effect against the cancer cells; a B-cell response giving rise to the production of anti-cancer antibodies; and/or a DTH type of immune response. It is on object of the present invention to monitor the immunization of an individual by monitoring any of the above reactions subsequent to administering the composition of the present invention to said individual.

In one aspect the invention relates to methods of monitoring immunization, said method comprising the steps of
i) providing a blood sample from an individual
ii) providing CCL22 or a peptide fragment hereof, wherein said protein or peptide may be any of the proteins or peptides described herein
iii) determining whether said blood sample comprises antibodies or T-cells comprising T-cell receptors specifically binding the protein or peptide
iv) thereby determining whether an immune response to said protein or peptide has been raised in said individual.

The individual is preferably a human being, for example a human being that has been immunized with CCL22 or immunogenically active peptide fragments of CCL22 or a nucleic acid encoding said protein or peptide.

Kit of Parts

The invention also relates to a kit-of-parts comprising
 any of the vaccine compositions described herein and/or
 a CCL22 protein or functional homologue hereof and/or
 any of the immunogenically active peptide fragments of CCL22, functional homologues hereof, and/or peptides derived here from as described herein and/or
 any of the nucleic acids encoding the proteins of the above two bullet points
and instructions on how to use the kit of parts.

The invention also relates to a kit-of-parts comprising
 any of the vaccine compositions described herein and/or
 a CCL22 protein or functional homologue hereof and/or
 any of the immunogenically active peptide fragments of CCL22, functional homologues hereof, and/or peptides derived here from as described herein and/or
 any of the nucleic acids encoding the proteins of the above two bullet points
and a second active ingredient.

Preferably, the second active ingredient is chosen in correspondence with the clinical condition to be treated so that in the case where a cancer is to be treated the second active ingredient is chosen among e.g. chemotherapeutic agents as listed above. Likewise, if treating a microbial/viral infection, the second active ingredient is preferably an anti-biotic and/or an anti-viral agent.

The components of the kit-of-parts are preferably comprised in individual compositions, it is however within the scope of the present invention that the components of the kit-of-parts all are comprised within the same composition. The components of the kit-of-parts may thus be administered simultaneously or sequentially in any order.

SEQUENCE LISTING

| SEQ ID NO | Description |
|---|---|
| SEQ ID NO: 1 | Polypeptide fragment of human CCL22, $CCL22_{1-22}$ |
| SEQ ID NO: 2 | Polypeptide fragment of human CCL22, $CCL22_{7-15}$ |

-continued

| SEQ ID NO | Description |
|---|---|
| SEQ ID NO: 3 | Polypeptide fragment of human CCL22, $CCL22_{3-11}$ |
| SEQ ID NO: 4 | Polypeptide fragment of human CCL22, $CCL22_{3-12}$ |
| SEQ ID NO: 5 | Polypeptide fragment of human CCL22, $CCL22_{11-19}$ |
| SEQ ID NO: 6 | Polypeptide fragment of human CCL22, $CCL22_{5-13}$ |
| SEQ ID NO: 7 | Polypeptide fragment of human CCL22, $CCL22_{14-22}$ |
| SEQ ID NO: 8 | Polypeptide fragment of human CCL22, $CCL22_{8-17}$ |
| SEQ ID NO: 9 | Polypeptide fragment of human CCL22, $CCL22_{9-17}$ |
| SEQ ID NO: 10 | Polypeptide fragment of human CCL22, $CCL22_{6-15}$ |
| SEQ ID NO: 11 | Polypeptide fragment of human CCL22, $CCL22_{1-24}$ |
| SEQ ID NO: 12 | Amino acid sequence of CCL22 of Homo sapiens |
| SEQ ID NO: 13 | mCL22long |
| SEQ ID NO: 14 | mCL22short |
| SEQ ID NO: 15 | Full length amino acid sequence of murine CCL22, Uniprot accession number O88430 |
| SEQ ID NO: 16 | Consensus sequence |

EXAMPLES

The invention is further illustrated by the following examples, which should however not be construed as limiting for the invention.

Example 1—Methods

PBMC—Patient Material

Peripheral Blood Mononuclear Cells (PBMC) were collected from healthy individuals and cancer patients (melanoma, renal cell carcinoma and breast cancer patients). Blood samples were drawn a minimum of four weeks after termination of any kind of anti-cancer therapy. PBMC were isolated using Lymphoprep™ separation, HLA-typed and frozen in FCS with 10% DMSO. Fresh ovarian ascites was filtered with a 70 μm filter and the cells were isolated by centrifugation (1500 RPMI-1640, 5 min). If the ascites contained a high abundance of erythrocytes, they were removed by adding lysis-buffer (Ortho-Mune Lysing Solution) to the cells with incubation of 3-5 min. The lysis-buffer was quickly washed away and the cells cryopreserved in human serum with 10% DMSO at −140 degrees until use. The protocol was approved by the Scientific Ethics Committee for The Capital Region of Denmark and conducted in accordance with the provisions of the Declaration of Helsinki. Written informed consent from the patients was obtained before study entry.

Establishment of Antigen-Specific T-Cell Cultures

CCL22-specific T cell cultures were established by stimulation of cancer patient PBMC with irradiated $pCCL22_{3-12}$ peptide-loaded autologous DC or PBMCs. The following day IL-7 and IL-12 (PeproTech, London, UK) were added. Stimulation of the cultures were carried out every 8 days with $CCL22_{3-12}$ peptide loaded irradiated autologous DC followed by $pCCL22_{3-12}$ peptide-loaded irradiated autologous PBMC. The day after peptide stimulation IL-2 (PeproTech, London, UK) was added. 4 DC stimulations and 1 PBMC stimulation were made in total.

Generation of DC

DC were generated from PBMC by adherence on culture dishes at 37° C. for 1-2 hr. in RPMI-1640. Adherent monocytes were cultured in RPMI-1640 supplemented with 10% fetal calf serum in the presence of IL-4 (250 U/ml) and GM-CSF (1000 U/ml) for 6 days. DC were matured by addition of IL-13 (1000 U/ml), IL-6 (1000 U/ml) TNF-α (1000 U/ml) and $PGE_2$ (1 ug/ml).

Cytotoxicity Assay

Conventional $^{51}$Cr-release assays for CTL-mediated cytotoxicity were carried out as described elsewhere (Andersen et al., 1999). Target cells were T2-cells (ATCC), HLA-A2$^+$ EBV transformed B-cell line (RPM16666), AML cells (UKE-1 and THP1) colon cancer cells (SW480), melanoma cell line (FM55-M2), Breast cancer cells MDA-MB231 with or without IFN-γ (100 U/ml) addition for 2 days prior to performing cytotoxicity assay.

For peptide titration cytotoxicity assay, T2 cells were used as target cells and a constant effector to target ratio of 3:1 was used for all peptide concentrations. 10-fold serial peptide dilutions ranging from 10-2 mM to 10-9 mM of pCCL22$_{3-12}$ and pCCL22$_{3-11}$ were made.

siRNA Mediated CCL22 Silencing

A set of three Stealth siRNA duplexes for targeted silencing of CCL22 (HSS109578, HSS184551, HSS184552) were obtained from Invitrogen (Invitrogen, Paisley, UK). For CCL22 silencing experiments, THP-1 cells were transfected with CCL22 siRNA using electroporation parameters as previously described (Met et al., 2011; Hobo et al., 2010).

Flow Cytometric Analysis

Flow cytometry analysis was performed on a FACSCanto™ II (BD Biosciences, San Jose Calif., USA), cell sorting was performed on FACSAria™ (BD Biosciences, San Jose Calif., USA).

Intracellular staining of CCL22-specific T cell cultures was performed after the cells were stimulated with HIV or pCCL22$_{3-12}$ peptides for 5 hours (BD GolgiPlug™ was added after the first hour). The cells were then stained for surface markers, then washed and permeabilized by using Fixation/Permeabilization and Permeabilization Buffer (eBioscience), according to manufacturer's instructions. Antibodies used: IFNγ-PE-Cy7, TNFα-APC, CD4-PerCP, CD8-FITC (all from BD Biosciences). Dead cells were stained using LIVE/DEAD® Fixable Near-IR Dead Cell Stain Kit according to manufacturer's instructions.

For tetramer staining and sorting PE and APC coupled HLA-A2 multimers with HIV or pCCL22$_{3-12}$ peptides were used in addition to the CD4-PerCP and CD8-FITC (BD Biosciences). HLA-A2 multimers were produced in house by using a previously described MHC peptide exchange technology (15).

ELISPOT Assay

In the present study the ELISPOT was performed according to the guidelines provided by CIP (http://cimt.eu/cimt/files/dl/cip_guidelines.pdf). The ELISPOT assay was used to quantify peptide epitope specific effector cells that release cytokines (IFNγ, TNFα, IL-17A or IL-10) as described previously (Sorensen et al., 2012). In some experiments, PBMCs were stimulated once in vitro with peptide prior to analysis. In some experiments, 10$^4$ autologous DCs were added to the wells as antigen presenting cells. The spots were counted using the ImmunoSpot Series 2.0 Analyzer (C.T.L.-Europe, Bonn, Germany). In some experiments, CD4$^+$ cells were isolated by EasySep human CD4$^+$ T cell enrichment kit (Stem Cell technologies, Grenoble, France) following manufacturers' instructions. This yielded highly pure cultures (>97% CD4+), which was confirmed by staining with surface antibodies as described below for intracellular cytokine staining (ICS) and flow cytometry (FCM).

PBMCs were placed in the bottom of ELISPOT plate (nitrocellulose bottomed 96-well plates by MultiScreen MAIP N45; Millipore) pre-coated with IFN-γ capture Ab (Mabtech) and the peptides were added at 5 µg/ml. PBMCs from each patient were set up in duplicates or triplicates for peptide and control stimulations. Cells were incubated in ELISPOT plates in the presence of an antigen for 14-16 hours after which they are washed off and secondary biotinylated Ab (Mabtech) was added. After 2 h incubation unbound secondary antibody was washed off and streptavidin conjugated alkaline phosphatase (AP) (Mabtech) was added for 1 h. Next, unbound conjugated enzyme is washed off and the assay is developed by adding BCIP/NBT substrate (Mabtech). Developed ELISPOT plates were analysed on CTL ImmunoSpot S6 Ultimate-V analyzer using Immunospot software v5.1. Responses were calculated as the difference between average numbers of spots in wells stimulated with pCCL22$_{3-12}$ peptide and control wells.

Analysis of CCL22 Expression

Cell culture supernatants from PBMC, cancer cell lines and ascites cell cultures as well as siRNA transfected THP-1 cells were analyzed using Human CCL22/MDC DuoSet ELISA kit (R&D Systems) according to manufacturer's instructions.

Peptide Stimulation of PBMCs and Ascites Cells

PBMCs from healthy donors or cancer patients were thawed and rested for 4 hours in X-VIVO 15™ (Lonza) before being set up into 24-well plates with 2×10$^6$ cells/well in X-Vivo medium with 5% human serum. 20 µg/ml of pCCL22$_{3-12}$ peptide in DMSO or HIV peptide in sterile water were added to each well. Appropriate amount of DMSO was added to HIV control wells to control for the solvent of pCCL22$_{3-12}$ peptide. The following day, IL-2 was added to a final concentration of 120 U/ml (360 U for ascites cells stimulation). Supernatant samples were collected after 2 or 7 days of culture. Cells were stimulated twice before being tested in ELISPOT assay.

Cytokine Expression LUMINEX

Cell culture supernatants from PBMCs or ascites cells stimulated with CCL22-3 or HIV peptide were analyzed for IFN-γ, TNF-α, IL-6, IL-10 and IL-1β using Bio-Plex Pro™ Human Chemokine assays from Bio-Rad. Samples were acquired on Bio Plex 200 system and analyzed using Bio-Plex Manager™ v6.

Statistical Analysis t-test was used for the statistical analysis of ELISA samples from cancer patients and healthy donors when comparing pCCL22$_{3-12}$ stimulation with HIV control. The same analysis was used to compare IFN-γ, TNF-α, IL-6, IL-10 expression after pCCL22$_{3-12}$ stimulation with HIV control. Wilcoxon-signed rank test was used for statistical analysis of IL-10 expression due to multiple zero values.

Example 2—Results

A panel of CCL22-derived HLA-binding peptides was predicted using SYFPEITHI database (www.syfpeithi.de):

| | | |
|---|---|---|
| CCL22-1 | ALLVVLVLL | (7-15) |
| CCL22-2 | RLQTALLVV | (3-11) |
| CCL22-3 | RLQTALLVVL | (3-12) |
| CCL22-4 | VLVLLAVAL | (11-19) |
| CCL22-5 | QTALLVVLV | (5-13) |
| CCL22-6 | LLAVALQAT | (14-22) |
| CCL22-7 | LLVVLVLLAV | (8-17) |
| CCL22-8 | LVVLVLLAV | (9-17) |

-continued

| CCL22-9 | TALLVVLVL | (6-15) |
| CCL22 LONG | MDRLQTALLVVLVLLAVALQAT | (1-22) |
| CCL22-SIGNAL | MDRLQTALLVVLVLLAVALQATEA | (1-24) |

PBMCs from cancer patients were screened for responses against these peptide epitopes by IFNγ ELISPOT. Indications for specific responses against CCL22 peptide CCL22-3 (SEQ ID NO: 4) were found in a number of melanoma patients.

PBMCs from a melanoma patient were stimulated with autologous DCs pulsed with the CCL22-3 peptide. After 5 stimulations the T cell culture was found to specifically recognize and lyse CCL22-3 pulsed T2 cells (FIG. 3A).

Figure 2:
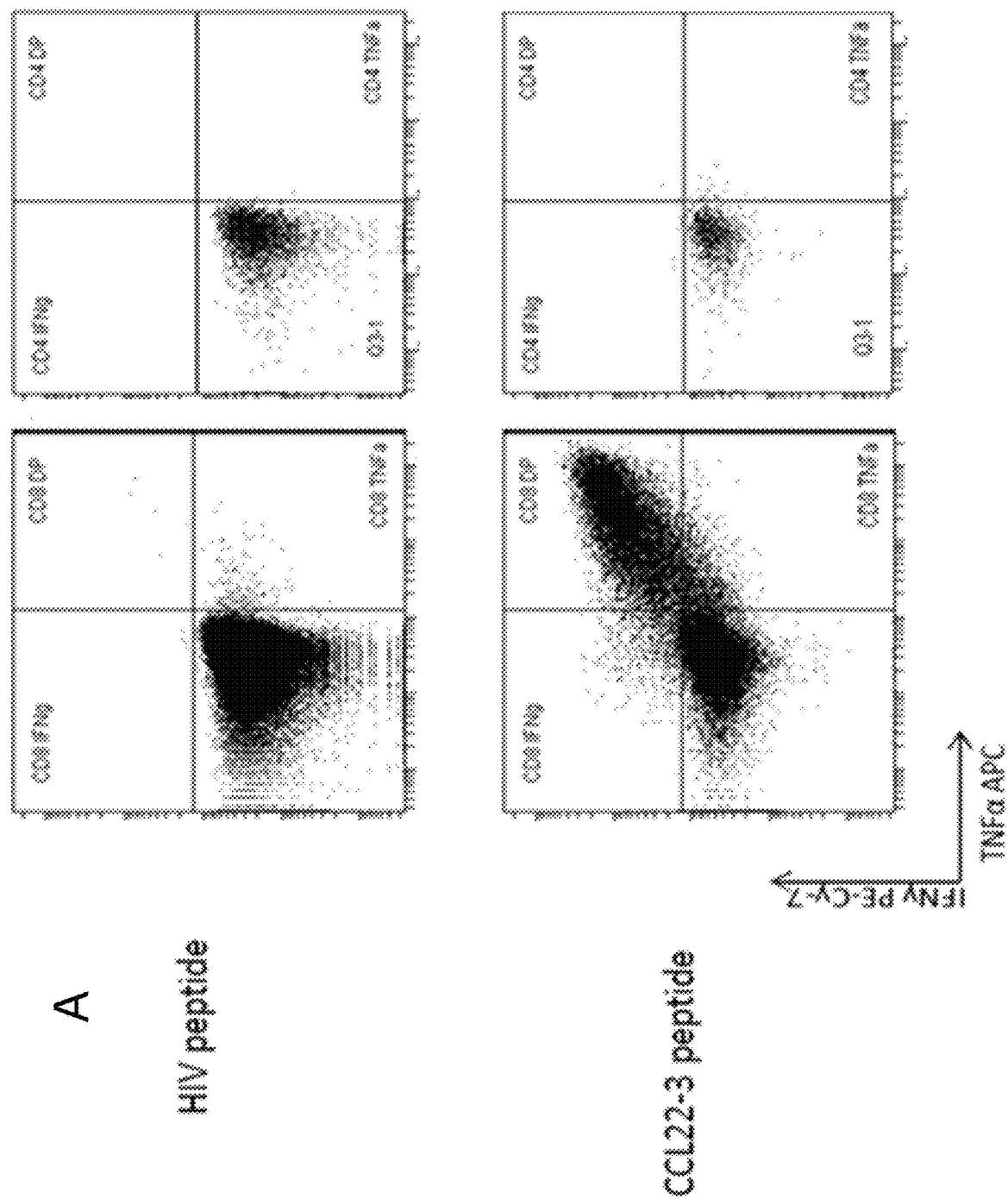
FIG. 2: CCL22 specific CD8+ T cells exist in peripheral blood. A—Intracellular staining for IFNγ and TNFα release shows that CD8+ (Left) and not CD4+ (Right) T cells react against CCL22-3 peptide epitope. B—Left: CCL22-3 peptide reactive T cells can be enriched from peripheral blood of melanoma cancer patient by stimulation with peptide pulsed autologous DCs. Right—tetramer isolated and rapidly expanded CCL22-3 specific T cell culture.
Figure 2:
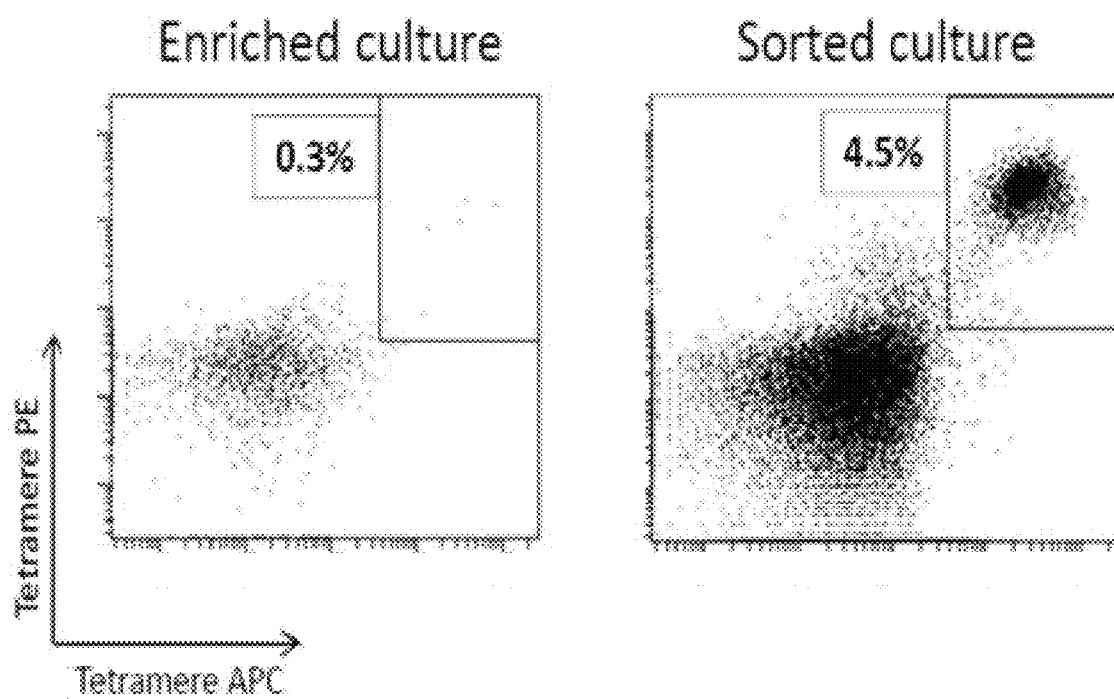

CCL22 specific cells were then isolated by tetramer staining and expanded, obtaining a clear population of CCL22-3:tetramer positive population (FIG. 2B).

The nature and reactivity of CCL22 specific T cells was evaluated by intracellular staining and it was found that CD8+ T cells were secreting IFN-γ and TNF-α in response to CCL22-3 peptide stimulation, whereas no reactivity was seen from the CD4+ T cells (FIG. 2A).

Figure 3:
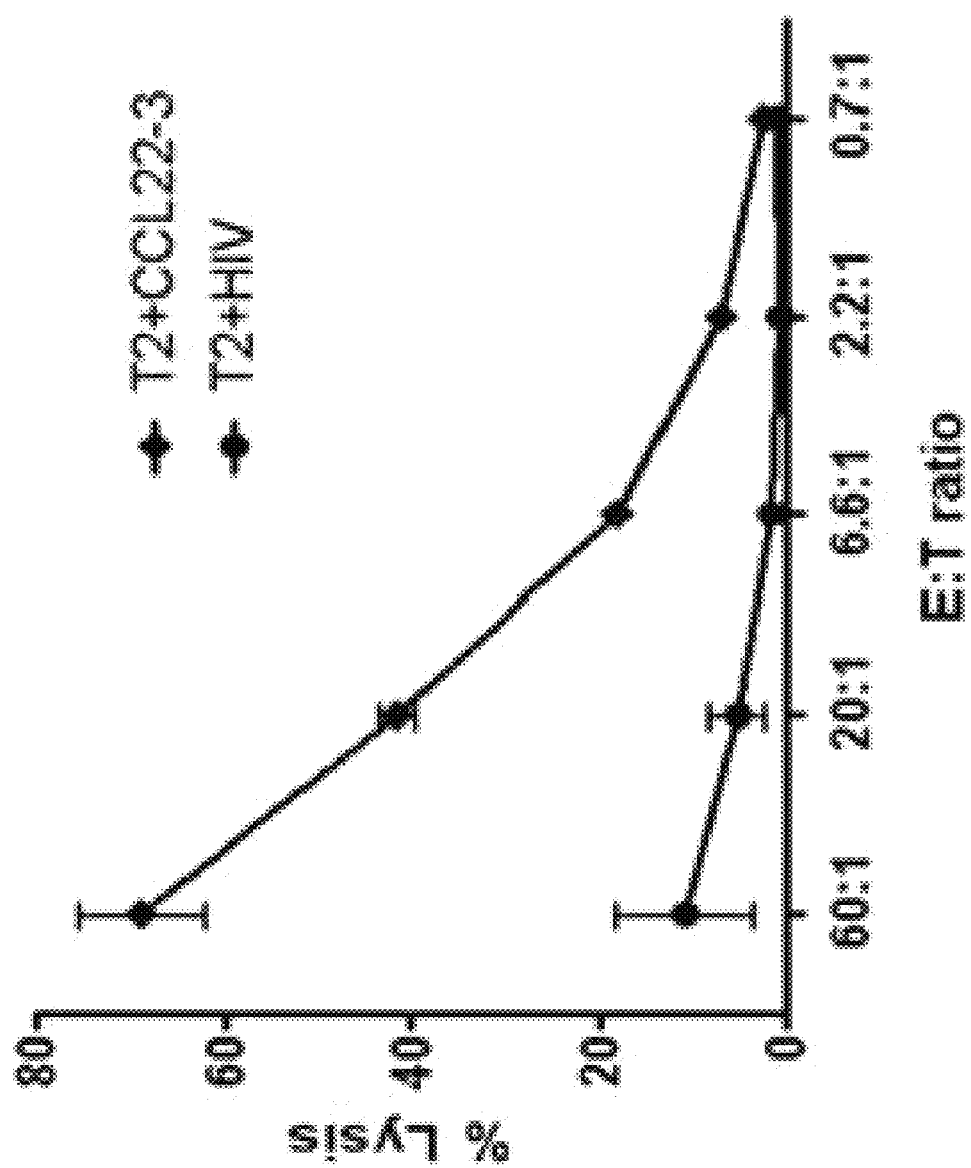
FIG. 3: CCL22 reactive T cells are cytotoxic. A—CCL22-3 but not HIV peptide pulsed T2 cells are lysed by CCL22 specific T cells. B—CCL22long peptide (SEQ ID NO: 1) is recognized by CCL22 specific T cells. Hence, T2 cells pulsed with CCL22long and CCL22-3 are recognized and killed. T2 cells pulsed with control peptide are not recognized by CCL22-specific T cells. C—Cytotoxic activity of CCL22 specific T cells is HLA dependent. Hence, K562 cells transfected with HLA-A2 and pulsed with CCL22-3 peptide are recognized and killed. K562 cells, K562 cells pulsed with CCL22-3 or K562 cells transfected with HLA-A2 are not recognized. D—CCL22-3 peptide is recognized better than 9-mer CCL22-2 peptide. Peptide titration of CCL22-3 and CCL22-2 peptides revealed that the CCL22 specific T cells cross-react but recognize CCl22-3 with higher avidity.
Figure 3:
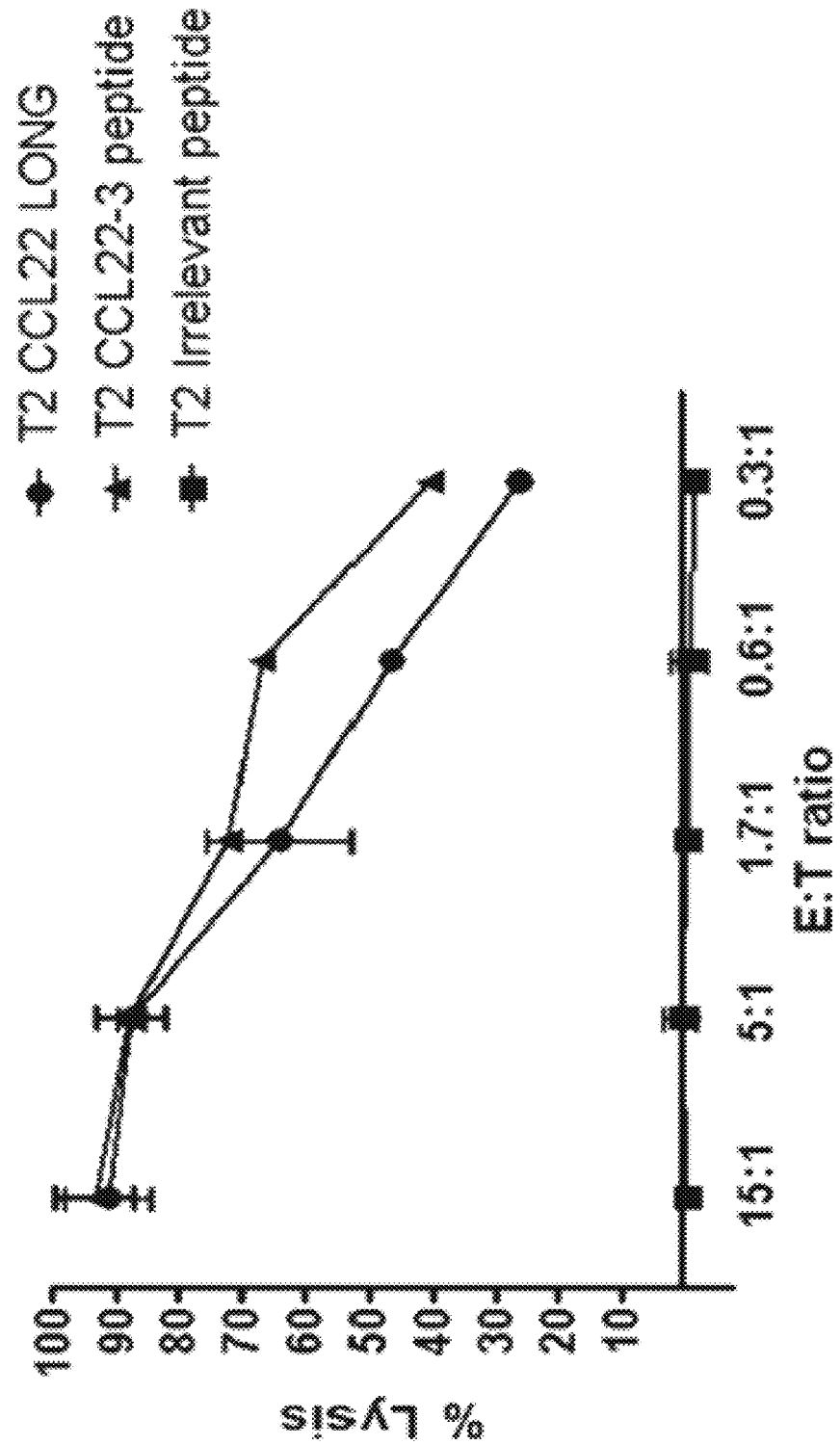
Figure 3:
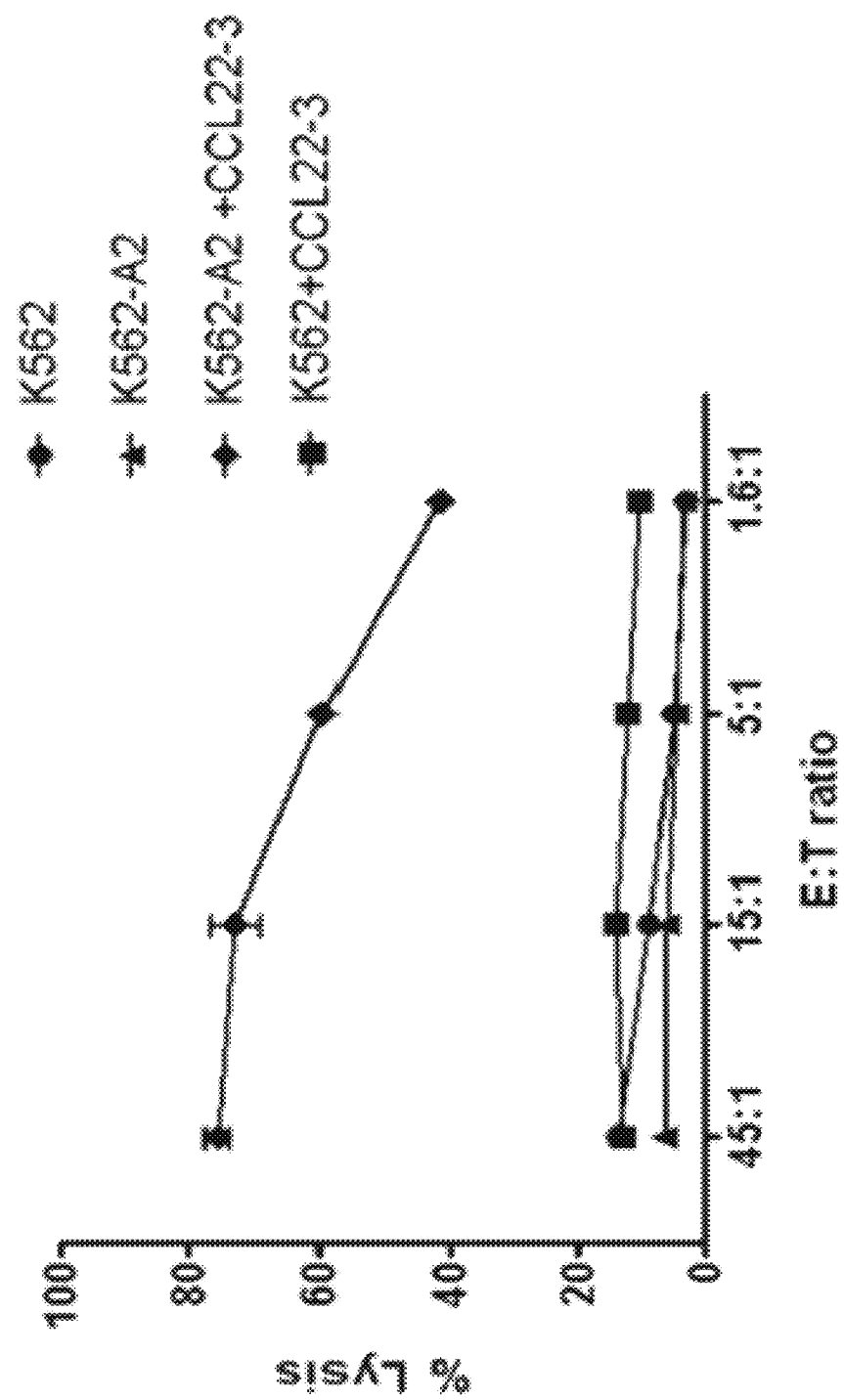
Figure 3:
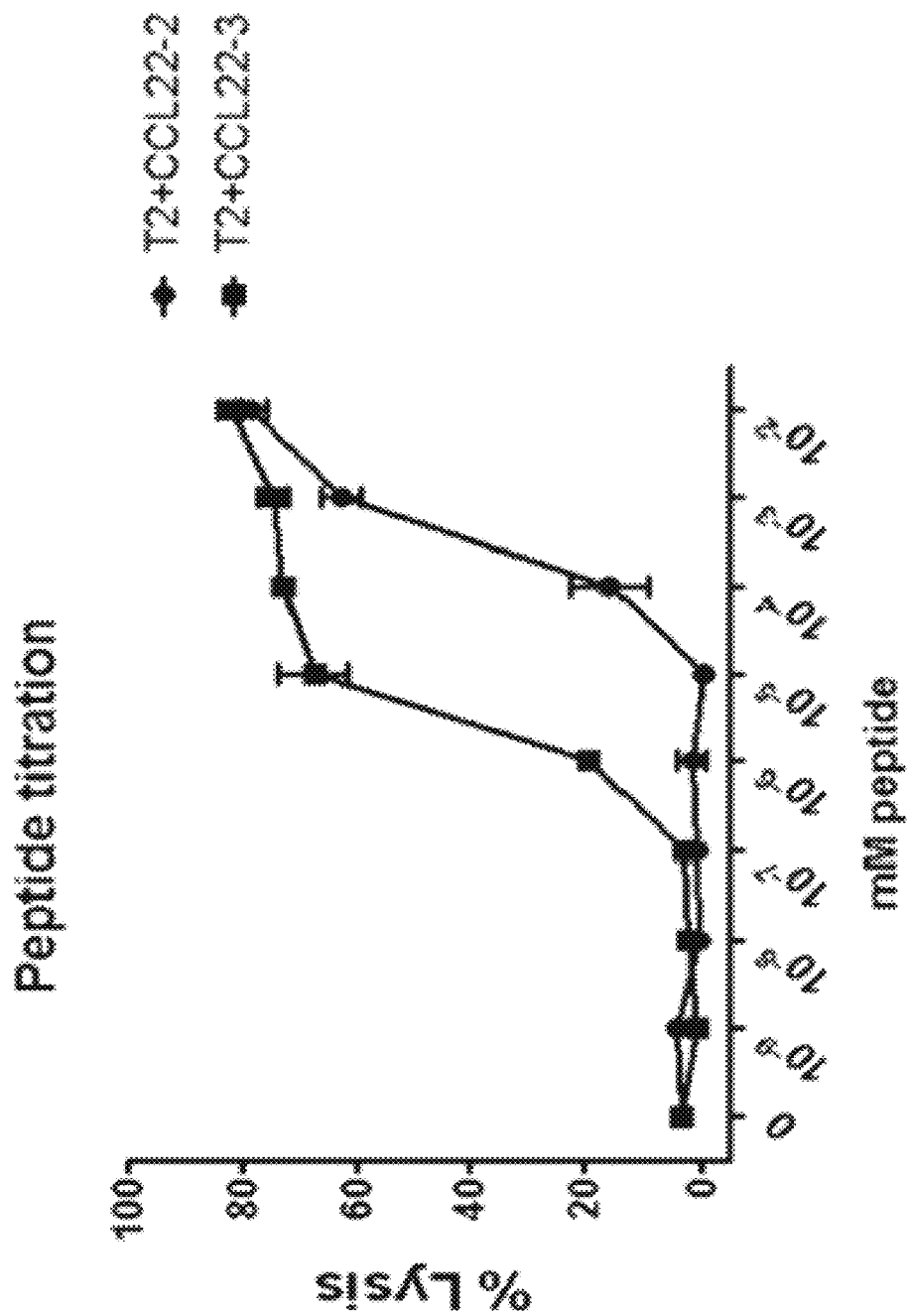

HLA-A2-restricted reactivity of CCL22-specific T cells was shown by using HLA-A2 negative and stably transfected K562 cells as targets in a chromium release assay (FIG. 3).

CCL22-specific cultures were tested for reactivity against several different cancer cells, i.e. leukemia cells (THP-1, RPM16666, UKE-1), colon cancer (SW480) as well as breast cancer (MDA).

Figure 4:
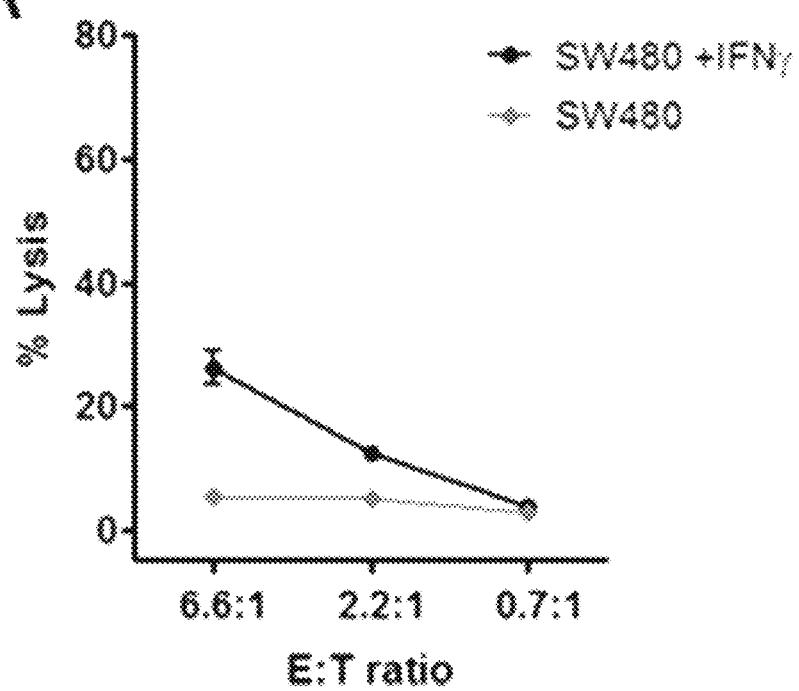
FIG. 4: CCL22-reactive T cells are able to recognize and kill CCL22-expressing cancer cell lines. $^{51}$Cr release assays of IFNγ non-treated or pretreated cancer cell lines: SW480—colorectal adenocarcinoma (A); MDA-MB-231—breast adenocarcinoma (B); Uke-1—acute myeloid leukemia (C); THP-1—acute monocytic leukemia (D); RPM16666—Hodgkin's lymphoma (E); Set-2—essential thrombocytemia (F). The same effector CCL22-specific T cell culture was used as effector cells. G—Lysis of IFNγ induced THP-1 cells transfected with CCL22 siRNA transfection or Mock transected by CCL22-specific T cells. Assay performed 48 h after transfection. H—ELISA analysis of CCL22 expression in the supernatant from siRNA transfected THP-1 cells compared to THP-1 cells transfected with Mock control, 48 h after electroporation.
Figure 4:
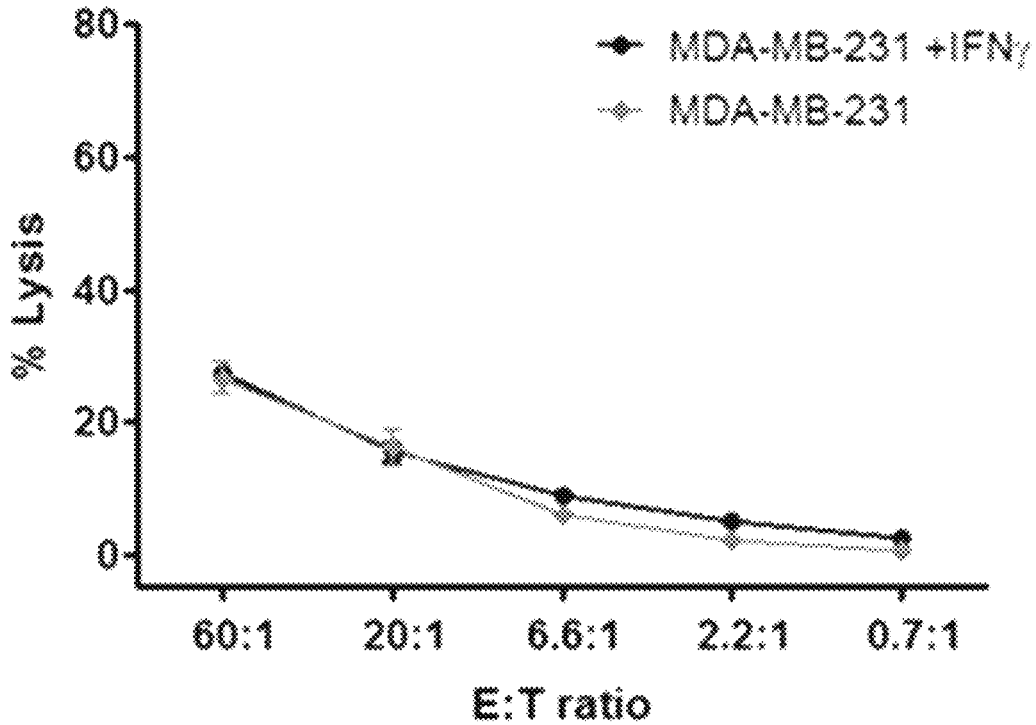
Figure 4:
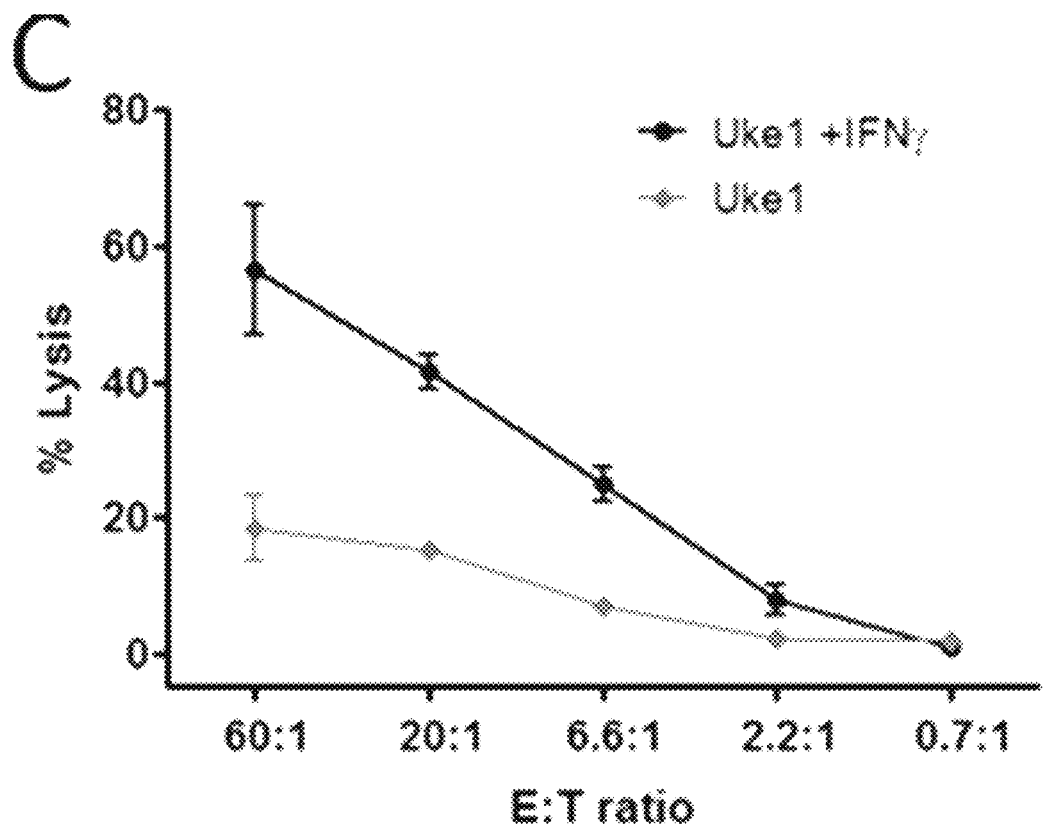
Figure 4:
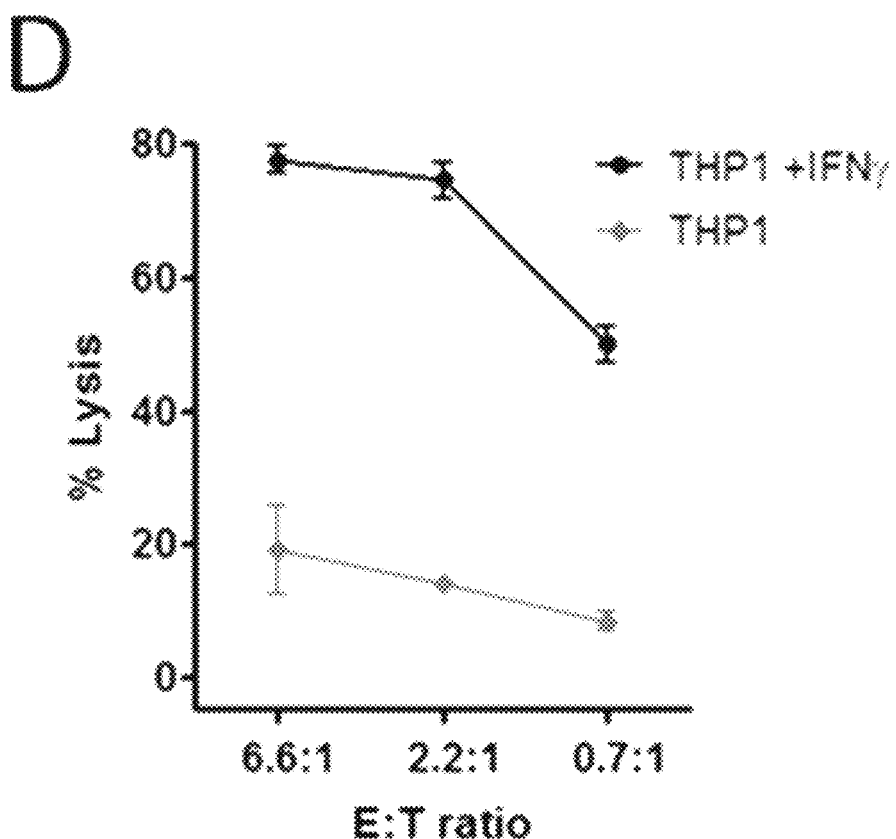
Figure 4:
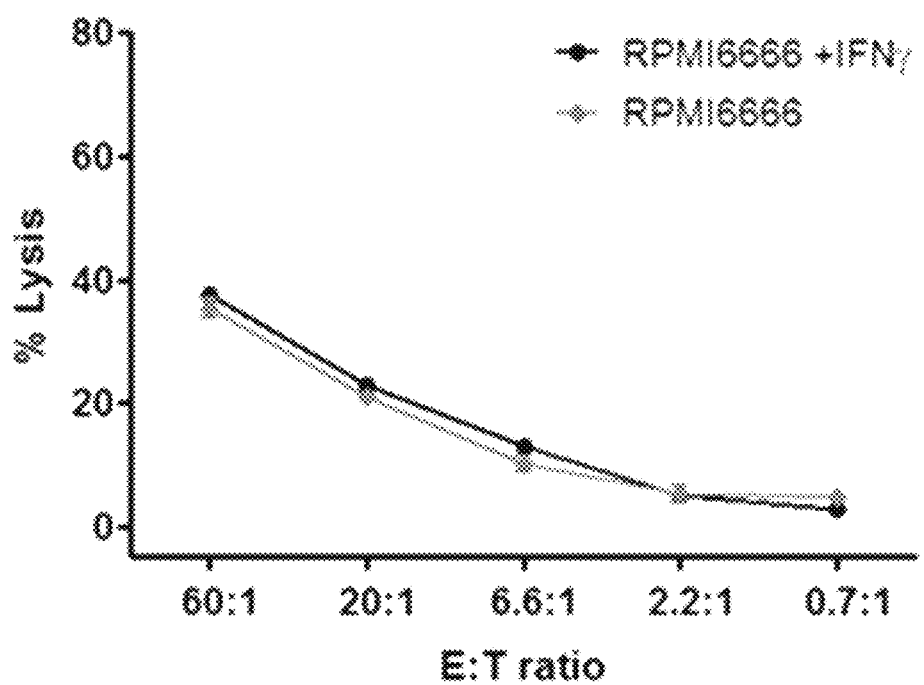
Figure 4:
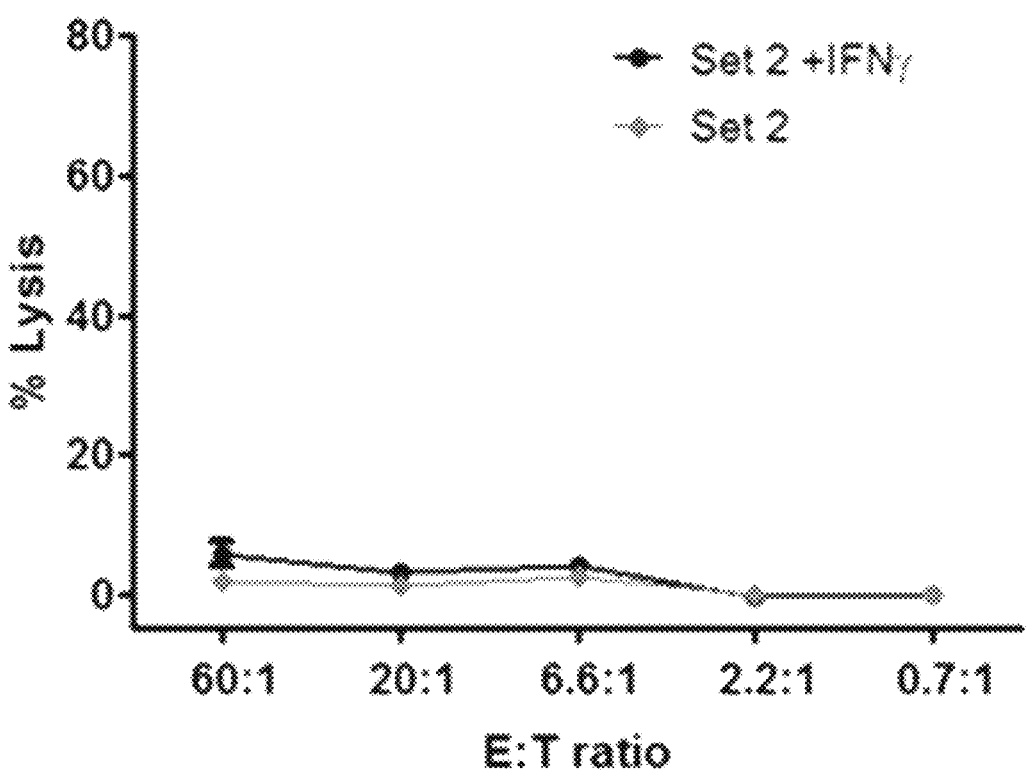
Figure 4:
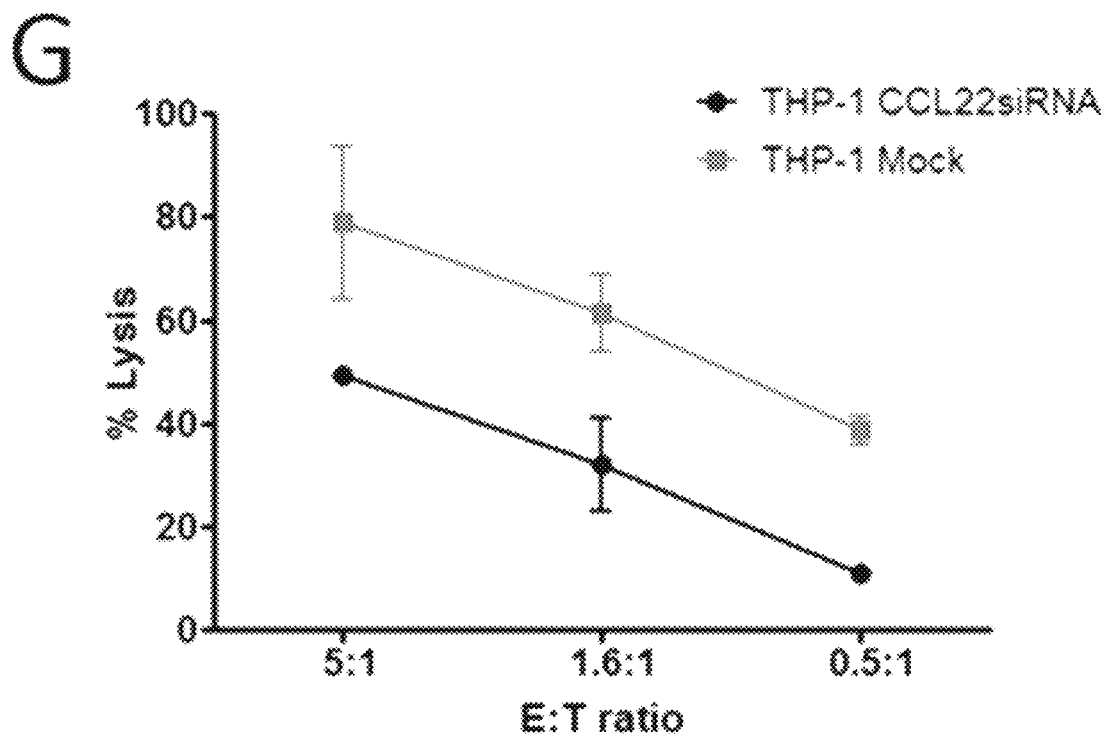
Figure 4:
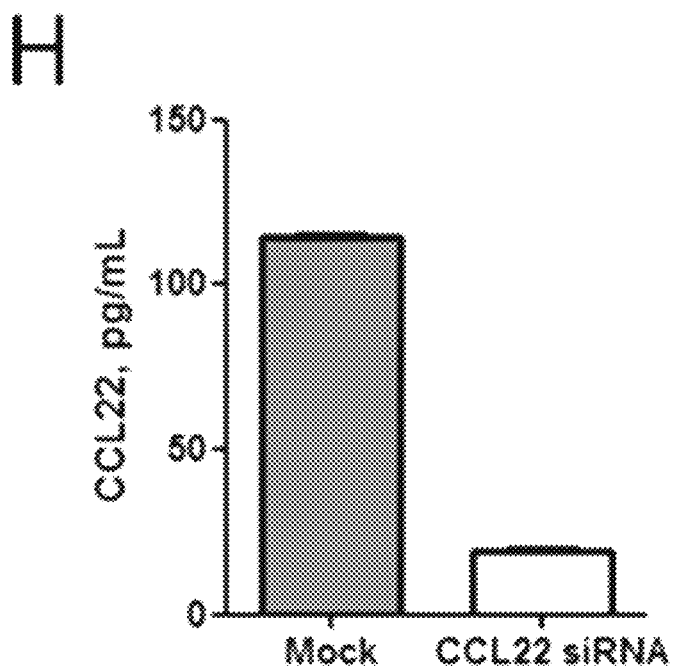

T cells reactive to CCL22-3 were able to recognize and lyze CCL22 expressing cancer cell lines, as shown by chromium release assay (FIG. 4). We also found that CCL22-peptide specific cells were able to lyse various cancer cell lines with and without treatment with IFN-γ (FIG. 4).

Figure 5:
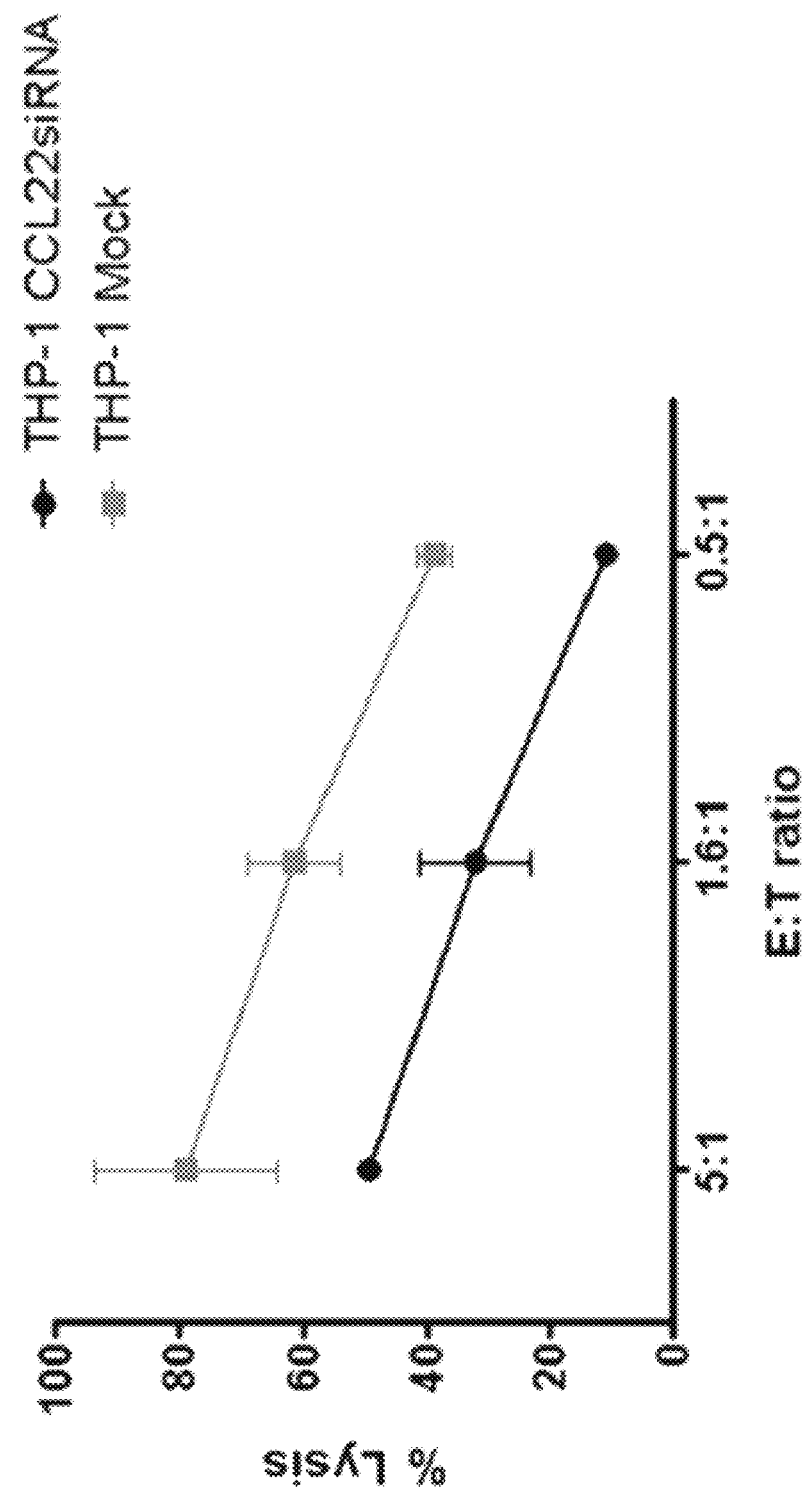
FIG. 5: CCL22 specific T-cell cytotoxicity is CCL22 dependent. A—CCL22 specific T-cell cytotoxicity decreases with lower expression of CCL22. Thus, the lysis of CCL22 siRNA transfected THP-1 cells is lower than that of Mock transfected cells. B ELISA analysis of CCL22 expression in supernatant of THP-1 cells 48 h after siRNA transfection. C—CCL22 specific T cells recognize dendritic cells in a CCL22 dependent manner. Hence, using flow cytometry, the release of TNF-a and CD107a was examined when incubating CCL22 specific T cells with autologous dendritic cells without and with transfection with CCL22 siRNA.
Figure 5:
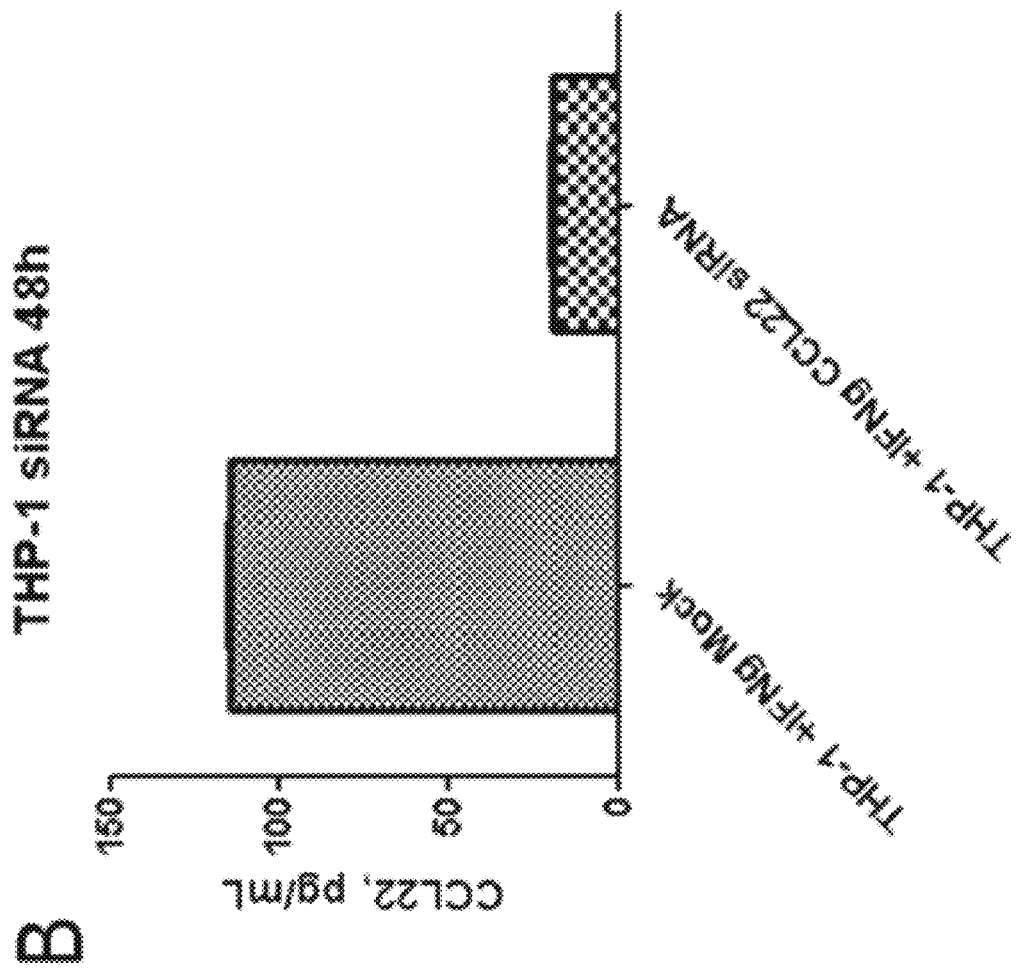
Figure 5:
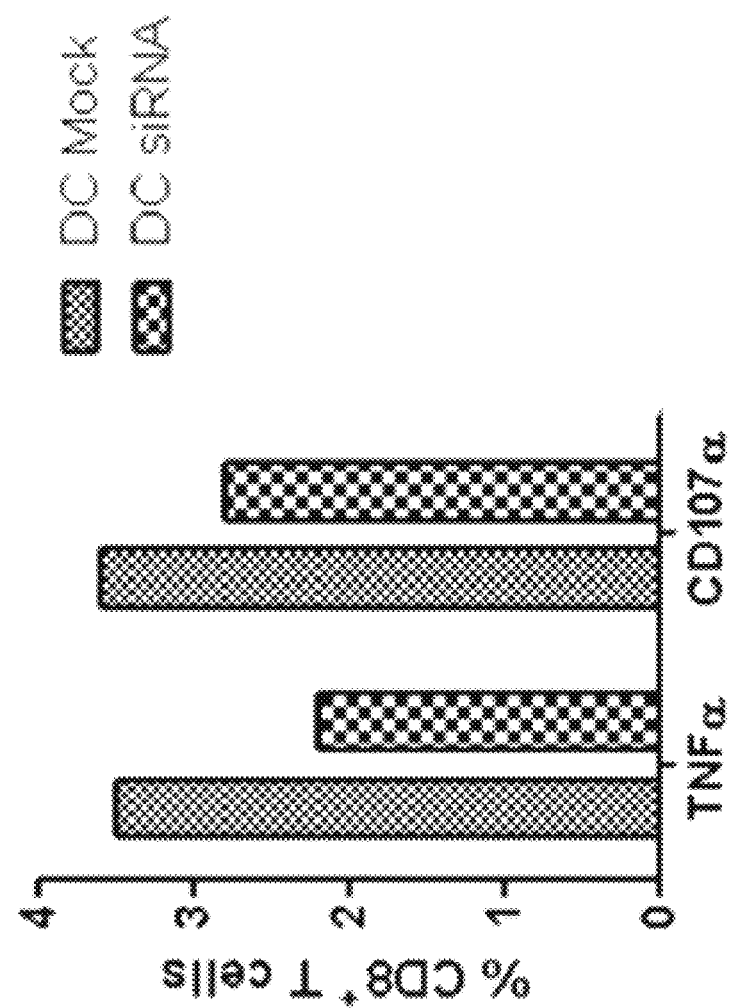
Figure 6:
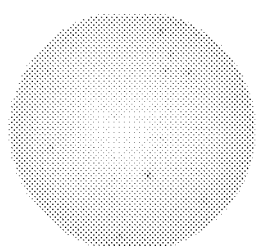
FIG. 6: Spontaneous CCL22-3 response peripheral blood of healthy donor. A—Example of ELISPOT response from PBMCs of a healthy donor without and with CCL22-3 peptide as shown by IFNγ ELISPOT. B—CCL22 expression in supernatant from PBMC from the same donor after stimulation with IL-2 either with CCL22-3 peptide or HIV control peptide. C—IL6 and TNFα in supernatant from PBMC from the same donor after stimulation with IL-2 either with CCL22-3 peptide or HIV control peptide after peptide stimulation. D—CCL22 expression in IL-2 stimulated PMBC supernatant from PBMC from the same donor after either CCL22-3/HLA-A2 tetramer enrichment (left) or CCL22-3/HLA-A2 tetramer depletion (right).
Figure 6:
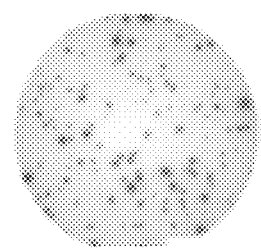
Figure 6:
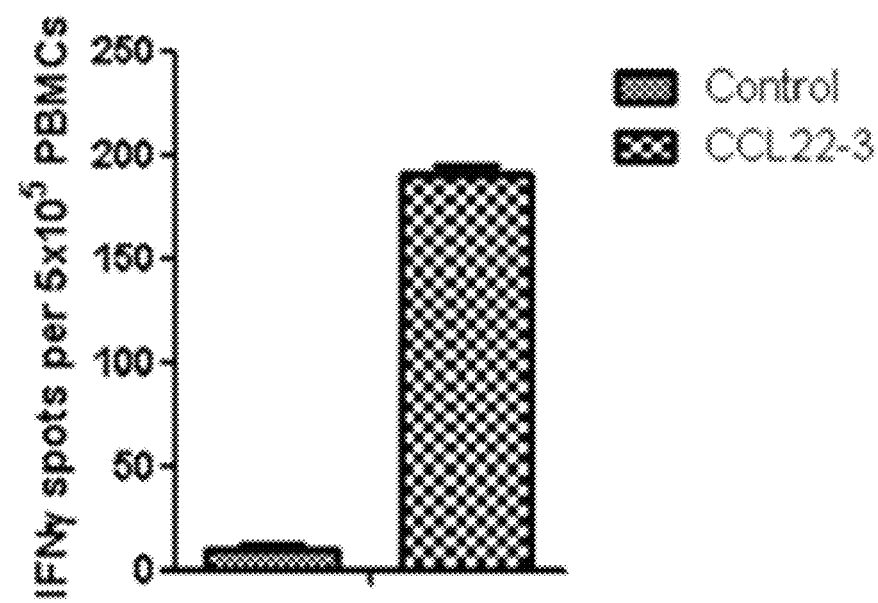
Figure 6:
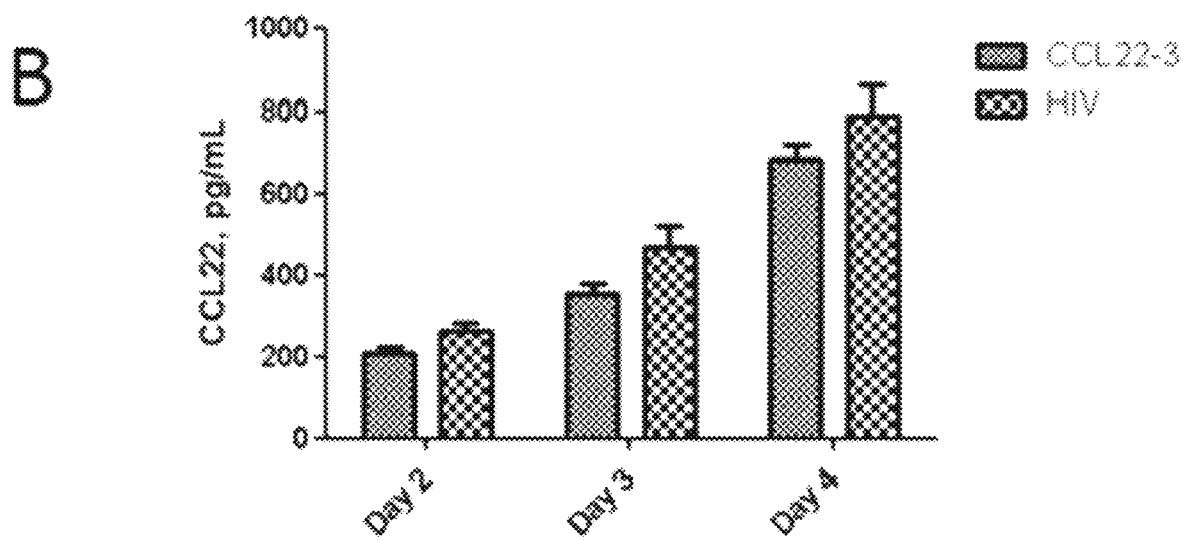
Figure 6:
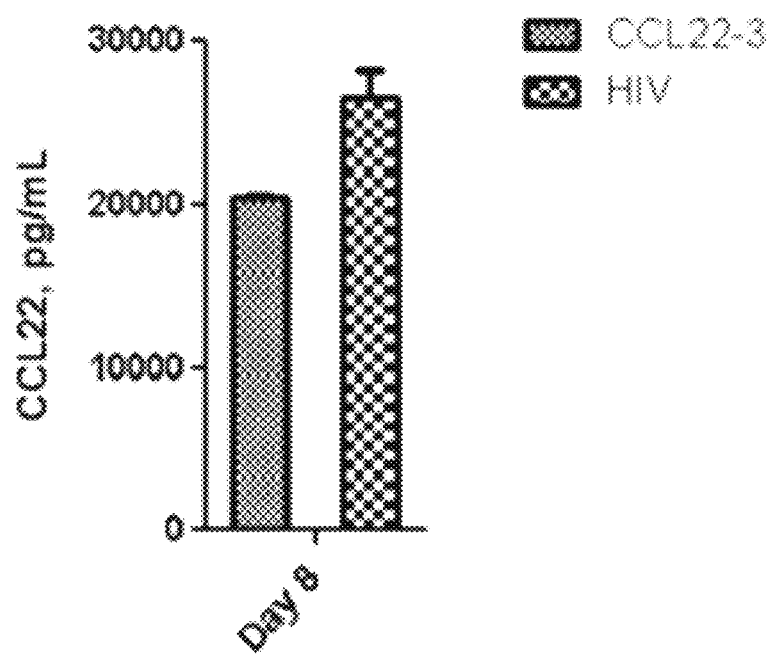
Figure 6:
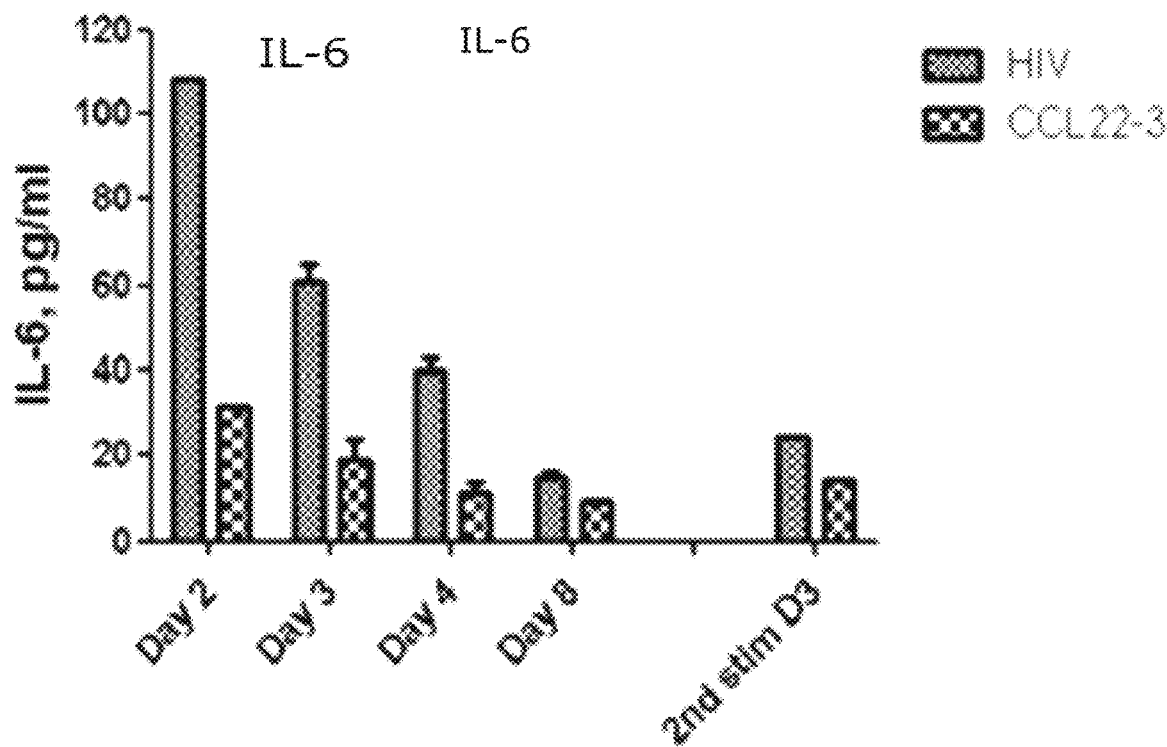
Figure 6:
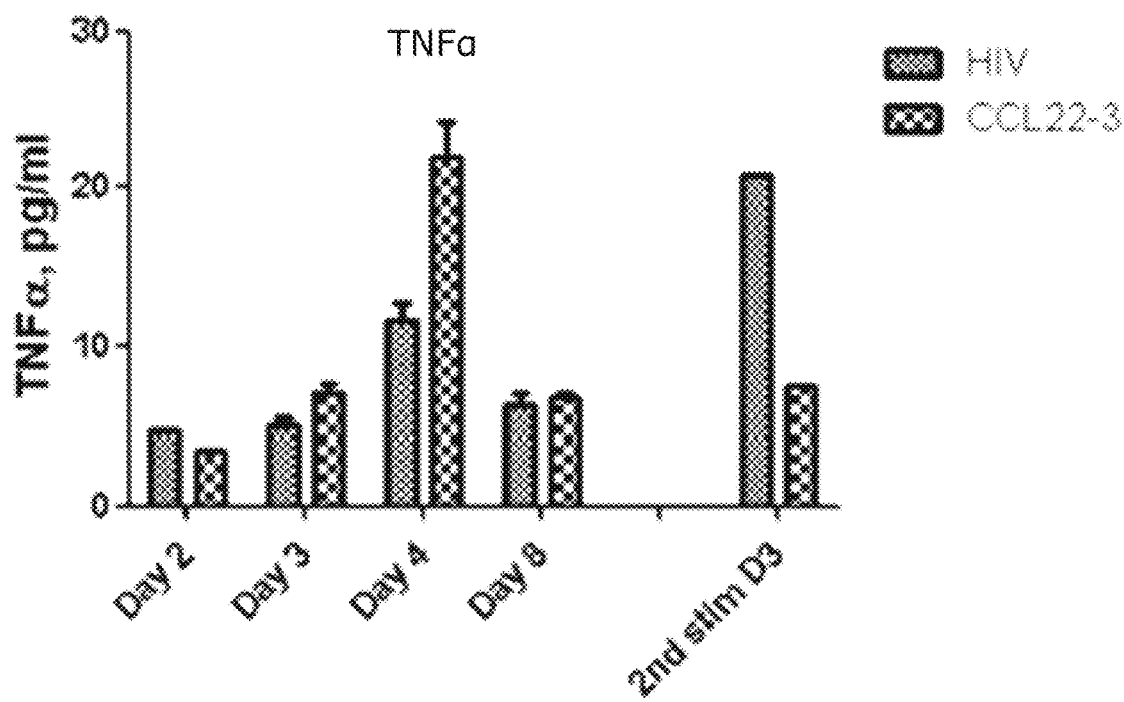
Figure 6:
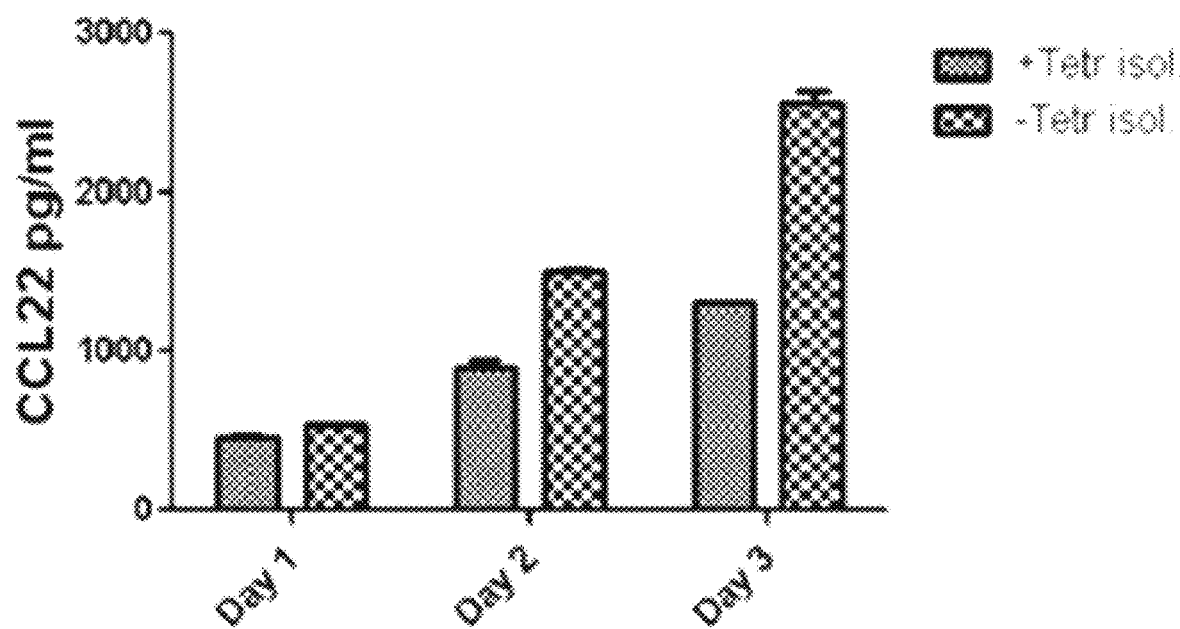
Figure 6:
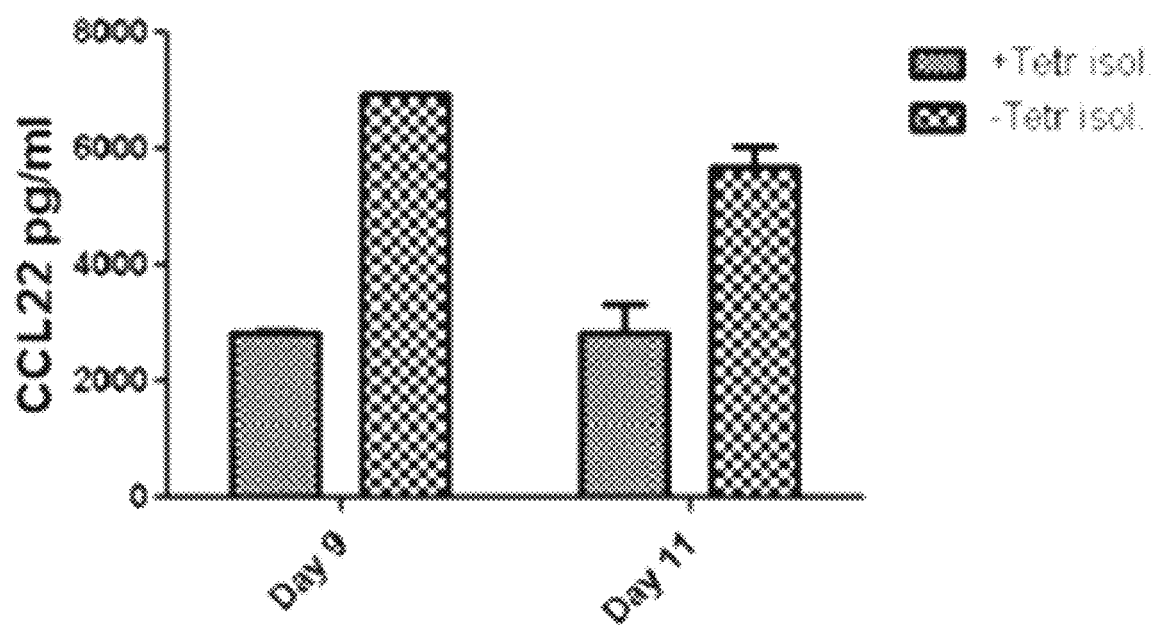
Figure 7:
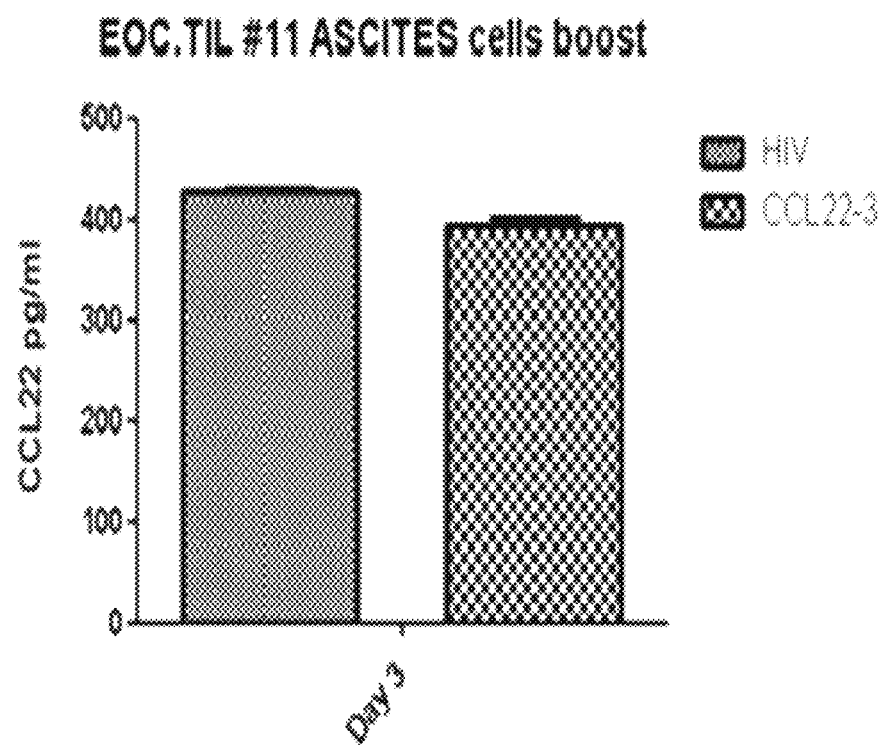
FIG. 7: CCL22 expression levels by ovarian cancer ASCITES cells are affected by addition of CCL22-3 peptide. ELISA analysis of supernatants after 2 days (A) and 7 days (B) of cell culture of ASCITES cells isolated from a patient with ovarian cancer stimulated with CCL22-3 or HIV peptides with the addition of IL2.
Figure 7:
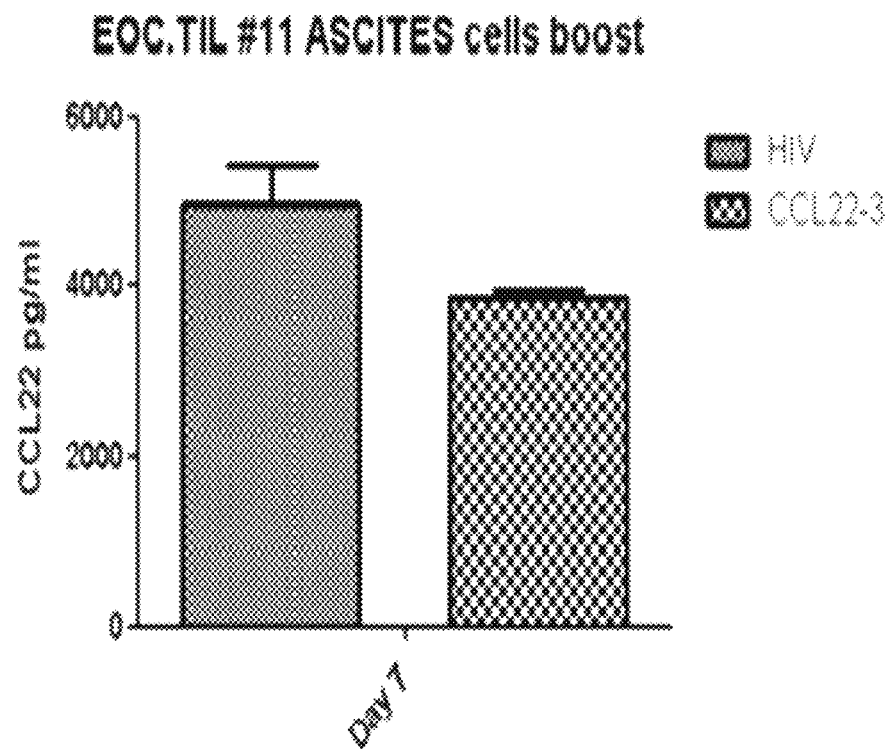

The killing of target cells by CCL22-specific T cells was dependent of the CCL22 expression by the target cells. Thus, decreased CCL22 expression by siRNA transfection of THP-1 cells decreased the T-cell mediated lysis (FIG. 5).

Example 3—CCL22-Specific T Cells

We screened the amino acid sequence of human CCL22 protein for possible HLA-A2-binding peptide epitopes using the SYFPEITHI epitope prediction algorithm available at www.syfpeithi.de. Interestingly, all high-scoring epitopes were located in the signal peptide portion of the sequence, which is cleaved off before the protein is secreted. One of the high-scoring CCL22-derived peptides was RLQTALLVVL, hereafter referred to as $pCCL22_{3-12}$. To characterize $pCCL22_{3-12}$-specific T cells, we acquired PBMCs from a melanoma patient, and stimulated these cells using autologous DCs or PBMCs pulsed with the $pCCL22_{3-12}$ peptide. After five stimulations, we performed $pCCL22_{3-12}$-tetramer staining, which revealed small but distinct population of tetramer-positive cells (FIG. 2A, left). The tetramer-positive populations were successfully isolated and expanded using the rapid expansion protocol (FIG. 2B, right). On the expanded culture, we performed intracellular staining for INFγ and TNFα in response to peptide stimulation. Around 30% of CD8+ cells secreted IFNγ and TNFα in response to $pCCL22_{3-12}$ peptide stimulation (FIG. 2A). Only CD8+ T cells secreted INFγ and TNFα in response to the $pCCL22_{3-12}$ peptide, with no response detected from CD4+ T cells. The same results were found with intracellular staining before tetramer isolation and expansion (data not shown).

Example 4—$pCCL22_{3-12}$-Specific T Cells Exhibit HLA-A2-Restricted Killing

Next, we examined the cytotoxic capability of CCL22-specific T cells. The $pCCL22_{3-12}$-specific T cells were able to lyse $pCCL22_{3-12}$-pulsed T2 cells, but did not recognize T2 cells pulsed with a negative control peptide from HIV (FIG. 3A). To confirm the HLA-A2-restricted reactivity of CCL22-specific T cells, we used HLA-A2-transfected K562 cells pulsed with and without $pCCL22_{3-12}$ as targets (FIG. 3B), and found that the T cells only recognized the K562-A2 cells pulsed with $pCCL22_{3-12}$. As an additional control, we examined non-transfected HLA-negative K562 cells, determining that these cells were not recognized by the $pCCL22_{3-12}$-specific T cells even when pulsed with $pCCL22_{3-12}$.

We further examined whether the $pCCL22_{3-12}$ epitope could be cross-presented from the 22-mer signal peptide sequence of the CCL22 protein (termed the CCL22-signal peptide; MDRLQTALLVVLVLLAVALQAT). Indeed, $pCCL22_{3-12}$-specific T cells lysed the T2 cells that were pulsed with CCL22-signal peptide (FIG. 3C), indicating that T2 cells could cross-present the $pCCL22_{3-12}$ epitope even without TAP expression in these cells. We then examined the T-cell avidity of $pCCL22_{3-12}$-specific T cells towards the $pCCL22_{3-11}$ peptide (RLQTALLVV), which is one amino acid shorter than $pCCL22_{3-12}$ and was predicted by the computer algorithm to bind to HLA-A2 with high affinity. Although the T cells reacted towards both peptides, they showed the highest avidity towards the decamer $pCCL22_{3-12}$ epitope (FIG. 3D).

Example 5—Cytotoxicity Against CCL22-Expressing Cancer Cells

The CCL22-specific cytotoxic T-cell lymphocyte (CTL) culture was tested for reactivity against the leukemia cell lines THP-1, RPM16666, UKE-1, and SET-2; the colon cancer cell line SW480; the breast cancer cell line MDA; and the melanoma cell line FM55-M2. PCR analysis revealed CCL22 expression in all of these cell lines except for FM55-M2 (data not shown), although SET-2 showed only a weak band. We found that $pCCL22_{3-12}$-specific cells lysed most of the investigated cancer cell lines, both with and without pre-treatment with interferon-gamma (IFN-γ) (FIG. 4A-E). IFN-γ reportedly induces CCL22 expression in cancer cell lines, and increases surface expression of HLA. Chromium release assay revealed that SET-2 cells were not killed, which were only weakly positive for CCL22 mRNA on PCR (FIG. 4F). Additionally, the melanoma cell line FM55-M2 showed no CCL22 mRNA on PCR, and these cells were not lysed by CCL22-specific CTLs (data not shown). To confirm that the killing of cancer cells by CCL22-specific CTLs was indeed dependent on CCL22 expression, we used siRNA transfection to inhibit CCL22 expression in IFNγ pre-treated THP-1 cells. This transfection rescued these cells from T-cell mediated lysis (FIG. 4G). FIG. 4H depicts the CCL22 inhibition in THP-1 cells after siRNA transfection as measured by ELISA from the supernatant.

Example 6—Spontaneous T-Cell Responses Against CCL22

Figure 8:
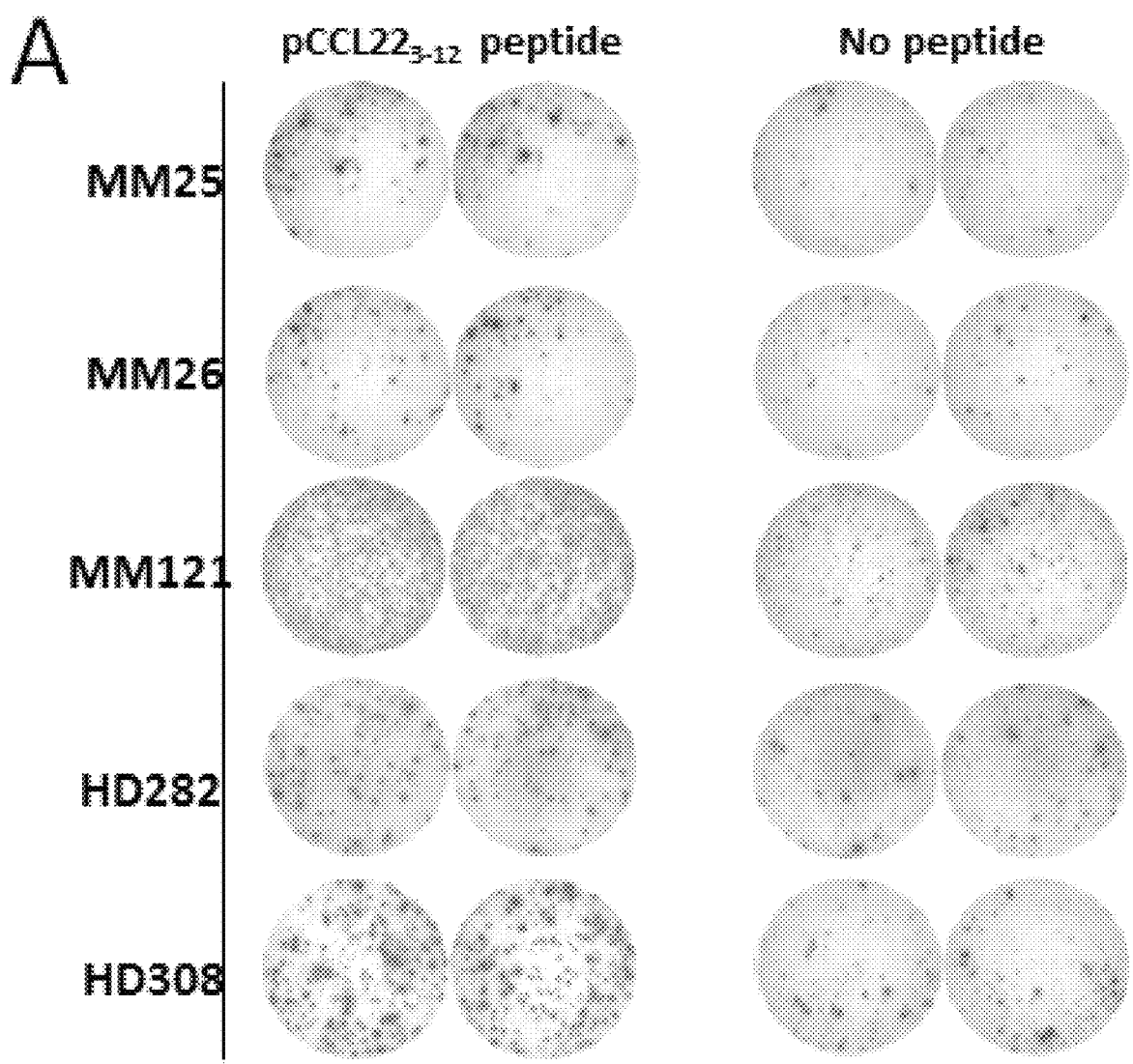
FIG. 8: $CCL22_{3-12}$-reactive T cells are present in healthy donors and cancer patients. A—IFNγ ELISPOT examples showing T-cell responses against the $pCCL22_{3-12}$ epitope in three melanoma patients (MM) and two healthy donors (HD). B—$pCCL22_{3-12}$ peptide specific IFNγ ELISPOT responses in cancer patients and healthy donors The average number of $pCCL22_{3-12}$-specific spots (after subtraction of spots in wells without added peptide) was calculated per $3 \times 10^5$ PBMC for each donor. C—Experimental setup of $pCCL22_{3-12}$-specific T-cell depletion/enrichment in PBMCs. PBMCs from a healthy donor were stimulated twice with $pCCL22_{3-12}$ peptide before the $pCCL22_{3-12}$-specific T cells (anti-CCL22 T cells) were isolated using $pCCL22_{3-12}$-PE-tetramer in combination with anti-PE magnetic beads. The remaining depleted PBMCs were divided into two cultures before $pCCL22_{3-12}$-tetramer isolated cells were added into one of these resulting in a tetramer-enriched culture. CCL22-specific T cells in a tetramer-enriched culture target CCL22 producing T cells (as indicated by black arrows). D—ELISA analysis of CCL22 in the supernatants from $pCCL22_{3-12}$-tetramer-enriched compared to tetramer-depleted PBMC cultures over time.
Figure 8:
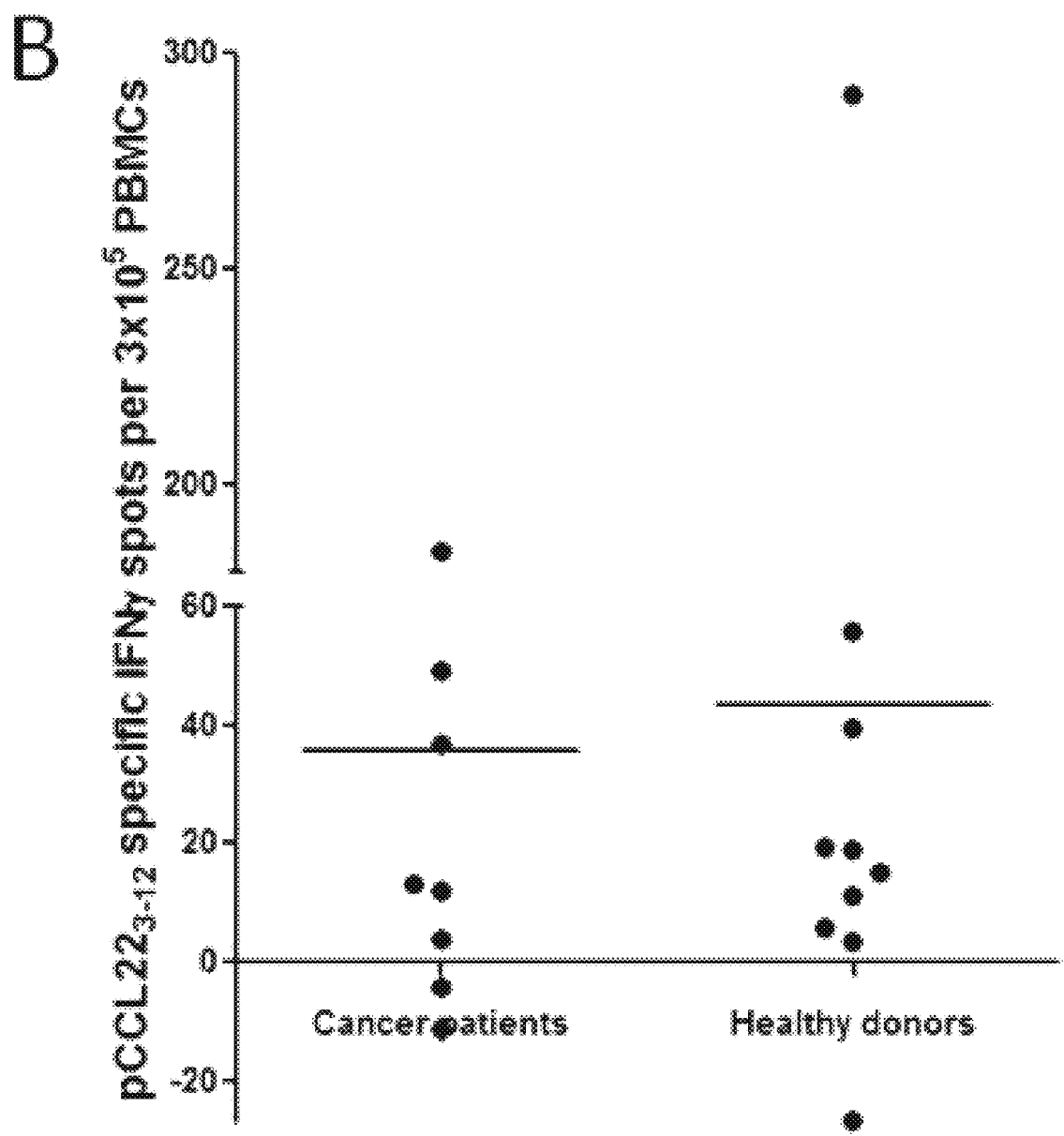
Figure 8:
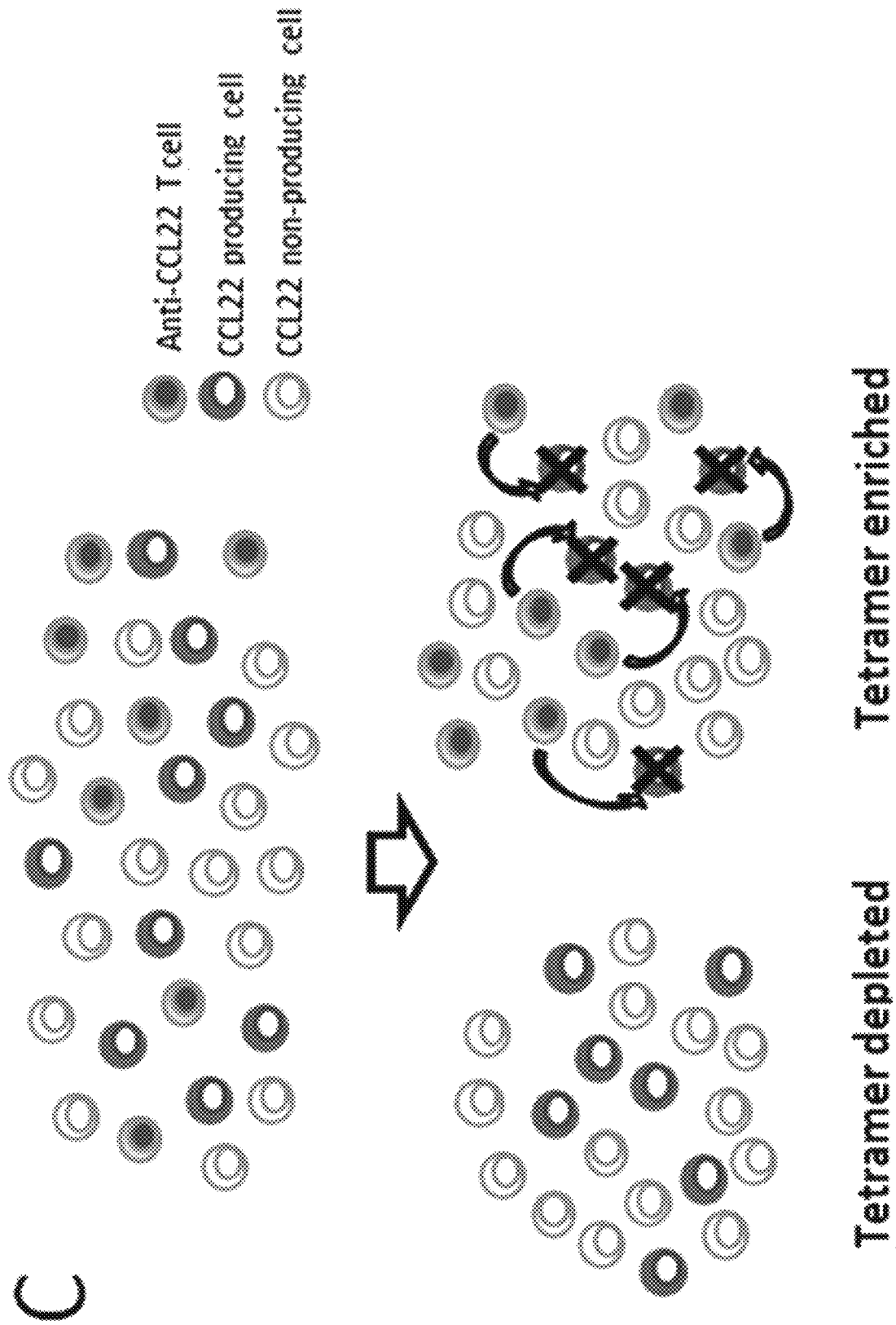
Figure 8:
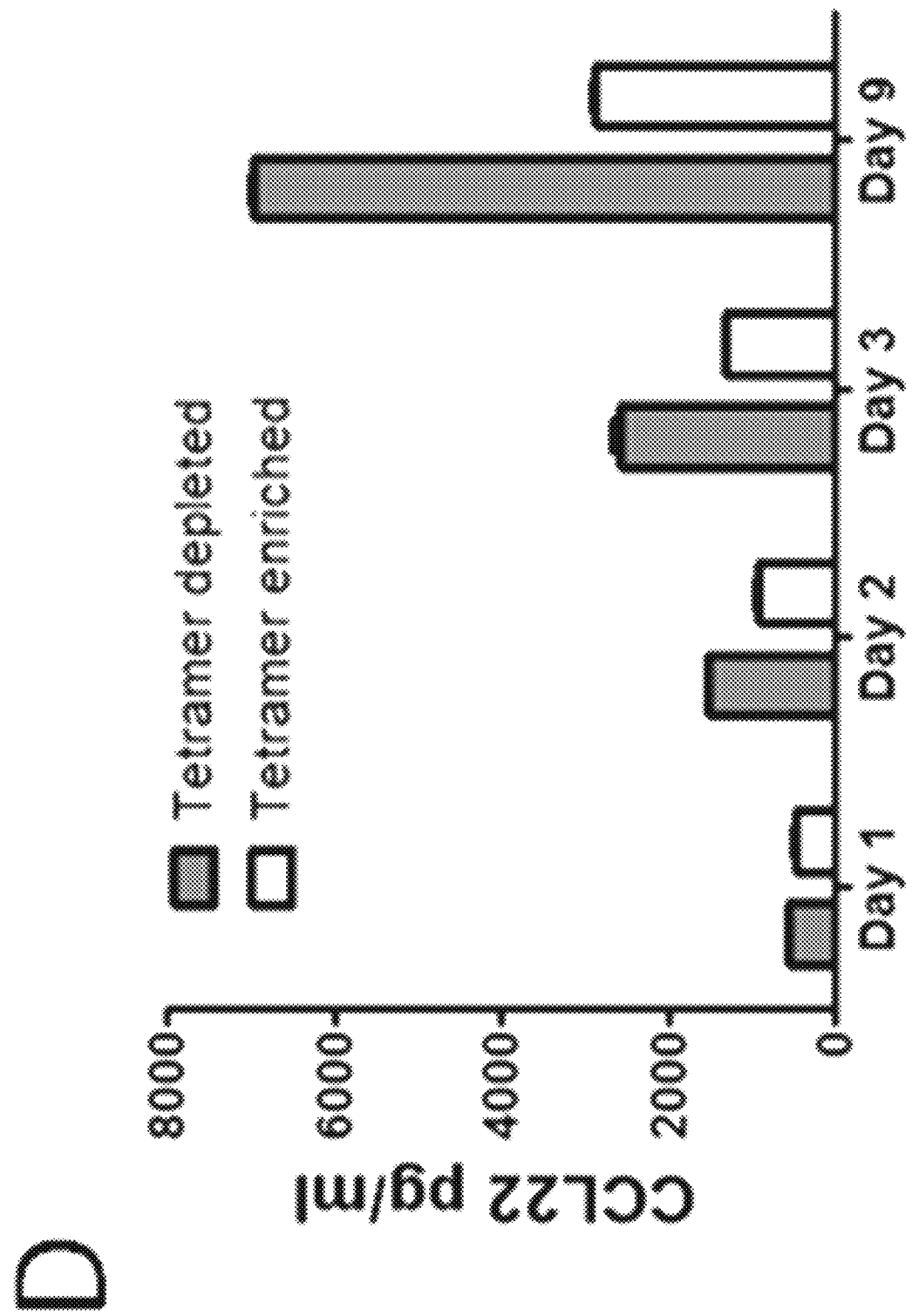

We next acquired PBMCs from 13 cancer patients and 10 healthy individuals, and stimulated these cells with the pCCL22$_{3-12}$ peptide for two weeks in the presence of low-dose IL-2. We used the IFN-γ Enzyme-Linked Immuno-SPOT (ELISPOT) assay to analyze the reactivity towards the pCCL22$_{3-12}$ peptide. Spontaneous specific T-cell reactivity against pCCL22$_{3-12}$ was detected in a number of melanoma patients and healthy donors (FIG. 8A). Notably, the overall responses appear to be similar in healthy donors and cancer patients (FIG. 8B).

Example 7—T-Cell-Mediated Decrease in CCL22 Levels in the Microenvironment

Donor PBMCs that showed a pCCL22$_{3-12}$ response in ELISPOT were then stimulated twice with pCCL22$_{3-12}$ peptide in the presence of IL2. Next, the culture was depleted of pCCL22$_{3-12}$-reactive T cells using HLA-A2/pCCL22$_{3-12}$-tetramer and magnetic beads. This T-cell-depleted culture was divided into two portions, and the HLA-A2/pCCL22$_{3-12}$-tetramer-isolated T cells were added back to one of the portions (FIG. 8C). We then monitored the CCL22 concentration in the supernatants of both cultures. Notably, CCL22 levels were lower in the culture with added pCCL22$_{3-12}$-specific T cells after only one day, and this difference increased over the culturing time. After nine days of culture, the CCL22 concentration was almost three times higher in the tetramer-depleted culture compared to in the tetramer-enriched culture (FIG. 8D).

Figure 9:
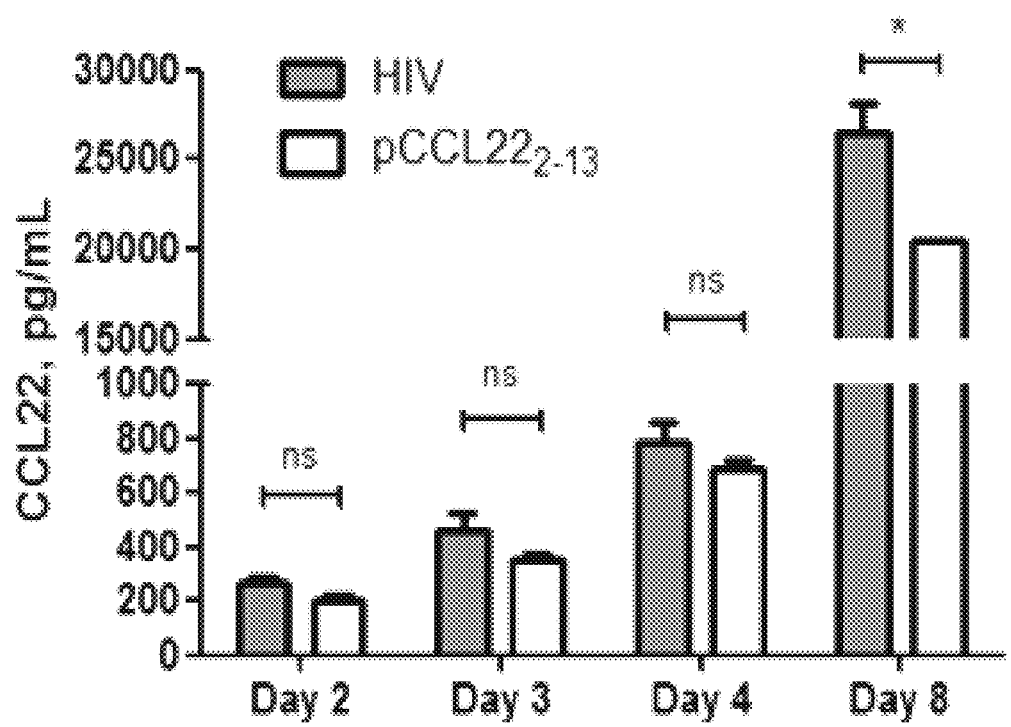
FIG. 9: Activation of CCL22-specific T cells decreases with CCL22 levels in the microenvironment. A—CCL22 levels in supernatants from PBMC isolated from a healthy donor after stimulation with either $pCCL22_{3-12}$ or HIV peptide as measured by CCL22 ELISA (*, P=0.01, ns—not significant, t-test). Experiments were performed in triplicates for each peptide. B—Changes in CCL22 levels in supernatants from PBMC isolated from 11 healthy donor PBMCs after stimulation with $pCCL22_{3-12}$ peptide compared to HIV control peptide as measured by CCL22 ELISA on day 7. C—Changes in CCL22 levels in in supernatants from PBMC isolated from 13 cancer patients after stimulation with $pCCL22_{3-12}$ peptide compared to HIV control peptide as measured by CCL22 ELISA on day 7). Experiments were performed in triplicates or duplicates for each peptide. D—CCL22 levels in supernatants from cells isolated from ovarian cancer ascites isolated from two ovarian cancer patients after stimulation with either $pCCL22_{3-12}$ or HIV peptide as measured by CCL22 ELISA.
Figure 9:
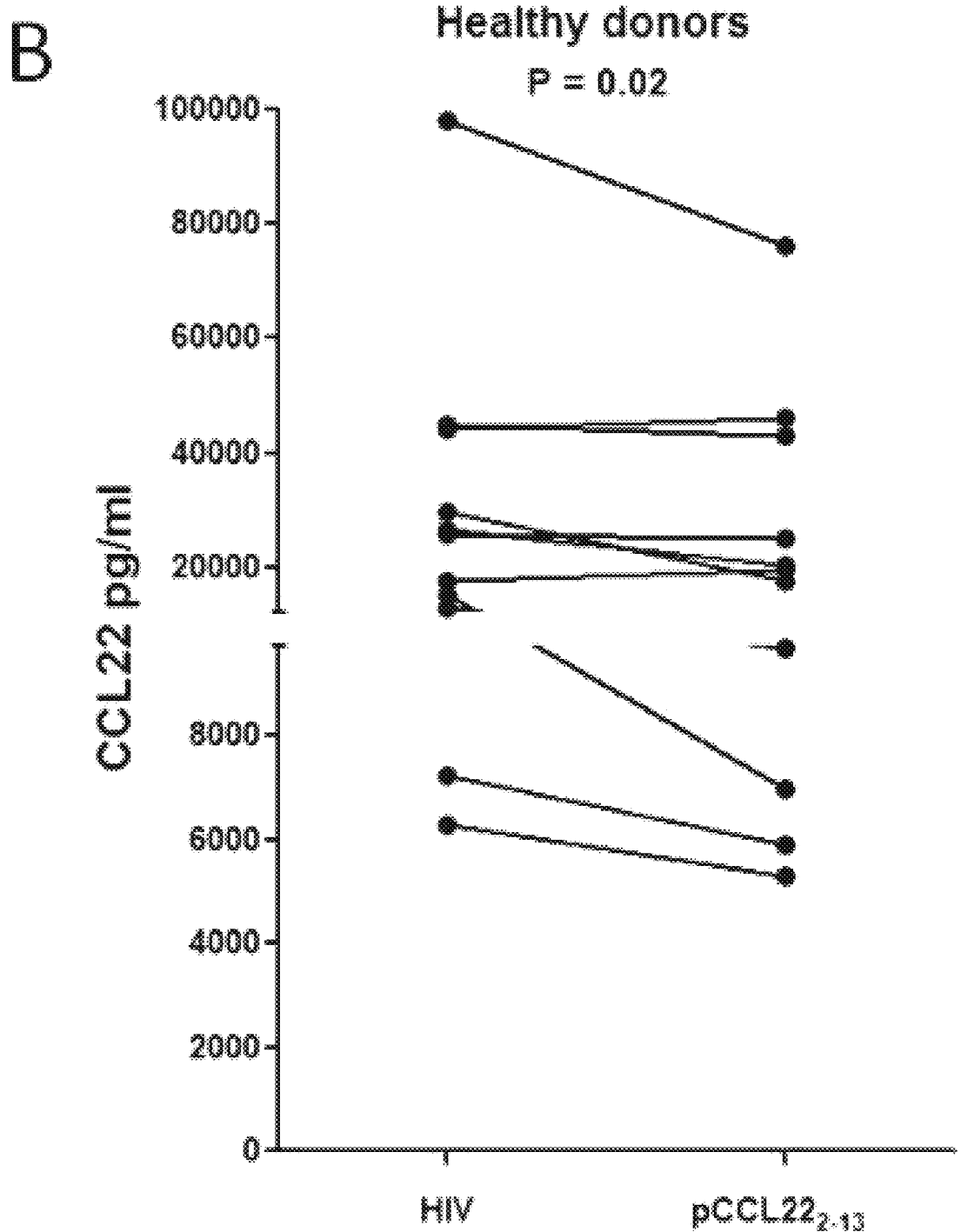
Figure 9:
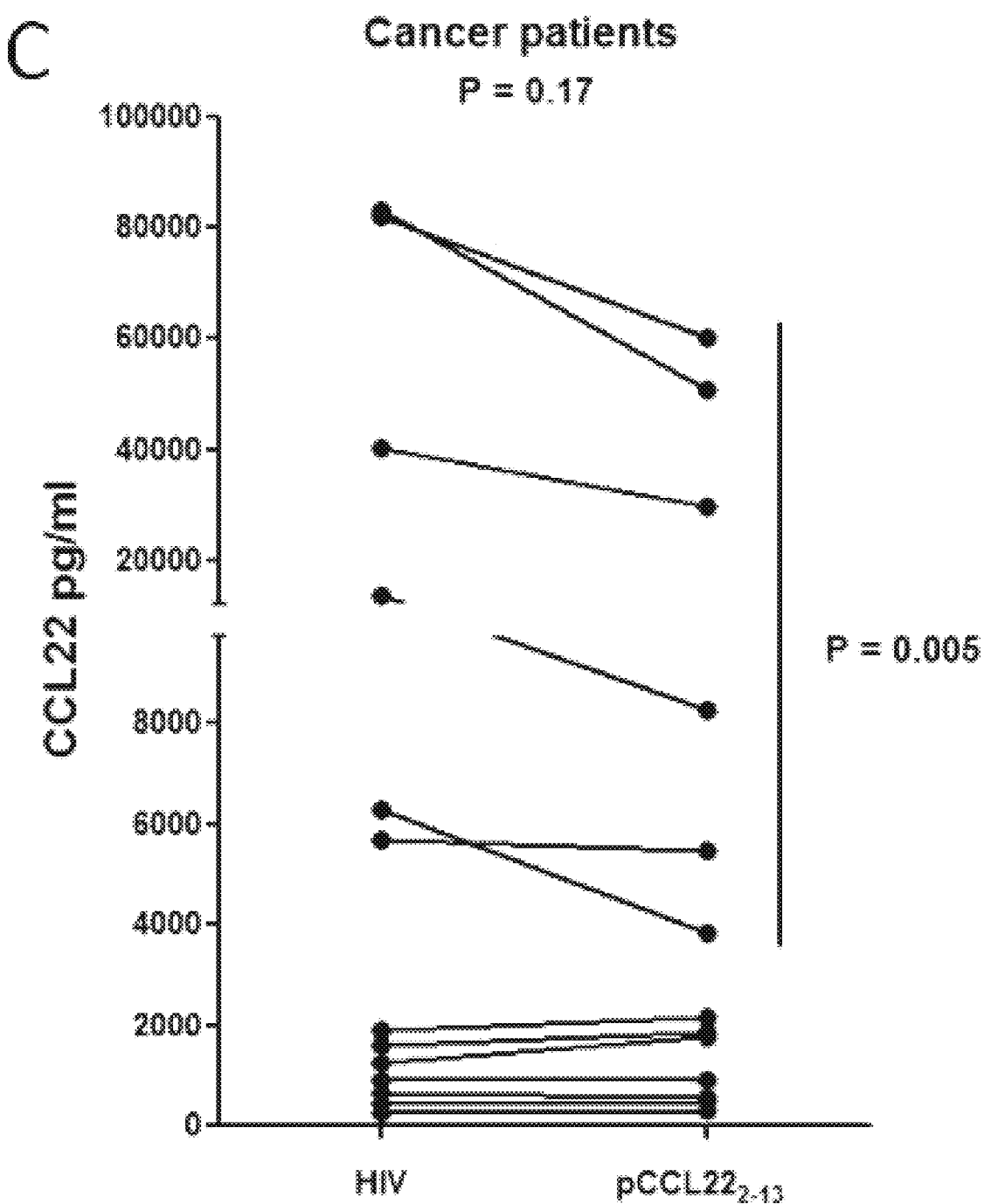
Figure 9:
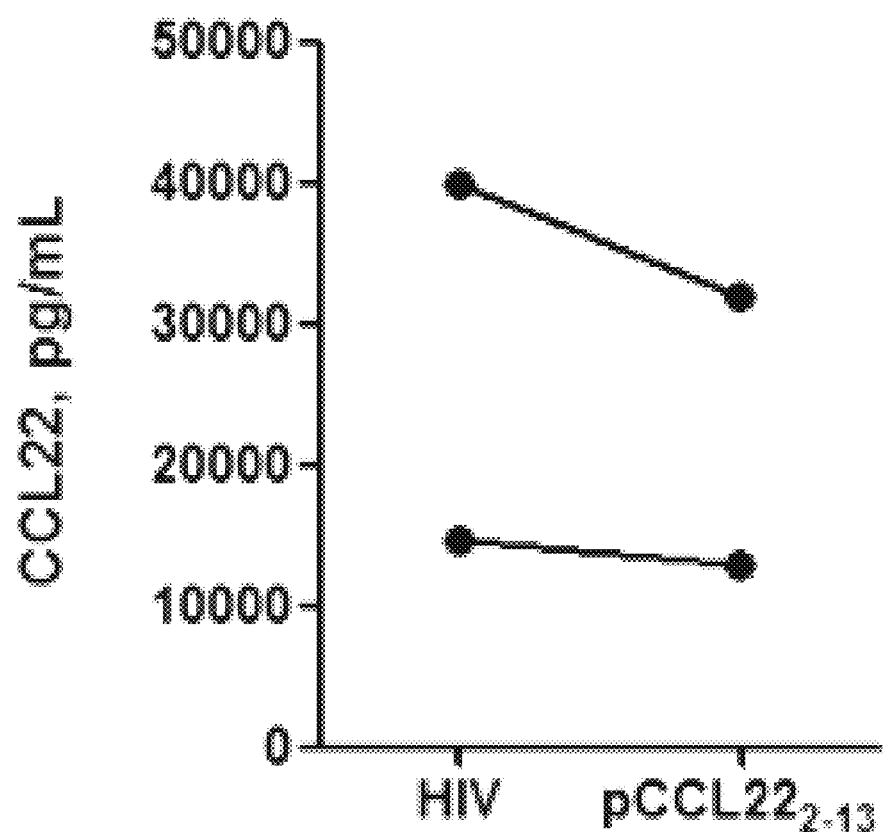

Example 8—pCCL22$_{3-12}$ Stimulation Decreased the CCL22 Levels in the Microenvironment To mimic a setting in which cancer patients are vaccinated with CCL22-derived peptides, we stimulated PMBCs with the pCCL22$_{3-12}$ peptide epitope in vitro and IL-2. We then investigated whether this activation of pCCL22$_{3-12}$-specific T cells affected the overall CCL22 concentration among the PMBCs. First, donor PBMCs that showed a pCCL22$_{3-12}$ response in ELISPOT, were stimulated using the pCCL22$_{3-12}$ peptide, and we measured the CCL22 concentration in the supernatant over one week (FIG. 9A). CCL22 expression was lower in the cultures stimulated with pCCL22$_{3-12}$ peptide compared to cultures stimulated with an HIV control peptide. This difference was apparent after two days of culture and reached significance after one week (P=0.01).

We subsequently used pCCL22$_{3-12}$ peptide or an HIV control peptide to stimulate PBMCs from 11 healthy donors and 13 cancer patients, and then measured the CCL22 concentration in the supernatants one week after stimulation. In PBMCs from healthy donors, the CCL22 concentration significantly decreased following stimulation with pCCL22$_{3-12}$ peptide (P=0.02) (FIG. 9B). On the other hand, in PBMCs from cancer patients, the overall decrease in CCL22 concentration after stimulation with pCCL22$_{3-12}$ did not reach significance (P=0.17) (FIG. 9C). When PBMCs from cancer patients were stratified according to low CCL22 expression (≤2000 pg/mL) and high CCL22 expression (≥5000 pg/mL) (FIG. 9C), the high-expression group showed a significant decrease in CCL22 concentration after pCCL22$_{3-12}$ stimulation (P=0.005).

Ovarian ascetic fluid reportedly contains a mixture of cancer cells and immune-infiltrating cells, along with high levels of CCL22. To examine whether pCCL22$_{3-12}$-specific T cells may influence CCL22 concentration directly in the tumor microenvironment, we collected ascetic fluid from five patients with HLA-A2-positive epithelial ovarian cancer, and isolated the ascites cells. The ascites cells from two of these patients showed low viability and, thus, we could only analyze cells from three patients. The ascites cells from one of these patients did not include any T-lymphocytes. The ascites cells from the remaining two ovarian cancer patients were stimulated with pCCL22$_{3-12}$ peptide, which led to a decrease in the overall CCL22 levels in the supernatants at one week after stimulation (FIG. 9D).

Example 8—pCCL22$_{3-12}$ Stimulation Influenced the Cytokine Milieu

Figure 10:
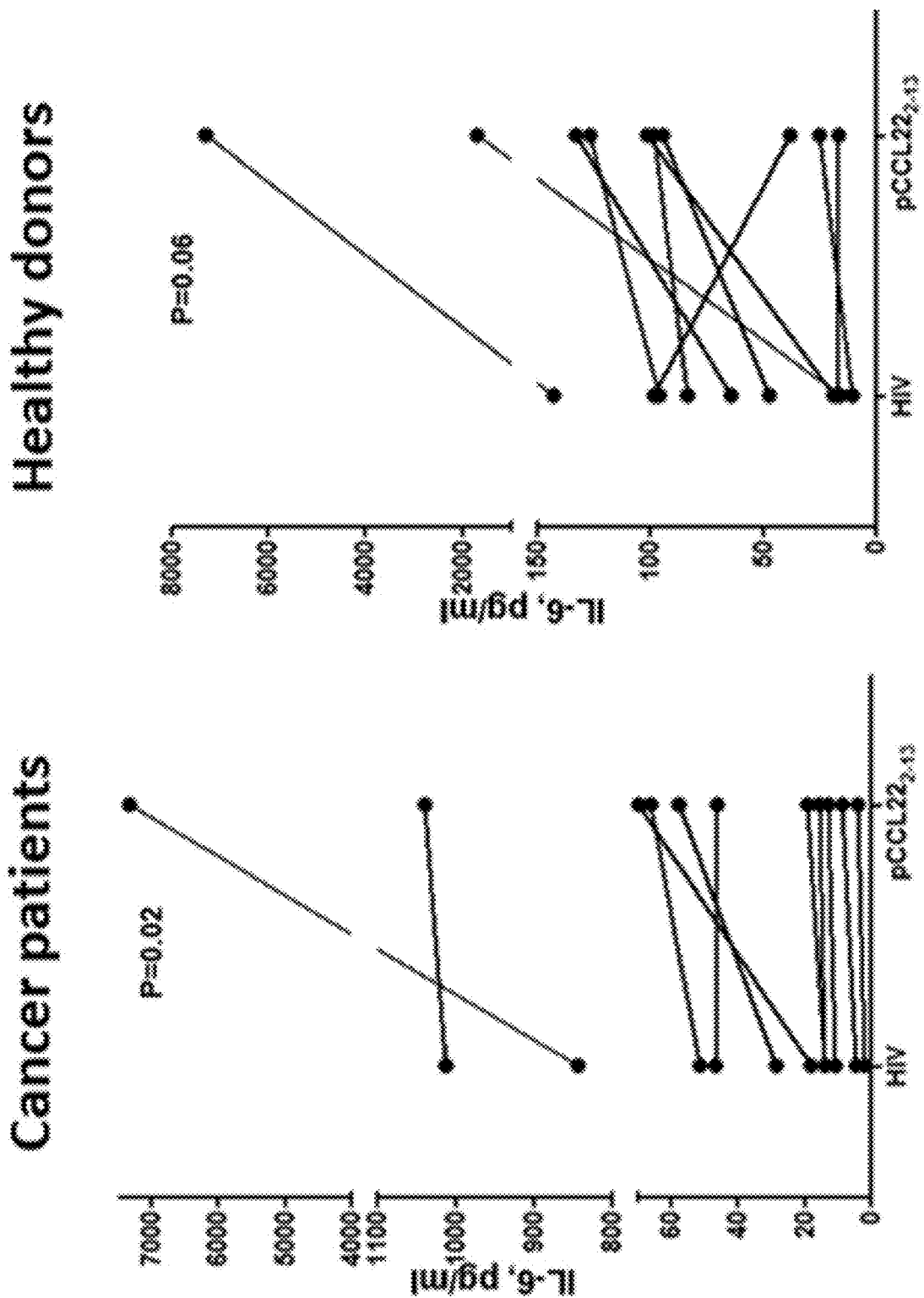
FIG. 10: Stimulation of CCL22-specific T cells affects the PBMC cytokine profile. A—Overall changes in IL-6 expression in supernatants from PBMC isolated from 11 cancer patients (left) or 10 healthy donors (right) after $pCCL22_{3-12}$ stimulation compared to HIV control peptide stimulation (P=0.02 and P=0.06 respectively, paired t-test). B—Overall changes in TNFα expression in supernatants from PBMC isolated from 11 cancer patients (left) or 10 healthy donors (right) after $pCCL22_{3-12}$ stimulation compared to HIV control peptide stimulation (P=0.16 and P=0.7 respectively, paired t-test).
Figure 10:
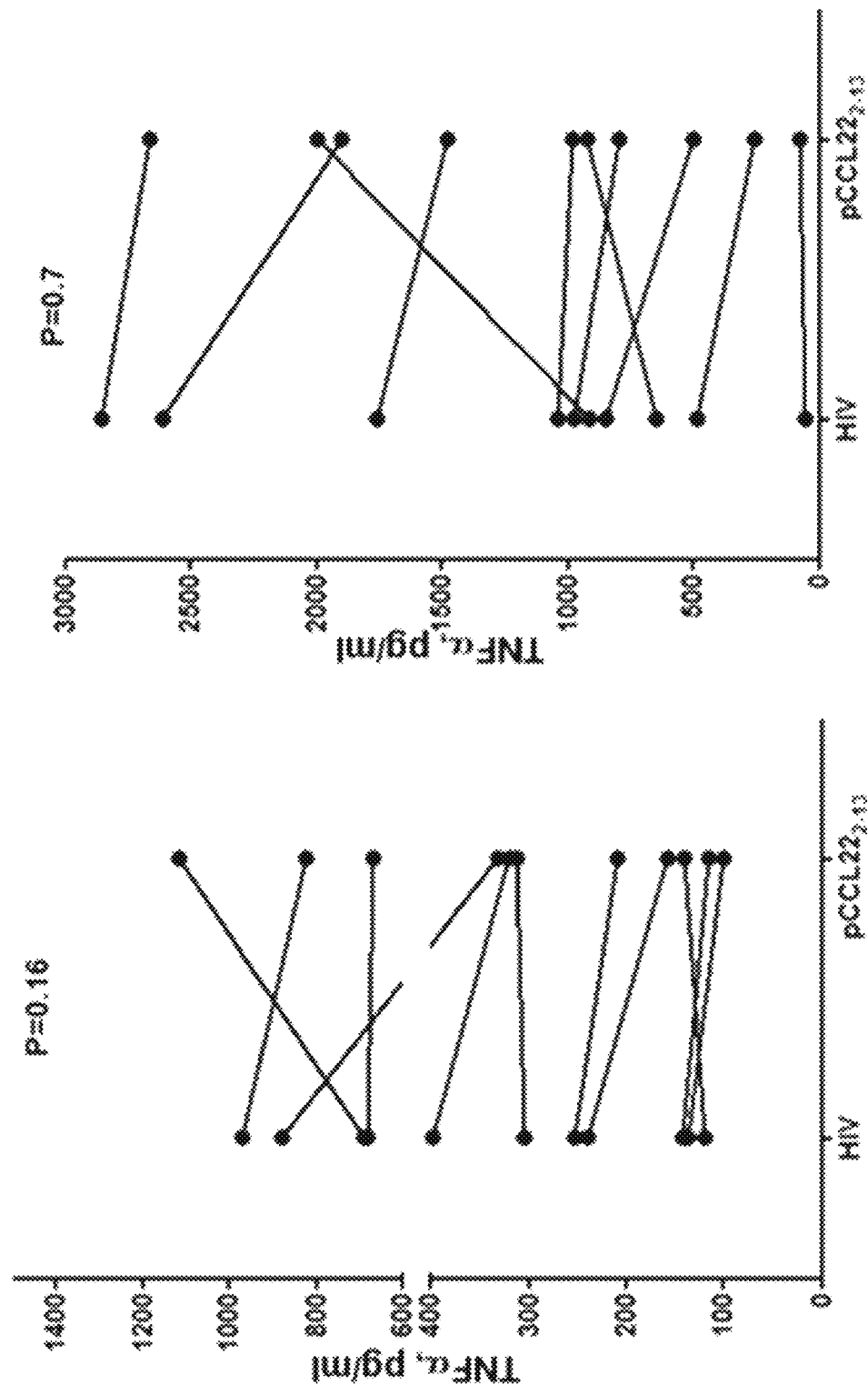

We further examined the PBMC supernatants from 11 cancer patients and 10 healthy donors with regards to changes in cytokine levels after one week of stimulation with pCCL22$_{3-12}$ peptide compared to with an HIV control peptide. The PBMCs from cancer patients that were stimulated with CCL22 peptide showed a significant increase in IL-6 level (P=0.02). A similar increase was observed in cultures of PBMCs from healthy donors, although this change did not reach significance (P=0.06) (FIG. 10A). We also observed a tendency of decreasing TNFα levels in cultures of PBMCs from healthy donors (7 out of 10) and cancer patients (7 out of 11); however, these changes did not reach significance (P=0.7 and P=0.16, respectively) (FIG. 10B). We further examined the concentrations of IL-1β, IL-10, and IFN-γ in the culture supernatants. We detected no unambiguous differences in these cytokines between cultures stimulated with pCCL22$_{3-12}$ peptide versus control peptide. After stimulation, IL-10 was almost undetectable in the supernatants and IL-113 was induced after stimulation with pCCL22$_{3-12}$ in only one cancer patient and two healthy donors (data not shown).

Example 9—Conclusion

Our present findings demonstrated that it was possible for specific T cells to target CCL22-expressing cells.

We demonstrated that it was possible for T cells to recognize an HLA-restricted CCL22-derived peptide epitope, and we were thus able to expand CCL22-specific T cells by re-stimulation of PBMCs with a CCL22 peptide in vitro. The results of our chromium release cytotoxicity assays further demonstrated specific recognition and lysis of CCL22-expressing cancer cells (breast and colon cancer cells, and leukemia cells). Moreover, CCL22 knockdown by siRNA transfection rescued cells from being killed by CCL22-specific T-cells. These findings suggest that in CCL22-expressing cells, the signal peptide is degraded and the epitope is subsequently processed and presented on the cell surface restricted to HLA-A2 molecules. We also found that the CCL22 signal peptide could be taken up and cross-presented on the surface of non-professional antigen-presenting cells.

We used the ELISPOT assay to examine PBMCs from HLA-A2$^+$ cancer patients and healthy individuals for reactivity against the CCL22-derived T-cell epitope, and found that T cells spontaneously reacted to the CCL22-derived peptide. Tetramer enrichment/depletion experiments revealed that the addition of HLA-A2-restricted CCL22-specific T cells to PBMCs decreased the CCL22 level in the microenvironment. We further determined that activation of CCL22-specific T cells via stimulation with the peptide epitope significantly decreased CCL22 levels among PMBCs from both healthy donors and cancer patients with high CCL22 production. Such activation also led to a CCL22 decrease in supernatants of ascites-derived cells isolated from ovarian cancer patients. These findings show that CCL22-specific T cells may be used to target CCL22-expressing cells, and to thereby suppress CCL22-mediated Treg migration into the tumor microenvironment.

Interestingly, activating CCL22-specific T cells by peptide stimulation also resulted in increased release of IL-6 into the PMBC supernatants, showing that CCL22-specific T cells may influence the overall pro-inflammatory microenvironment. ELISPOT results showed spontaneous CCL22-specific T-cell responses in both cancer patients and healthy donors, which was somewhat surprising since CCL22 is abundantly expressed in normal immune cells.

In conclusion, our present results show that CD8+ T cells could recognize an HLA-restricted CCL22 peptide epitope. These T cells recognized and lysed various cancer cell lines in a manner dependent on CCL22 expression, and were naturally present in cancer patients and healthy individuals. Activation of CCL22-specific T cells may directly influence the CCL22 concentration in the microenvironment.

Example 10—Murine CCl22 Peptide Vaccination of C57BL/6

Mice

Female C57BL/6 mice were obtained from Taconic M&B (Denmark) or Janvier (France). All mice were acclimatized for at least one week prior to the initiation of each experiment. Mice entered experiments at ~8-14 weeks of age. The experimental procedures were approved by the national ethics committee on experimental animal welfare and performed according to the Danish guidelines.

Peptides

Two different murine CCL22 peptides: one long peptide, here named mCCL22Long (MATLRVPLLVALVLLAVAI-QTS) and one short peptide, here named mCCL22short (VALVLLAVAI; part of mCCL22Long) were synthesized by TAG Copenhagen (Copenhagen, Denmark).

Peptide Vaccination

Murine CCL22 peptide (TAG Copenhagen, Denmark) stocks of 10 mM (mCCL22Short) and 5 mM (mCCL22Long) were made in DMSO. Mice were vaccinated subcutaneously (s.c) on the lower back with 100 μg peptide in 1:1 (vol/vol) IFA/PBS emulsion in a total volume of 100 μl. Mice were vaccinated once a week for 3 weeks and sacrificed one week after the last vaccination.

Preparation of Splenocyte Single Cell Solution

Spleens from sacrificed mice were removed and smashed through a cell strainer (0.7 μm) and washed with R10 media: RPMI 1640 (Gibco® by Life Technologies™) with 10% FCS (Gibco® by Life Technologies™). Red blood cells lysed by adding red blood cell lysis buffer for 2 min, followed by two washes with R10 with 10% fetal bovine serum.

ELISPOT Assay

ELISPOT was performed as described by the manufacturer's instruction. In short, 96-well MSIPN4W ELISPOT plate (Millipore) were coated with mouse IFNy-specific capture Ab (AN18; Mabtech) in a concentration of 12 μg/ml in PBS overnight at 4° C. 8×10$^5$ or 4×10$^5$ splenocytes/well were seeded in the plate in triplicates. To investigate IFNy response to murine CCL22 peptides, cells were incubated with different peptides (5 μM) or R10 as control for 18-20 h at 37° C. ELISPOT was developed with mouse IFNy-specific detection Ab (R4-6A2-biotin; Mabtech) in a concentration of 1 μg/ml in Buffer (PBS, 0.5% BSA and NaN$_3$) for 2 h at room temperature, followed by 6 washes in PBS. Next, adding of streptavidin-ALP (1:1000; Mabtech) in Buffer for 1 h at room temperature. Spots were developed by adding substrate solution BCIP/NBT (Mabtech) and stopped by washing in tap water.

Figure 11:
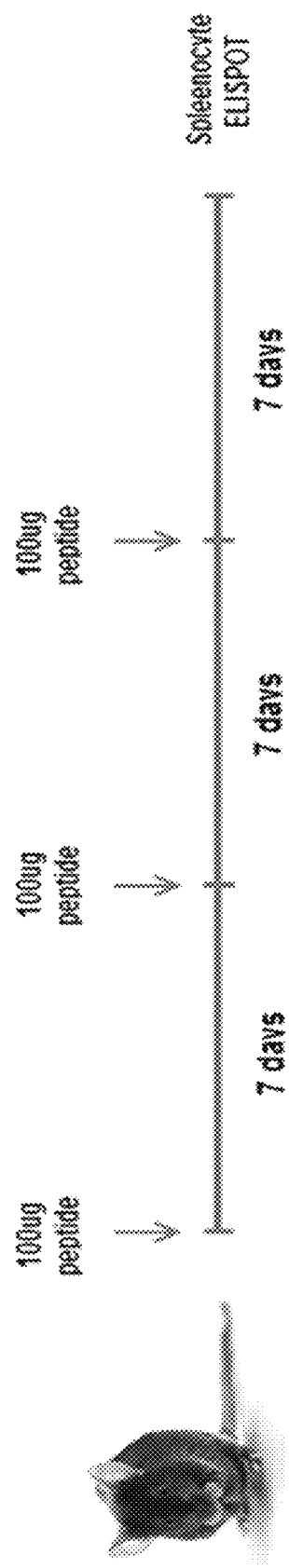
FIG. 11: An immune response can be raised in vivo. Mice were vaccinated by subcutaneous injections of either mCCL22long (SEQ ID NO: 13) or mCCL22short (SEQ ID NO: 14) as shown in the upper panel, once a week over a period of three weeks, before being sacrificed one week after the last vaccination. ELISPOT assays were performed on splenocytes prepared from the spleens of the sacrificed mice. To investigate IFNγ response to murine CCL22 peptides, cells were incubated with the peptides (5 µM) or R10 as control for 18-20 h at 37° C. ELISPOT was developed with mouse IFNγ-specific detection Ab (R4-6A2-biotin; Mabtech) in a concentration of 1 µg/ml in Buffer (PBS, 0.5% BSA and NaN3) for 2 h at room temperature, followed by 6 washes in PBS. Next, adding of streptavidin-ALP (1:1000; Mabtech) in Buffer for 1 h at room temperature. Spots were developed by adding substrate solution BCIP/NBT (Mabtech) and stopped by washing in tap water. The ELISPOTs were analyzed by ELISPOT Reader (CTL-Immunospot). The results show that the vaccinated mice display an increased immune response.
Figure 11:
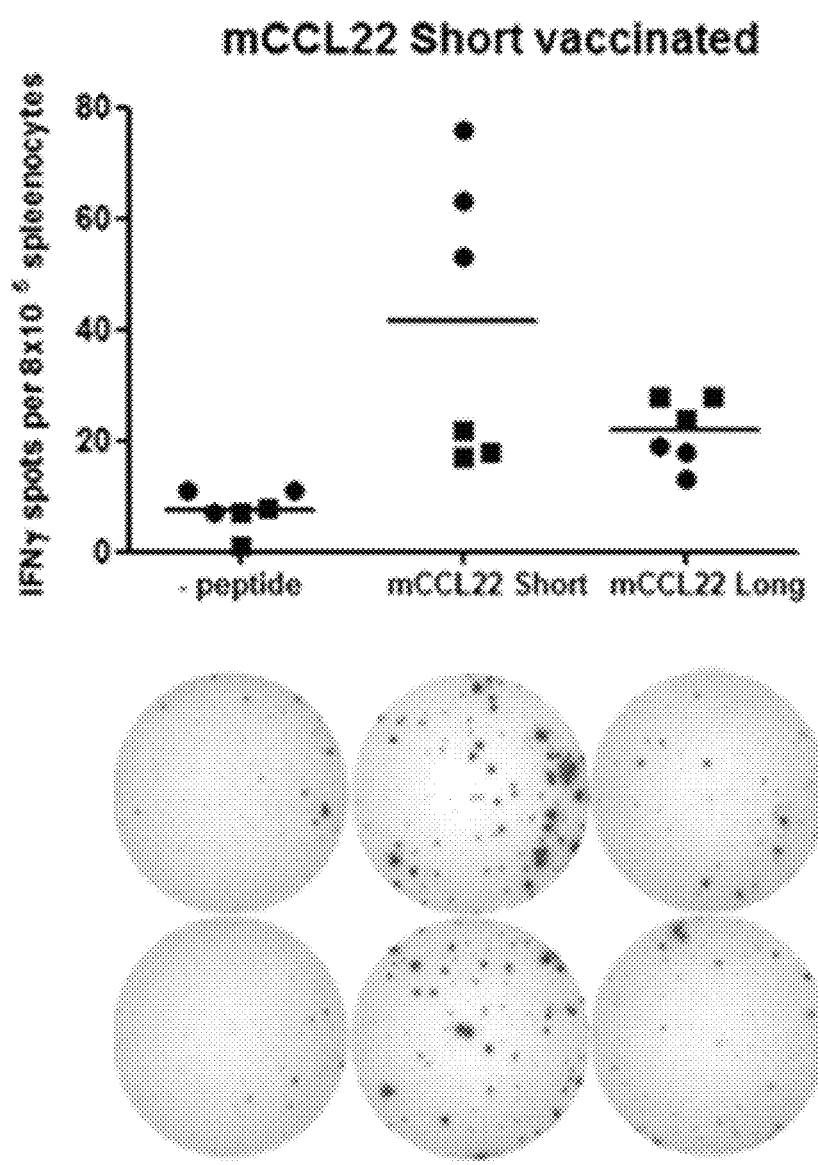
Figure 11:
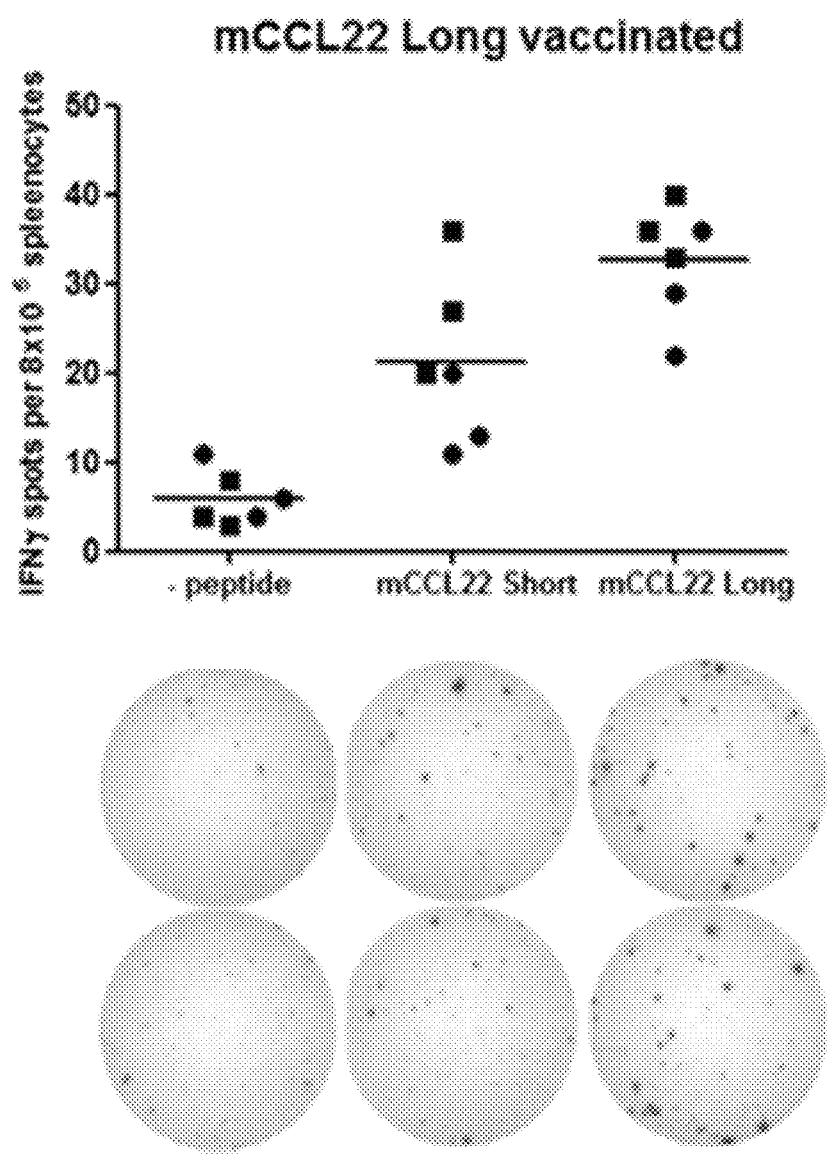

ELISPOT were analyzed by ELISPOT Reader (CTL-Immunospot). The results are presented in FIG. 11, and show that an immune response can be raised in vivo using the peptides of the present disclosure.

REFERENCES

Andersen M H, Bonfill J E, Neisig A, Arsequell G, Sondergaard I, Valencia G, et al. Phosphorylated Peptides Can Be Transported by TAP Molecules, Presented by Class I MHC Molecules, and Recognized by Phosphopeptide-Specific CTL. J Immunol 1999; 163:3812-8

Hobo W, Maas F, Adisty N, de W T, Schaap N, van d, V, et al. siRNA silencing of PD-L1 and PD-L2 on dendritic cells augments expansion and function of minor histocompatibility antigen-specific CD8+ T cells. Blood 2010; 116:4501-11

Met O, Balslev E, Flyger H, Svane I M. High immunogenic potential of p53 mRNA-transfected dendritic cells in patients with primary breast cancer. Breast Cancer Res Treat 2011; 125:395-406.

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A. Cancer regression in patients after transfer of genetically engineered lymphocytes. Science. 2006 Oct. 6; 314 (5796):126-9. Epub 2006 Aug. 31.

Nicolette C A, Healey D, Tcherepanova I, Whelton P, Monesmith T, Coombs L, Finke L H, Whiteside T, Miesowicz F, (2007). Dendritic cells for active immunotherapy: optimizing design and manufacture in order to develop commercially and clinically viable products. Vaccine, September 27; 25 Suppl 2:B47-60. Epub 2007

Nomi T, Sho M, Akahori T, Hamada K, Kubo A, Kanehiro H et al. Clinical significance and therapeutic potential of the programmed death-1 ligand/programmed death-1 pathway in human pancreatic cancer. Clin Cancer Res 2007; 13:2151-2157.

Pilotte L, Larrieu P, Stroobant V, Colau D, Dolusic E, Frédérick R, et al. Reversal of tumoral immune resistance by inhibition of tryptophan 2,3-dioxygenase. Proc Natl Acad Sci USA [Internet]. 2012 [cited 2013 Apr. 6]; 109:2497-502

Rammensee H, Bachmann J, Emmerich N P, Bachor O a, Stevanović S. SYFPEITHI: database for MHC ligands and peptide motifs. Immunogenetics [Internet]. 1999; 50:213-9.

Sorensen R B, Berge-Hansen L, Junker N, Hansen C A, Hadrup S R, Schumacher T N M, et al. The immune system strikes back: cellular immune responses against indoleamine 2,3-dioxygenase. PLoS One [Internet]. 2009 [cited 2012 Aug. 15]; 4:e6910

Toebes M, Coccoris M, Bins A, Rodenko B, Gomez R, Nieuwkoop N J, et al. Design and use of conditional MHC class I ligands. Nat Med. 2006; 12:246

Walter E A, Greenberg P D, Gilbert M J, Finch R J, Watanabe K S, Thomas E D, Riddell S R (1995). Reconstitution of cellular immunity against cytomegalovirus in recipients of allogeneic bone marrow by transfer of T-cell clones from the donor. N Engl J Med. 1995 Oct. 19; 333(16):1038-44

Zeeberg Iversen T, Engell-Noerregaard L, Ellebaek E, Andersen R, Kiaer Larsen S, Bjoern J, et al. Long-lasting disease stabilization in the absence of toxicity in metastatic lung cancer patients vaccinated with an epitope derived from indoleamine 2,3 dioxygenase. Clin cancer Res [Internet]. 2013 [cited 2013 Nov. 14]

The invention claimed is:

1. An immunogenically active peptide fragment of CCL22 consisting of at the most 50 consecutive residues of SEQ ID NO: 12, wherein said peptide fragment is of at least 25 amino acids and contains a sequence selected from the group consisting of SEQ ID NO: 1, SEQ ID NO: 3, SEQ ID NO: 4, SEQ ID NO: 5, and SEQ ID NO: 11.

2. The peptide fragment according to claim 1, wherein the peptide fragment comprises the sequence of SEQ ID NO: 5.

3. A composition comprising the peptide fragment of claim 1 and an adjuvant.

4. The composition according to claim 3, further comprising an immunogenically active protein or peptide fragment selected from a protein or peptide fragment, which is not CCL22.

5. The composition according to claim 3, wherein the adjuvant is selected from the group consisting of bacterial DNA based adjuvants, oil/surfactant based adjuvants, viral dsRNA based adjuvants and imidazochinilines.

* * * * *